US011780861B2

(12) United States Patent
McNally et al.

(10) Patent No.: US 11,780,861 B2
(45) Date of Patent: Oct. 10, 2023

(54) PHOSPHINE REAGENTS FOR AZINE FLUOROALKYLATION

(71) Applicant: COLORADO STATE UNIVERSITY RESEARCH FOUNDATION, Fort Collins, CO (US)

(72) Inventors: Andrew McNally, Fort Collins, CO (US); Kyle Nottingham, Fort Collins, CO (US); Chirag Patel, Fort Collins, CO (US); Jeffrey Levy, Fort Collins, CO (US); Xuan Zhang, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 17/634,140

(22) PCT Filed: Oct. 20, 2021

(86) PCT No.: PCT/US2021/055842
§ 371 (c)(1),
(2) Date: Feb. 9, 2022

(87) PCT Pub. No.: WO2022/087129
PCT Pub. Date: Apr. 28, 2022

(65) Prior Publication Data
US 2022/0380394 A1    Dec. 1, 2022

Related U.S. Application Data

(60) Provisional application No. 63/094,623, filed on Oct. 21, 2020.

(51) Int. Cl.
*C07F 9/50* (2006.01)
*C07F 9/572* (2006.01)
*C07B 47/00* (2006.01)

(52) U.S. Cl.
CPC ............. *C07F 9/572* (2013.01); *C07B 47/00* (2013.01); *C07F 9/5022* (2013.01)

(58) Field of Classification Search
None
See application file for complete search history.

(56) References Cited

U.S. PATENT DOCUMENTS

2017/0349567 A1    12/2017 Umemoto et al.

OTHER PUBLICATIONS

Database Registry Chemical Abstracts Service, Columbus, Ohio, Accession No. RN 1023971-92-7, Entered STN: May 30, 2008.*
Alonso et al., "Carbon Trifluoromethylation Reactions of Hydrocarbon Derivatives and Heteroarenes," Chem. Rev., 115(4):1847-1935, Jan. 2015.
Boyle et al., "Nonsymmetrical Bis-Azine Biaryls from Chloroazines: A Strategy Using Phosphorus Ligand-Coupling," J Am Chem Soc., 141(38):15441-15449, Sep. 2019.
Dolewski et al., "Site-Selective Switching Strategies to Functionalize Polyazines," J Am Chem Soc., 140(25):8020-8026, May 2018.
Fujiwara et al., "Practical and Innate C—H Functionalization of Heterocycles," Nature, 492(7427):95-99, Dec. 2012.
Hilton et al., "Heterobiaryl Synthesis by Contractive C—C Coupling via P(V) Intermediates," Science, 362(6416):799-804, Nov. 2018.
Hilton et al., "Selective Functionalization of Pyridines via Heterocyclic Phosphonium Salts," J Am Chem Soc., 138(42):13806-13809, Oct. 2016.
International Search Report and Written Opinion of the ISA/US in PCT/US2021/055842, dated Jan. 21, 2022, 6pgs.
Kleoff et al. "Electrophilic Trifluoromethylation". Science of Synthesis Knowledge Updates. 1-20 2018. 4,236, especially: p. 1, Table, fifth entry.
Nagib et al., "Trifluoromethylation of Arenes and Heteroarenes by Means of Photoredox Catalysis," Nature, 480:224-228, Dec. 2011.
PubChem-SID-212343355, Modify Date: Jun. 2, 2019 (Jun. 2, 2019), p. 2, figure, this is a 1-20 purchasable chemical.
Ye et al., "Aryl Sulfonium Salts for Site-Selective Late-Stage Trifluoromethylation," Angew Chem Int Ed Engl., 58(41):14615-14619, Oct. 2019.
Zhang et al., "Phosphorus-mediated sp2-sp3 Couplings for C—H Fluoroalkylation of Azines," Nature, 594:217-222, Apr. 2021.

* cited by examiner

*Primary Examiner* — Samantha L Shterengarts
(74) *Attorney, Agent, or Firm* — Haukaas Fortius PLLC; Michael Haukaas

(57) ABSTRACT

A new set of bench-stable fluoroalkylphosphines that directly convert C—H bonds in pyridine building blocks, drug-like fragments, and pharmaceuticals, into fluoroalkyl derivatives. No pre-installed functional groups or directing motifs are required. The reaction tolerates a variety of sterically and electronically distinct pyridines and is exclusively selective for the 4-position in most cases. The reaction proceeds via initial phosphonium salt formation followed by $sp^2$-$sp^3$ phosphorus ligand-coupling, an underdeveloped manifold for C—C bond formation.

20 Claims, No Drawings

PHOSPHINE REAGENTS FOR AZINE FLUOROALKYLATION

RELATED APPLICATIONS

This application is a National Stage filing under 35 U.S.C. § 371 of International Application No. PCT/US2021/055842 filed Oct. 20, 2021, which claims priority under 35 U.S.C. § 119(e) to U.S. Provisional Patent Application No. 63/094,623 filed Oct. 21, 2020, which applications are incorporated herein by reference.

GOVERNMENT SUPPORT

This invention was made with government support under Grant No. 1753087 awarded by the National Science Foundation. The government has certain rights in the invention.

BACKGROUND OF THE INVENTION

Fluoroalkyl groups' impact on structure-activity relationship (SAR) studies and the prevalence of pyridines in drugs and agrochemicals has resulted in numerous fluoroalkylated candidates and marketed compounds (Scheme 1a). Strategically installing trifluoromethyl groups can increase hydrophobic binding contacts, improve cell membrane permeability, and limit metabolic susceptibility; difluoromethyl groups also serve as surrogates of hydroxyl, thiol, and amine derivatives. Furthermore, the inductive withdrawing effects of fluoroalkyl groups reduce pyridine heterocycle's basicity and offset excessive binding to CYP enzymes, an off-target effect that can result in numerous adverse consequences and unwanted drug-drug interactions.

Synthesizing fluoroalkyl pyridines from acyclic precursors provides simple building block compounds. However, in discovery campaigns, it is preferable to transform existing pyridines into fluoroalkyl derivatives because of the large variability in candidate structures. To that end, metal-catalyzed cross-couplings and C—H functionalization reactions are the most common ways to make pyridyl C—$CF_2$X bonds. The latter is advantageous for complex substrates as they do not typically contain pre-installed functional groups, such as (pseudo)halides and boronic acids, required to generate organometallic intermediates, and instead exploit ubiquitous C—H bonds.

Surprisingly, the only viable strategy for this endeavor is Minisci-type radical processes. As the C—C bond-forming step in these reactions occurs via the same mechanism, the amenable set of pyridine inputs is defined and the regiochemical outcomes are a function of the reaction conditions and pyridine substituents. Kanai reported a process to fluoroalkylate azines where trifluoromethyl anions add to preformed borane adducts (J. Am. Chem. Soc. 138, 6103). An overall three-stage protocol is required, and the reaction is moderately selective for the 4-position of pyridines. Limited evidence of the reaction's capacity to fluoroalkylate drug-like molecules again reinforces the need for new reactions that can impact drug discovery.

SUMMARY

This disclosure provides the design for a mechanistically distinct process for pyridine C—H fluoroalkylation via phosphorus ligand-coupling reactions. Using fluoroalkylphosphines as reagents, a unique regiochemical profile and suite of complex pyridine substrates mean new chemical space is accessible for pharmaceutical and agrochemical discovery. (Scheme 1c).

Accordingly, this disclosure provides a phosphine compound of Formula I:

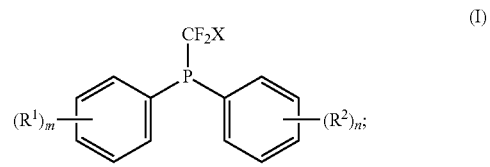

wherein
X is H, F, —($C_1$-$C_6$)perfluoroalkyl, or —($C_1$-$C_6$)alkyl;
$R^1$ and $R^2$ are each independently $NR^aR^b$, $OR^c$, $SR^d$, —($C_3$-$C_6$)cycloalkyl, or —($C_1$-$C_6$)alkyl;
$R^a$ and $R^b$ are each independently H, —($C_1$-$C_6$)alkyl, or —($C_3$-$C_6$)cycloalkyl; or
$R^a$ and $R^b$ taken together form a 5-membered or 6-membered heterocycle with the nitrogen moiety of $NR^aR^b$;
$R^c$ and $R^d$ are each independently H, —($C_1$-$C_6$)alkyl, or —($C_3$-$C_6$)cycloalkyl; and
m and n are each independently 1 or 2;
wherein each —($C_1$-$C_6$)alkyl is independently unbranched or branched, and optionally substituted.

This disclosure also provides a method for fluoroalkylation of an organic compound comprising:
a) contacting a phosphine compound of any of Formulas I, IA, II, IIA, IIB, III, IV, V, VI, VII, and VIII disclosed herein, the organic compound, and a solvent under suitable reaction conditions to form a phosphonium salt of the organic compound; and
b) contacting the phosphonium salt and an aqueous solution or a mixture of an organic solvent and a base;
wherein a fluoroalkylated organic compound is thereby formed.

The invention provides novel compounds of Formula I, IA, II, IIA, IIB, III, IV, V, VI, VII, and VIII, intermediates for the synthesis of compounds of Formula I, IA, II, IIA, IIB, III, IV, V, VI, VII, and VIII, as well as methods of preparing compounds of Formula I, IA, II, IIA, IIB, III, IV, V, VI, VII, and VIII. The invention also provides compounds of Formula I, IA, II, IIA, IIB, III, IV, V, VI, VII, and VIII that are useful as intermediates for the synthesis of other useful compounds.

Scheme 1. Importance of fluoroalkylated pyridines and methods to make C—$CF_2$X bonds (X=F or H). a, Examples of fluoroalkylated pyridines in pharmaceuticals and agrochemicals. b, Minisci-type methods for C—$CF_2$X bond formation. c, New phosphine reagents for C—H fluoroalkylation of pyridines via phosphorus ligand-coupling.
a. Fluoroalkylated pyridines are common in pharmaceuticals and agrochemicals.

| $CF_3$ | | $CF_2H$ |
|---|---|---|
| Enhanced resistance to oxidative metabolism | Improved potency Modulated lipophilicity | Bioisostere for OH, SH H-bond donor |

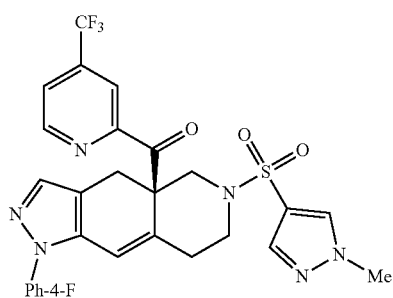

Relacorilant
Cushing's syndrome

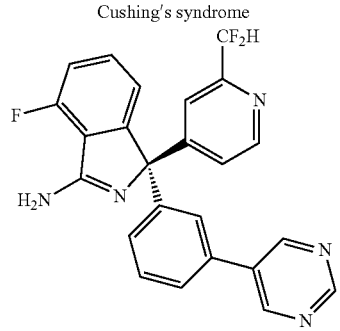

AZD3839
Alzheimer's disease

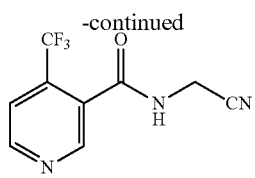

Flonicamid
Insecticide

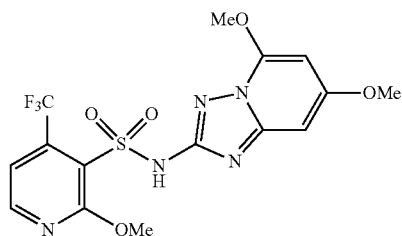

Pyroxsulam
Herbiciode b. Only general method for late-stage fluoroalkylation of complex pyridines: C—H fluoroalkylation of complex pyridines via open shell pathways.

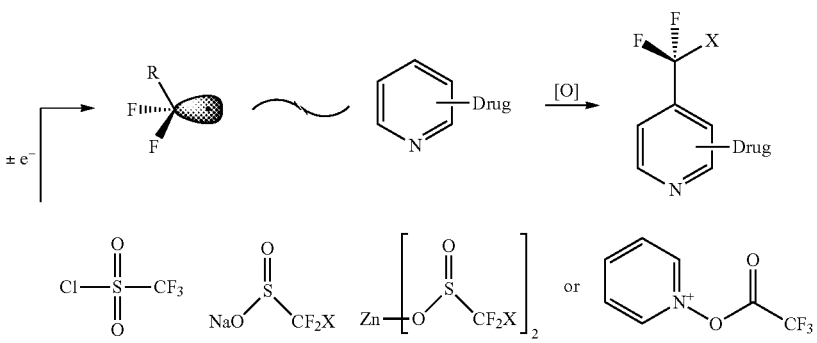

c. New opportunities in drug and agrochemical discovery: bench-stable phosphines for 4-selective C—H fluoroalkylation of complex pyridines.

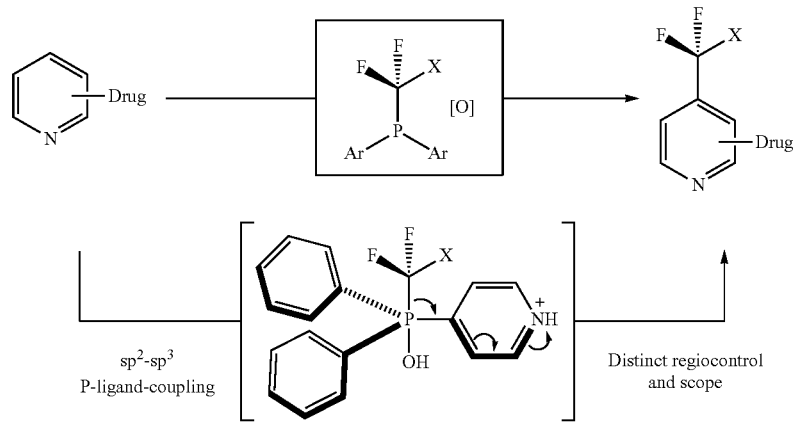

DETAILED DESCRIPTION

Fluoroalkyl groups profoundly affect the physical properties of pharmaceuticals and influence virtually all metrics associated with their pharmacokinetic and pharmacodynamic profile. Drug candidates increasingly contain $CF_3$ and $CF_2H$ groups, and the same trend in agrochemical development shows a remarkable translation across human, insect, and plant life. New fluoroalkylation reactions have undoubtedly stimulated this uptake; however, methods that directly convert C—H bonds into C—$CF_2X$ (X=F or H) groups in complex drug-like molecules are rare. In particular, pyridine is the most common aromatic heterocycle in pharmaceuticals, yet only one approach, via fluoroalkyl radicals, is viable for pyridyl C—H fluoroalkylation in the elaborate structures encountered during drug development.

Additional information and data supporting the invention can be found in the following publication by the inventors: *Nature* 2021, 594, 217-222 and its Supporting Information, which is incorporated herein by reference in its entirety.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

Wherever the term "comprising" is used herein, options are contemplated wherein the terms "consisting of" or "consisting essentially of" are used instead. As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the aspect element. As used herein, "consisting essentially of" does not exclude materials or steps that do not materially affect the basic and novel characteristics of the aspect. In each instance herein any of the terms "comprising", "consisting essentially of" and "consisting of" may be replaced with either of the other two terms. The disclosure illustratively described herein may be suitably practiced in the absence of any element or elements, limitation or limitations which is not specifically disclosed herein.

This disclosure provides methods of making the compounds and compositions of the invention. The compounds and compositions can be prepared by any of the applicable techniques described herein, optionally in combination with standard techniques of organic synthesis. Many techniques such as etherification and esterification are well known in the art. However, many of these techniques are elaborated in Compendium of Organic Synthetic Methods (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6; as well as standard organic reference texts such as March's Advanced Organic Chemistry: Reactions, Mechanisms, and Structure, 5th Ed., by M. B. Smith and J. March (John Wiley & Sons, New York, 2001); Comprehensive Organic Synthesis. Selectivity, Strategy & Efficiency in Modern Organic Chemistry. In 9 Volumes, Barry M. Trost, Editor-in-Chief (Pergamon Press, New York, 1993 printing); Advanced Organic Chemistry, Part B: Reactions and Synthesis, Second Edition, Cary and Sundberg (1983); for heterocyclic synthesis see Hermanson, Greg T., Bioconjugate Techniques, Third Edition, Academic Press, 2013.

The formulas and compounds described herein can be modified using protecting groups. Suitable amino and carboxy protecting groups are known to those skilled in the art (see for example, Protecting Groups in Organic Synthesis, Second Edition, Greene, T. W., and Wutz, P. G. M., John Wiley & Sons, New York, and references cited therein; Philip J. Kocienski; Protecting Groups (Georg Thieme Verlag Stuttgart, New York, 1994), and references cited therein); and Comprehensive Organic Transformations, Larock, R. C., Second Edition, John Wiley & Sons, New York (1999), and referenced cited therein.

The term "halo" or "halide" refers to fluoro, chloro, bromo, or iodo. Similarly, the term "halogen" refers to fluorine, chlorine, bromine, and iodine.

The term "alkyl" refers to a branched or unbranched hydrocarbon having, for example, from 1-20 carbon atoms, and often 1-12, 1-10, 1-8, 1-6, or 1-4 carbon atoms; or for example, a range between 1-20 carbon atoms, such as 2-6, 3-6, 2-8, or 3-8 carbon atoms. As used herein, the term "alkyl" also encompasses a "cycloalkyl", defined below. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below or otherwise described herein. The alkyl can also be optionally partially or fully unsaturated. As such, the recitation of an alkyl group can include an alkenyl group or an alkynyl group. The alkyl can be a monovalent hydrocarbon radical, as described and exemplified above, or it can be a divalent hydrocarbon radical (i.e., an alkylene).

An alkylene is an alkyl group having two free valences at a carbon atom or two different carbon atoms of a carbon chain. Similarly, alkenylene and alkynylene are respectively an alkene and an alkyne having two free valences at two different carbon atoms.

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "heterocycloalkyl" or "heterocyclyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazepane, and 1,4-oxathiapane. The group may be a terminal group or a bridging group.

The term "aromatic" refers to either an aryl or heteroaryl group or substituent described herein. Additionally, an aromatic moiety may be a bisaromatic moiety, a trisaromatic moiety, and so on. A bisaromatic moiety has a single bond between two aromatic moieties such as, but not limited to, biphenyl, or bipyridine. Similarly, a trisaromatic moiety has a single bond between each aromatic moiety.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted with a substituent described below.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms, wherein the ring skeleton comprises a 5-membered ring, a 6-membered ring, two 5-membered rings, two 6-membered rings, or a 5-membered ring fused to a 6-membered ring.

The term "azine heterocycle" or "azine" as used herein is a heterocyclic compound comprising a 6-membered aromatic ring and one or more nitrogen atoms in the ring. Examples include pyridine, diazine, triazine, and tetrazine.

As used herein, the term "substituted" or "substituent" is intended to indicate that one or more (for example, in various embodiments, 1-10; in other embodiments, 1-6; in some embodiments 1, 2, 3, 4, or 5; in certain embodiments, 1, 2, or 3; and in other embodiments 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, haloalkyl, hydroxyalkyl, aryl, heteroaryl, heterocyclyl, cycloalkyl, alkanoyl, alkoxycarbonyl, amino, alkylamino, dialkylamino, carboxyalkyl, alkylthio, alkylsulfinyl, and alkylsulfonyl. Substituents of the indicated groups can be those recited in a specific list of substituents described herein, or as one of skill in the art would recognize, can be one or more substituents selected from alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, and cyano. Suitable substituents of indicated groups can be bonded to a substituted carbon atom include F, Cl, Br, I, OR', OC(O)N(R')2, CN, CF3, OCF3, R', O, S, C(O), S(O), methylenedioxy, ethylenedioxy, N(R')2, SR', SOR', SO2R', SO2N(R')2, SO3R', C(O)R', C(O)C(O)R', C(O)CH2C(O)R', C(S)R', C(O)OR', OC(O)R', C(O)N(R')2, OC(O)N(R')2, C(S)N(R')2, (CH2)0-2NHC(O)R', N(R')N (R')C(O)R', N(R')N(R')C(O)OR', N(R')N(R')CON(R')2, N(R')SO2R', N(R')SO2N(R')2, N(R')C(O)OR', N(R')C(O) R', N(R')C(S)R', N(R')C(O)N(R')2, N(R')C(S)N(R')2, N(COR')COR', N(OR')R', C(=NH)N(R')2, C(O)N(OR')R', or C(=NOR')R' wherein R' can be hydrogen or a carbon-based moiety (e.g., (C1-C6)alkyl), and wherein the carbon-based moiety can itself be further substituted.

The term "apicophilic" refers to a phenomenon in which electronegative substituents of trigonal bipyramidal pentacoordinate compounds prefer to occupy apical positions.

The term "drug discovery" or "agrochemical discovery" refers to a process known to persons skilled in the art, a process comprising, but not limited to, the synthesis of small molecule compounds or chemical libraries of small molecule compounds, medicinal chemistry, scale up, process synthesis, or large-scale manufacturing of small molecule compounds, and biological screening or testing of small molecule compounds.

EMBODIMENTS OF THE INVENTION

This disclosure provides a phosphine compound of Formula I or Formula II:

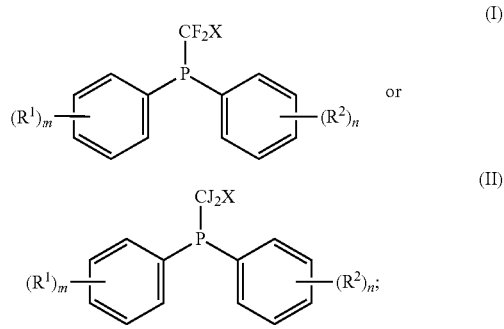

wherein
X is H, F, —(C$_1$-C$_6$)perfluoroalkyl, or —(C$_1$-C$_6$)alkyl;
each J is independently H, F, —(C$_1$-C$_6$)perfluoroalkyl, or —(C$_1$-C$_6$)alkyl;
R$^1$ and R$^2$ are each independently NR$^a$R$^b$, OR$^c$, SR$^d$, —(C$_3$-C$_6$)cycloalkyl, or —(C$_1$-C$_6$)alkyl;

$R^a$ and $R^b$ are each independently H, —($C_1$-$C_6$)alkyl, or —($C_3$-$C_6$)cycloalkyl; or $R^a$ and $R^b$ taken together form a 5-membered or 6-membered heterocycle with the nitrogen moiety of $NR^aR^b$;

$R^c$ and $R^d$ are each independently H, —($C_1$-$C_6$)alkyl, or —($C_3$-$C_6$)cycloalkyl; and m and n are each independently 1 or 2;

wherein each —($C_1$-$C_6$)alkyl is independently unbranched or branched, and optionally substituted.

In some embodiments, each J is independently H, F, or $CF_3$, or $CO_2H$. In some embodiments, X is not F when $R^1$ and $R^2$ are $OCH_3$ or $CH_3$ wherein $R^1$ and $R^2$ are each in the para-position and m and n are each 1. In other various embodiments, $R^1$ and $R^2$ are each in the para-position and m and n are each 1.

In some embodiments, $R^1$ is in the ortho- and para-position when m is 2. In some embodiments, $R^2$ is in the ortho- and para-position when m is 2. In some embodiments, $R^1$ and $R^2$ are each independently in the ortho-position, meta-position, or para-position.

In other embodiments, the phosphine compound of Formula I is represented by a phosphine compound of Formula IA:

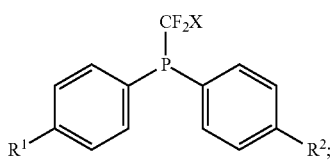

(IA)

wherein X is not F when $R^1$ and $R^2$ are $OCH_3$ or $CH_3$.

$R^a$, $R^b$, $R^c$, and $R^d$ are each independently —($C_1$-$C_6$)alkyl, or —($C_3$-$C_6$)cycloalkyl. In various embodiments, $R^a$ is —($C_1$-$C_6$)alkyl. In various embodiments, $R^b$ is —($C_1$-$C_6$)alkyl. In various other embodiments, $R^c$ is —($C_1$-$C_6$)alkyl. In various other embodiments, $R^d$ is —($C_1$-$C_6$)alkyl.

In some embodiments, X is H. In some other embodiments, X is F. In other embodiments, X is perfluoroalkyl. In other embodiments, X is —($C_1$-$C_6$)perfluoroalkyl wherein the ($C_1$-$C_6$) moiety of —($C_1$-$C_6$)perfluoroalkyl comprises two or more F. In other embodiments, X is —($C_1$-$C_6$) perfluoroalkyl wherein each carbon of the ($C_1$-$C_6$) moiety of —($C_1$-$C_6$)perfluoroalkyl is substituted with one or more F. In other embodiments, X is $CF_3$, $CF_2H$, $CF_2CF_3$, $CF_2HCF_3$, $CF_2HCF_2H$, $CF_2CF_2CF_3$, $CF_2CF_2CF_2CF_3$, $CF_2CF_2CF_2CF_2CF_3$, or $CF_2CF_2CF_2CF_2CF_2CF_3$. In other embodiments, $R^1$ and $R^2$ are $NR^aR^b$. In other embodiments, $R^a$ and $R^b$ are methyl or ethyl. In yet other embodiments, $NR^aR^b$ is pyrrolidinyl or piperidinyl. In other embodiments, $R^1$ and $R^2$ are $OR^c$. In further embodiments, $R^c$ is methyl or ethyl. In additional embodiments, X is F, and $R^1$ and $R^2$ are $NR^aR^b$. In other embodiments, X is F, and $R^1$ and $R^2$ are $N(CH_3)_2$ or 1-pyrrolidinyl. In other embodiments, X is H, and $R^1$ and $R^2$ are $OR^c$. In some embodiments, X is H, and $R^1$ and $R^2$ are methoxy or ethoxy.

In some other embodiments, the phosphine compound is:

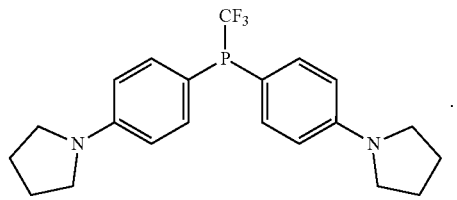 [SMILES: FC(F)(F)P(c1ccc(N2CCCC2)cc1)c1ccc(N2CCCC2)cc1]

In yet other embodiments, the phosphine compound is:

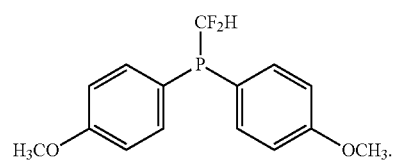 [SMILES: COc1ccc(P(c2ccc(OC)cc2)C(F)F)cc1]

Furthermore, this disclosure provides a phosphine compound of Formula II:

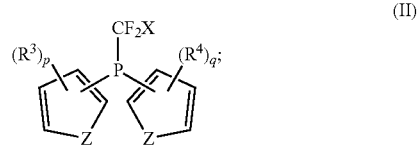

(II)

wherein

X is H, F, or —($C_1$-$C_6$)perfluoroalkyl;

Z is O, S, or $NR^y$ wherein $R^y$ is H, —($C_1$-$C_6$)alkyl, or —($C_3$-$C_6$)cycloalkyl;

$R^3$ and $R^4$ are each independently H, $NR^aR^b$, $OR^c$, $SR^d$, —($C_3$-$C_6$)cycloalkyl, or —($C_1$-$C_6$)alkyl; or two $R^3$ taken together form a 6-membered benzo-ring fused to the heterocycle of Formula I; and/or two $R^4$ taken together form a 6-membered benzo-ring fused to the heterocycle of Formula I (i.e., to the heterocycle to which it is attached);

$R^a$ and $R^b$ are each independently H, —($C_1$-$C_6$)alkyl, or —($C_3$-$C_6$)cycloalkyl; or $R^a$ and $R^b$ taken together form a 5-membered or 6-membered heterocycle with the nitrogen moiety of $NR^aR^b$;

$R^c$ and $R^d$ are each independently H, —($C_1$-$C_6$)alkyl, or —($C_3$-$C_6$)cycloalkyl; and p and q are each independently 1, 2 or 3;

wherein each —($C_1$-$C_6$)alkyl is independently unbranched or branched.

In some embodiments, each 6-membered benzo-ring moiety of Formula I is independently substituted with $R^3$ and/or $R^4$ when p and/or q is 3. In additional embodiments, the phosphine compound of Formula II is represented by a phosphine compound of Formula IIA:

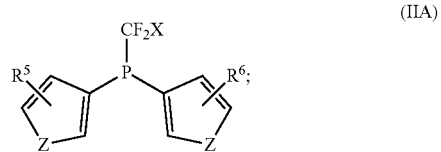

(IIA)

wherein
R[5] and R[6] are each independently H, NR$^a$R$^b$, OR$^c$, SR$^d$, —(C$_3$-C$_6$)cycloalkyl, or —(C$_1$-C$_6$)alkyl; and R$^a$, R$^b$, R$^c$, and R$^d$ are as defined above.

In other additional embodiments, the phosphine compound of Formula II is represented by a phosphine compound of Formula IIB:

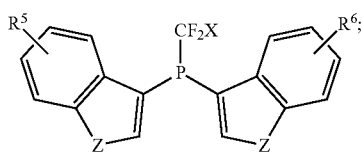
(IIB)

wherein
R[5] and R[6] are each independently H, NR$^a$R$^b$, OR$^c$, SR$^d$, —(C$_3$-C$_6$)cycloalkyl, or —(C$_1$-C$_6$)alkyl; and R$^a$, R$^b$, R$^c$, and R$^d$ are as defined above.

In some embodiments, the phosphine compound of Formula II is represented by a phosphine compound of Formula III-VIII:

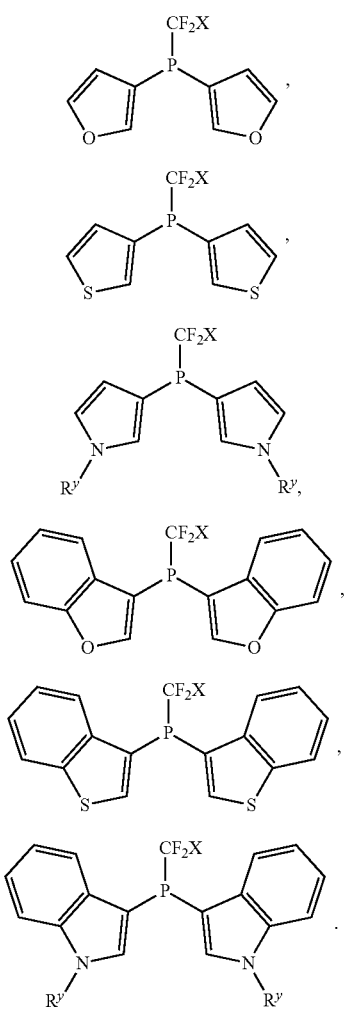

This disclosure also provides a composition comprising any compound disclosed herein, an acid, base, solvent, or combination thereof. Additionally, this disclosure provides a method for fluoroalkylation of an organic compound comprising:

a) contacting a phosphine compound of Formula I:

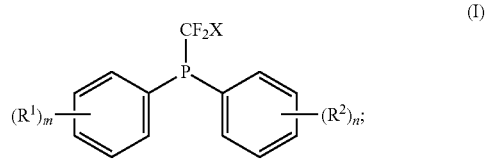
(I)

wherein
X is H, F, or —(C$_1$-C$_6$)perfluoroalkyl;
R[1] and R[2] are each independently NR$^a$R$^b$, OR$^c$, SR$^d$, —(C$_3$-C$_6$)cycloalkyl, or —(C$_1$-C$_6$)alkyl;
R$^a$ and R$^b$ are each independently H, —(C$_1$-C$_6$)alkyl, or —(C$_3$-C$_6$)cycloalkyl; or
R$^a$ and R$^b$ taken together form a 5-membered or 6-membered heterocycle with the nitrogen moiety of NR$^a$R$^b$;
R$^c$ and R$^d$ are each independently H, —(C$_1$-C$_6$)alkyl, or —(C$_3$-C$_6$)cycloalkyl; and m and n are each independently 1 or 2;
wherein each —(C$_1$-C$_6$)alkyl is independently unbranched or branched;
the organic compound, and a solvent under suitable reaction conditions to form a phosphonium salt of the organic compound; and b) contacting the phosphonium salt and an aqueous solution or a mixture of an organic solvent and a base;
wherein a fluoroalkylated organic compound is thereby formed.

In some embodiments, the organic compound is an azine heterocycle. In other embodiments, the azine heterocycle comprises a pyridine, pyrimidine, pyridazine, pyrazine, quinoline, isoquinoline, naphthyridine, or quinazoline. In yet other embodiments, a mixture of the phosphine compound, organic compound and solvent at step a) comprises a Brønsted (or Lewis base) and anhydride. In other embodiments, the anhydride is a sulfonic anhydride. In other embodiments, the sulfonic anhydride is a trifluoromethanelsulfonic anhydride or nonafluorobutanesulfonic anhydride and the like. In some embodiments the Brønsted acid is an organic or inorganic acid. In some embodiments the Brønsted base is an organic or inorganic base.

In additional embodiments, the aqueous solution at step b) comprises a Brønsted acid or Brønsted base. In additional embodiments, the aqueous solution is a neutral solution. In some embodiments, the mixture is a solution of THF and a base. In some embodiments the mixture is anhydrous. In some embodiments, the mixture comprises a trace amount of water wherein the trace amount is less than 5 wt. %, less than 1 wt. %, or less than 0.1 wt. %. In other embodiments, the phosphonium salt is not isolated as a purified intermediate compound before contacting the intermediate with the aqueous solution. In various embodiments the phosphine compound is 1,1'-(((trifluoromethyl) phosphanediyl)bis(4,1-phenylene))dipyrrolidine or (difluoromethyl)bis(4-methoxyphenyl) phosphane.

Also, disclosed herein is a chemical process comprising a phosphine compound disclosed herein, wherein the process is, but not limited to, drug discovery, agrochemical discovery, or chemical manufacturing.

Results and Discussion

We hypothesized that synthesizing fluoroalkyl phosphonium salts and triggering 'contractive' or 'ligand-coupling' processes with oxygen nucleophiles would form C—$CF_2X$ bonds (Scheme 2a). These reactions ostensibly resemble reductive eliminations at late transition metal centers and have been previously leveraged for $Csp^2$-$Csp^2$ bond-formation. However, $Csp^2$-$Csp^3$ coupling via this manifold is virtually unknown. Uchida reported that benzyl Grignard reagents react with tris(2-pyridyl)phosphine oxides to give low yields 2-benzylpyridines (Tetrahedron Lett., 1989, 30, 567). The inaccessibility of the phosphine oxide starting materials, the elevated temperatures employed and the lack of control of ligand-coupling selectivity make this reaction impractical for pyridine alkylation. A lack of mechanistic clarity also potentially explains why no further studies occurred. Recently, a more substantive understanding of $sp^2$-$sp^2$ phosphorus ligand-coupling has emerged, and we reasoned that the apicophilic effects that result in selective pyridine-pyridine coupling were translatable to pyridine fluoroalkylation. We anticipated that water would add to a fluoroalkylphopshonium salt 1 and result in P(V) intermediate 2. A significant lengthening of the apical C—P bond and accumulation of negative charge on the apical ligand preempts ligand-coupling with the pyridinium ring in the equatorial plane. Therefore, fluoroalkyl groups are good candidates for selective coupling due to their ability to stabilize anionic charge on the $sp^3$ carbon by inductive effects. The lowest energy transition state structures calculated for trifluoromethyl and difluoromethyl coupling (3 & 4) suggests these reactions would be facile at ambient temperature. Furthermore, the structures resemble the proposed model for ligand-coupling with the fluoroalkyl group migrating from an apical position. Subsequent elimination of diarylphosphine oxide from Meisenheimer-like intermediate 5 completes the process.

Scheme 2b shows how a series of diarylfluoroalkyl phosphines (7-11) performed in salt-forming reactions using 2-phenylpyridine 6 as a model substrate. Notably, these phosphines are straightforward to prepare on a multigram scale using $TMSCF_3$ as both $CF_3$ and $CF_2H$ sources; two or three steps are required depending on phosphine structure, and the reagents are benchtop stable. Salt formation occurs by sequentially adding the phosphine, $Tf_2O$, and DBU to pyridine 6 and the study clearly shows the yield of the product correlates with the donating capacity of the phosphine's aryl substituents. Salt 12 was not detected using diphenyltrifluoromethylphosphine 7, presumably because the $CF_3$ group reduces its nucleophilicity to the extent that reaction with the N-Tf pyridinium intermediate (not shown) is unproductive. However, introducing electron-donating groups at para-positions of the aryl rings (8-10) overcomes this problem with pyrrolidine substituents (10) proving optimal. We observed a similar trend in $CF_2H$-substituted phosphines, and methoxy substituted analog 11 was most effective at forming salt 13. Notably, the process is exclusively 4-selective and in line with our previous studies on pyridyl phosphonium salt formation.

Scheme 2. Design and optimization of a phosphorus-mediated process for azine fluoroalkylation.

a. Designing a new $sp^2$-$sp^3$ bond-forming process

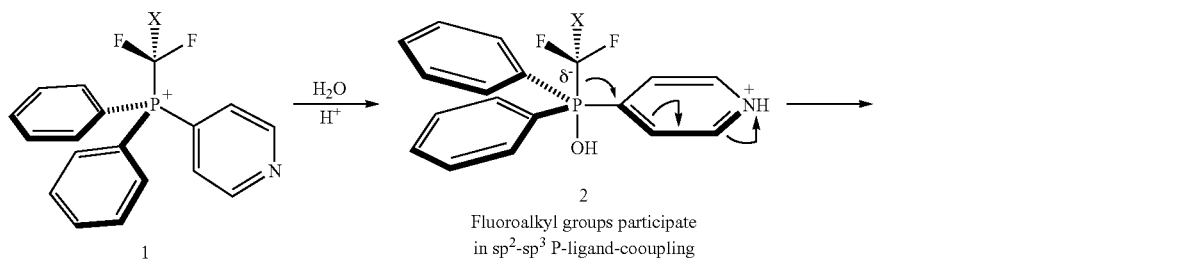

b. Optimizing phosphine nucleophilicity

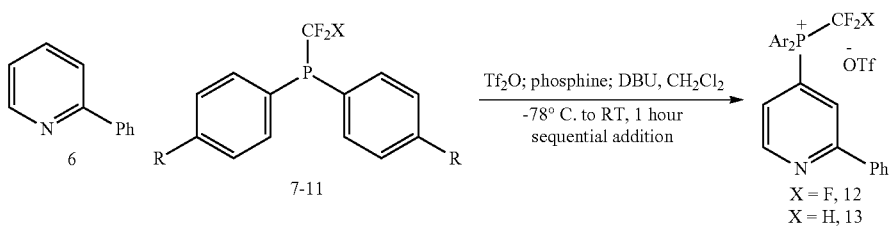

Scheme 2. Design and optimization of a phosphorus-mediated process for azine fluoroalkylation.

| Phosphine | R | X | Salt yield (%)[a] |
|---|---|---|---|
| 7 | H | F | n.d. |
| 8 | OMe | F | 54 |
| 9 | NMe₂ | F | 81 |
| 10 | N-pyrrolidinyl | F | 85 |
| 11 | OMe | H | 86 | c. Fluoroalkylation: optimized conditions

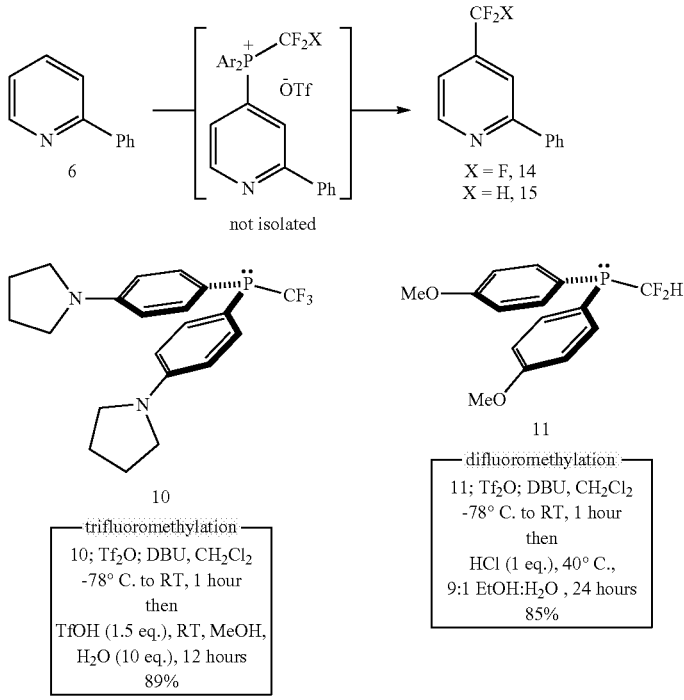

a, Exploiting the apicophilic effect in phosphorus heterobiaryl couplings for $sp^2$-$sp^3$ ligand-coupling,
b, Aryl substitution was used to optimize phosphonium salt formation,
c, A one-pot direct C—H fluoroalkylation reaction.
[a] Yields determined by ¹H NMR using 1,3,5-trimethoxybenzene as an internal standard.
n.d. = not detected.

Scheme 2c shows our optimized conditions where we directly obtained fluoroalkyl derivatives of 6 without isolating the intermediate phosphonium salts. During the study in Scheme 2b, we observed minor amounts of tri- and difluoromethylated pyridine products after washing the crude reaction mixture with water and suspected that the fluoroalkylphosphonium salts were particularly prone to ligand-coupling. We rationalized that after forming salts 12 and 13, adding acid and water would trigger ligand-coupling and enable a one-pot fluoroalkylation process. Previously, in $sp^2$-$sp^2$ coupling, we established that nucleophilic attack of alcohols to phosphonium salts is rate-determining, and the withdrawing effect of the fluoroalkyl groups in 11 and 12 should make this step more facile. Salt formation is complete within one hour using 10 then adding TfOH, methanol, and water directly to the reaction mixture and stirring for 12 hours at room temperature results in good yield of the trifluoromethylated product 14. Removing water from the reaction mixture results in no product indicating its essential role in ligand-coupling. Difluoromethylation (15) follows a similar protocol using 11, except that the ligand-coupling stage occurs at 40° C. reflecting the relative electrophilicity of salts 13 and 14.

We then applied the trifluoromethylation protocol to a series of building block azines (Scheme 3a). Using 10, both 2,2- and 2,3-bipyridines were directly and selectively trifluoromethylated (16 & 17). The reaction is less efficient when a 2-amino substituent is present (18), but 3-phenoxy substituted pyridine 19 formed in high yield. Despite the precedent for amides reacting with Tf₂O, we obtained 20 in moderate yield. A series of 2,5-disubstituted pyridines worked well under this protocol including functional groups such as alkynes, imides, and esters (21-25). Under standard conditions, the 3-position ester in 22b begins to hydrolyze; changing the conditions to NaHCO₃ in THF with 10 equivalents of water alleviates this problem. Under these conditions, we propose that the carbonate nucleophile triggers ligand-coupling without requiring protonation of the pyridine and calculations support the feasibility of this pathway. We did not observe hydrolysis when an ester was in the 2-position and a 2-chloro group was similarly unaffected (23 & 24). A set of 2,3-disubstituted pyridines were successfully trifluoromethylated (26 & 27) as well as 3,5-disubstituted example 28. The reaction also tolerates fused aromatic systems 29-31, and preliminary examples of diazines are promising, including pyridazines and pyrimidines 32 & 33.

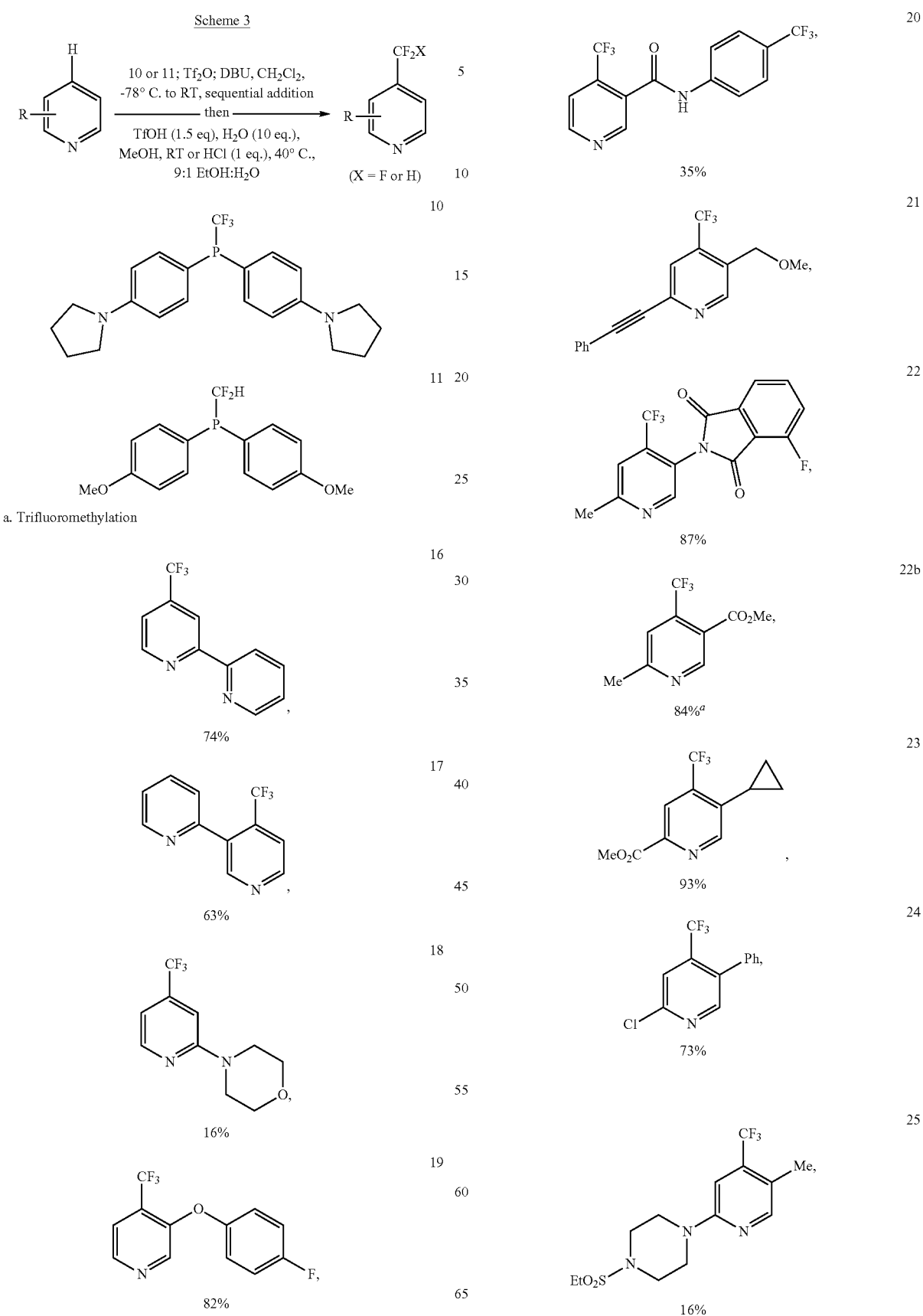

-continued
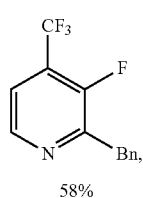
58%
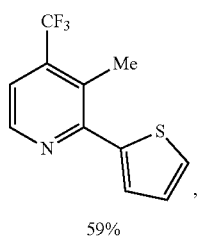
59%
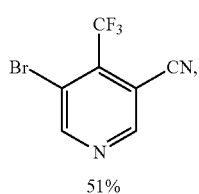
51%
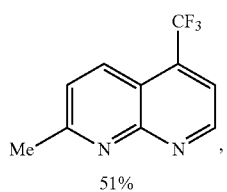
51%
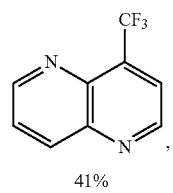
41%
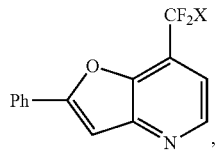
85%
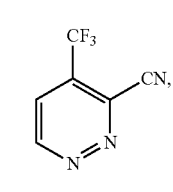
37%
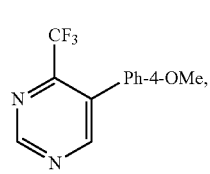
78%
-continued
b. Difluoromethylation
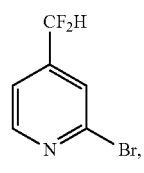
78%[c,d]
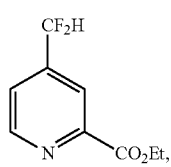
67%
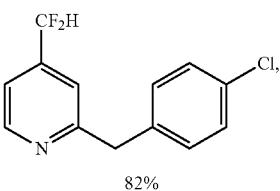
82%
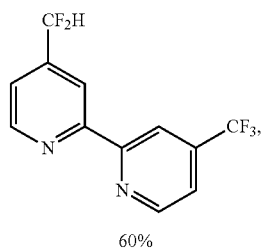
60%
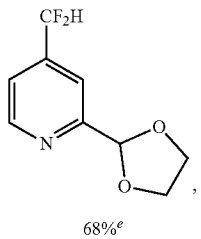
68%[e]
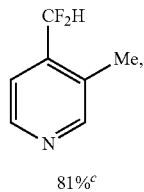
81%[c]
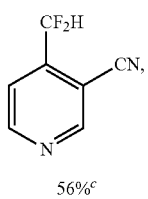
56%[c]

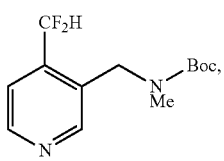

62%

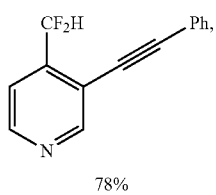

78%

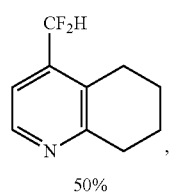

50%

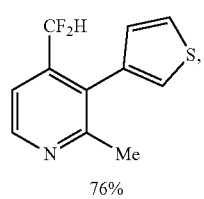

76%

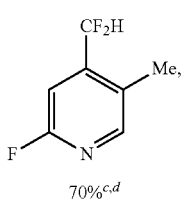

70%[c,d]

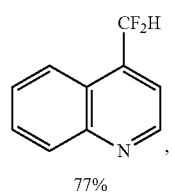

77%

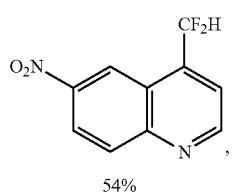

54%

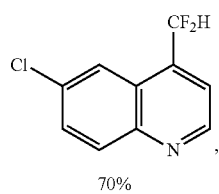

70%

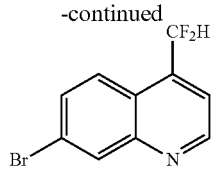

49, X = F, 88%[b]
50, X = H, 81%

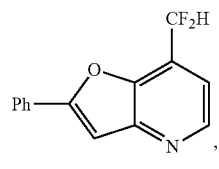

19%

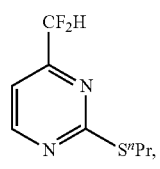

32% a, Scope of building block azines amenable to trifluoromethylation.
b, Difluoromethylation scope. [a]NaHCO$_3$ (3 equiv.), H$_2$O (10 equiv.), THF, RT used for coupling. [b]17:1 regiomeric mixture.
[c]Yield determined by $^1$H NMR using 1,3,5-trimethoxybenzene as an internal standard.
[d]K$_2$CO$_3$ (1 equiv.), H$_2$O/THF 1:1, RT used for coupling. [e]HCl (1 equiv.), TBAF (1 equiv.), 40° C. used for coupling.

[a]NaHCO$_3$ (3 eq.), H$_2$O (10 eq.), THF, rt used for coupling.
[b]17:1 regiomeric mixture.
[c]Yield determined by $^1$H NMR using 1,3,5-trimethoxybenzene as an internal standard.
[d]K$_2$CO$_3$ (1 eq.), H$_2$O/THF 1:1, rt used for coupling.
[e]HCl (1 eq.). TBAF (1 eq.), 40° C., used for coupling.

Scheme 3b shows that a similar set of azines are amenable to difluoromethylation. Notable examples within monosubstituted pyridines include bipyridine 37 that was successively difluoromethylated from 17. Substituents such as 2-Br are compatible (34) but require modified basic reaction media to trigger ligand-coupling. Under acidic conditions, no coupling occurred, and the difluoroalkyl phosphonium salt persisted in the reaction mixture even at 80° C. We hypothesize that the withdrawing effect of the bromo substituent prevents sufficient activation of the pyridine nitrogen atom under acidic conditions, such that the salt is not electrophilic enough to react with water. The reaction tolerates acid-sensitive functional groups such as 2-esters and tert-butoxycarbonyl protected amines (35 & 41). The acetal in 38 partially hydrolyzed under standard conditions but modifying the conditions to a mixture of TBAF and HCl eliminated this pathway; we presume that either ligand-coupling occurs via a P(V) fluorophosphorane, or small amounts of water are present in the TBAF solution that could also promote the reaction. A notable limitation is 3-halopyridines, where we obtained low yields of difluoromethylated products and observed protiodephosphination as the major product. As above, 2,3- and 2,5-disubstituted pyridines are effective (43-45), as are substituted quinolines, a furopyridine, and a pyrimidine (46-52).

Next, we turned our attention to molecules representing drug-like intermediates and lead compounds (Scheme 4a). Such compounds are structurally diverse and contain multiple functional groups that can potentially interfere with the C—P and C—C bond-forming processes. Furthermore, they are generally devoid of preinstalled functional groups for cross-coupling reactions or biases towards selective outcomes for radical-based fluoroalkylation reactions. Forming trifluoromethylated derivatives 53-55 was straightforward despite the presence of multiple Lewis basic atoms and sites of reactivity (Scheme 4a). Quinoline 56 shows that trifluoromethylation occurs at the 2-position when the 4-position is blocked. Phosphines 10 and 11 successfully formed fluoroalkyl pyridines 57-65; the site-selectivity in 57-62 results from selective N-Tf formation of the 3-substituted pyridines over the 2-substituted pyridines during the salt-forming step. We demonstrated that site selectivity can be switched in complex polyazines. We also obtained difluoroalkyl azines 66 and 67 in reasonable yields.

Scheme 4.

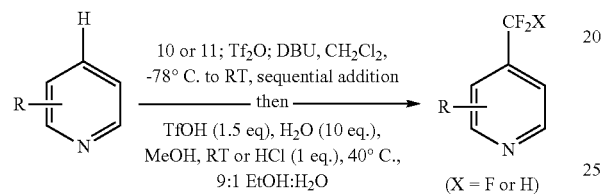

a. Drug-Like Intermediates

53

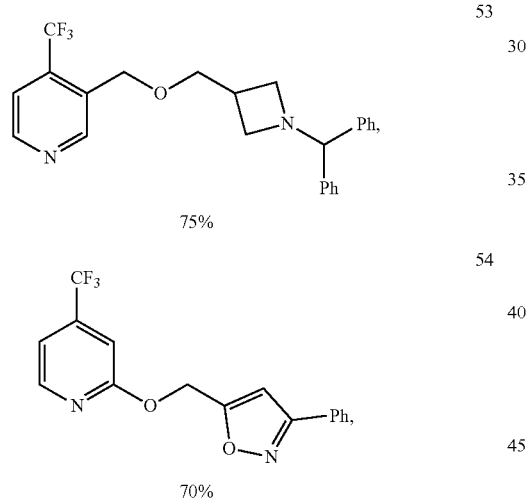

75%

54

70%

55

44%

56

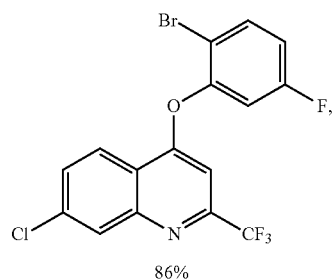

86%

57

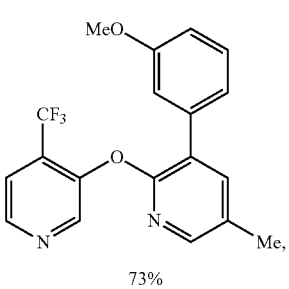

73%

58

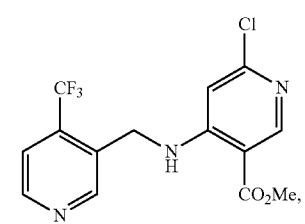

89%

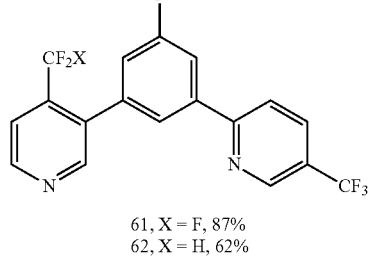

61, X = F, 87%
62, X = H, 62%

63

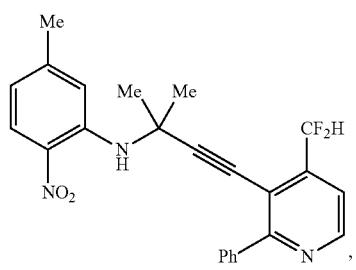

61%

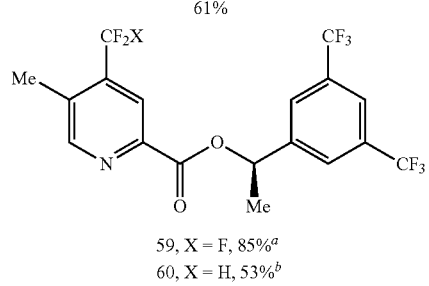

59, X = F, 85%[a]
60, X = H, 53%[b]

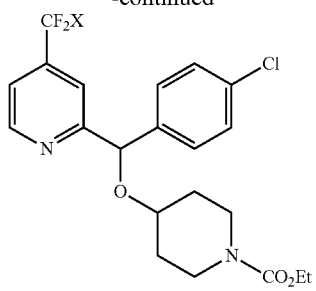
64, X = F, 77%
65, X = H, 61%
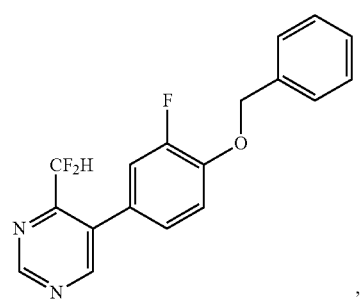
38%
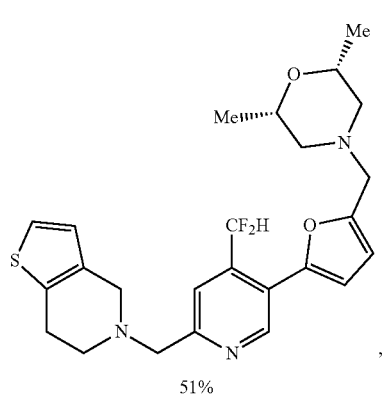
51%
b. Pharmaceuticals
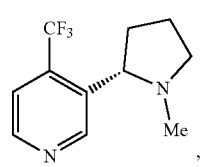
from Nicotine
77%
66
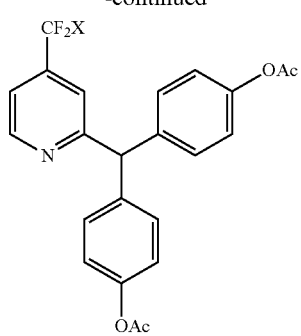
from Bisacodyl
69, X = F, 90%[c]
70, X = H, 83%[b]
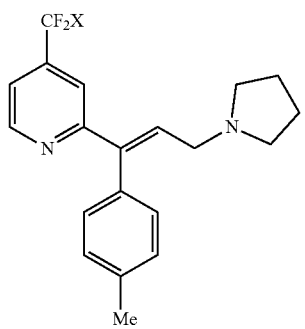
from Triprolidine
71, X = F, 62%[d]
72, X = H, 80%
67
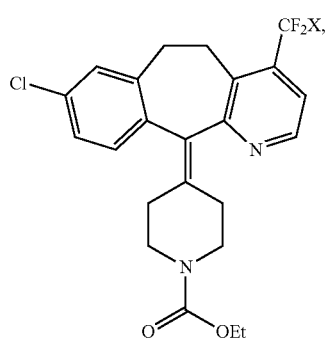
from Loratadine
73, X = F, 83%
74, X = H, 86%
75
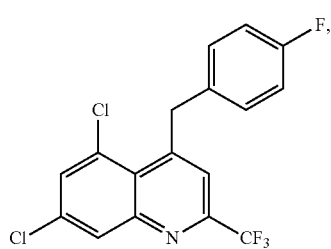
from Quinoxyfen
90%

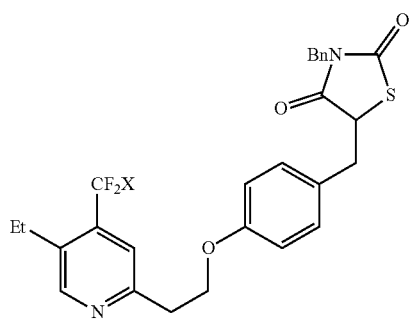

from NBn-Pioglitazone
76, X = F, 42%[c]
77, X = H, 25%

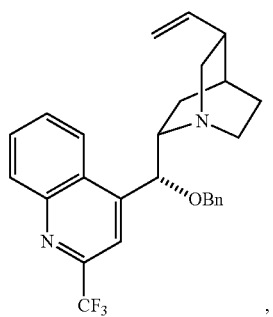

from OBn-cinchonidine
53%

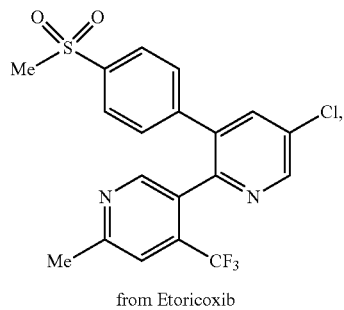

from Etoricoxib
80%

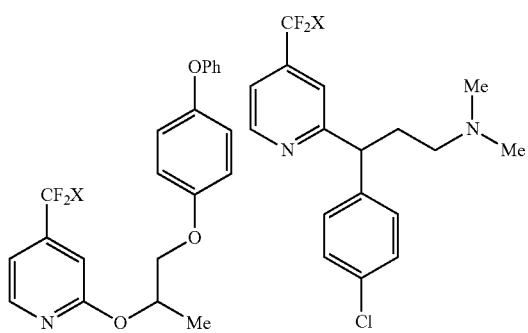

from Pyriproxyfen
80, X = F, 71%
81, X = H, 19%[d]

from Chlorphenamine
82, X = F, 76%[d]
83, X = H, 65%

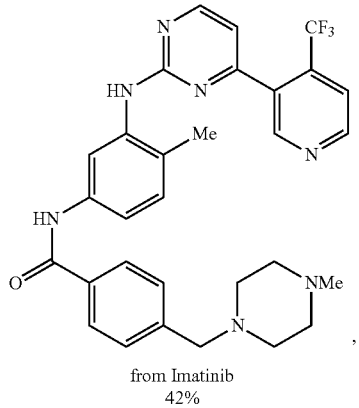

from Imatinib
42%

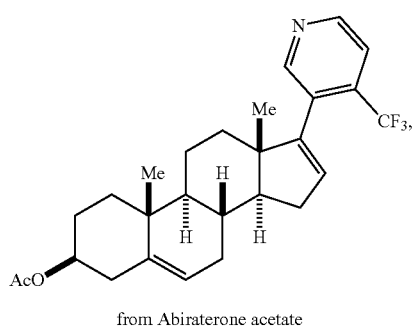

from Abiraterone acetate
55%[a]

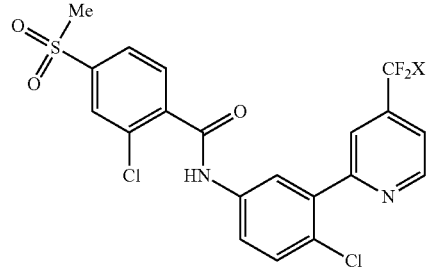

from Vismodegib
86, X = F, 76%
87, X = H, 60% a, Direct fluoroalkylation of complex drug-like intermediates.
b, Late-stage fluoroalkylation of pharmaceuticals.
[a]TfOH (1 equiv.), TBAF (1 equiv.), RT used for coupling.
[b]HCl (1 equiv.), TBAF (1 equiv.), 40° C., used for coupling.
[c]NaHCO3 (3 equiv.), H2O (10 equiv.), THF, RT used for coupling.
[d]K2CO3 (1 equiv.), H2O/THF 1:1, RT used for coupling.
[d]1.0 equiv of TfOH added prior to 10.

Late-stage fluoroalkylation reactions enable medicinal- and agrochemists to rapidly modify advanced candidates and identify compounds with superior pharmacokinetic and pharmacodynamic properties. This strategy avoids the costly and time-consuming recourse to synthesis from simpler precursors. Furthermore, new methods with distinct regioselectivity provide an entry to new drug candidates that were previously inaccessible. In Scheme 4b, we converted twelve different pharmaceuticals and one agrochemical into fluoroalkyl derivatives 68-87 using phosphines 10 and 11. Notably, all products formed as single regioisomers and given the logic reported for predicting the outcome of Minisci-type fluoroalkylation reactions, we assert that this scope and regioselectivity would differ significantly from those radical processes. For example, Baran's sulfinate salts selectively fluoroalkylate nicotine at the 2-position, whereas we obtained 4-position $CF_3$-derivatve 68 using phosphine 10. Comparisons between this phosphine-mediated approach and radical-based fluoroalkylation have been described.

In summary, we have developed a new process for C—H pyridine fluoroalkylation proceeding via phosphorus ligand-coupling reactions. Bench-stable fluoroalkyl phosphines first convert pyridines into phosphonium salts, and then adding an aqueous acidic solution forms the C—$CF_2X$ bond in a one-pot process. Fluorolkyl groups undergo facile ligand-coupling because of their capacity to stabilize anionic charge at the apical positions of P(V) intermediates. This platform reliably fluoroalkylated pyridine building blocks, drug and agrochemical intermediates, and is also a viable method for the late-stage functionalization of complex molecules. The scope of pyridines and the regioselectivity profile is distinct from other common fluoroalkylation methods. We believe this phosphorus-mediated approach will be widely applicable in the pharmaceutical and agrochemical sciences.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. General Methods and Guidelines

Proton nuclear magnetic resonance ($^1$H NMR) spectra were recorded at ambient temperature on a Varian 400 MR spectrometer (400 MHz), an Agilent Inova 400 (400 MHz) spectrometer, an Agilent Inova 500 (500 MHz) spectrometer, or a Bruker AV-111 400 (400 MHz) spectrometer. Chemical shifts (δ) are reported in ppm and quoted to the nearest 0.01 ppm relative to the residual protons in $CDCl_3$ (7.26 ppm), $CD_3OD$ (3.31 ppm) or $(CD_3)_2SO$ (2.05 ppm) and coupling constants (J) are quoted in Hertz (Hz). Data are reported as follows: Chemical shift (multiplicity, coupling constants, number of protons). Coupling constants were quoted to the nearest 0.1 Hz and multiplicity reported according to the following convention: s=singlet, d=doublet, t=triplet, q=quartet, qn=quintet, sext=sextet, sp=septet, m=multiplet, br=broad. Where coincident coupling constants have been observed, the apparent (app) multiplicity of the proton resonance has been reported. Carbon nuclear magnetic resonance ($^{13}$C NMR) spectra were recorded at ambient temperature on a Varian 400 MR spectrometer (100 MHz), an Agilent Inova 400 (100 MHz) spectrometer, an Agilent Inova 500 spectrometer (125 MHz) or a Bruker AV-111 400 (100 MHz) spectrometer. Chemical shift (δ) was measured in ppm and quoted to the nearest 0.01 ppm relative to the residual solvent peaks in $CDCl_3$ (77.16 ppm), $(CD_3)_2SO$ (39.51 ppm), $CD_3OD$ (49.00 ppm) or $CD_3CN$ (1.32 ppm). Low-resolution mass spectra (LRMS) were measured on an Agilent 6310 Quadrupole Mass Spectrometer. High-resolution mass spectra (HRMS) were measured on an Agilent 6224 TOF LC/MS ("QTOF") interfaced to an Agilent 1200 HPLC with multi-mode (combined ESI and APCI) and Direct Analysis in Real Time (DART) sources. (IR) spectra were recorded on a Nicolet IS-50 FT-IR spectrometer as either solids or neat films, either through direct application or deposited in CHCl3, with absorptions reported in wavenumbers ($cm^{-1}$). Analytical thin layer chromatography (TLC) was performed using pre-coated Silicycle glass backed silica gel plates (Silicagel 60 F254). Flash column chromatography was undertaken on Silicycle silica gel Siliaflash P60 40-63 um (230-400 mesh) under a positive pressure of air unless otherwise stated. Visualization was achieved using ultraviolet light (254 nm) and chemical staining with ceric ammonium molybdate or basic potassium permanganate solutions as appropriate. Tetrahydrofuran (THF), toluene, hexane, diethyl ether and dichloromethane were dried and distilled using standard methods. Methanol, 1,2-dichloroethane (DCE), 1,4-dioxane, ethyl acetate, chloroform, and acetone were purchased anhydrous from Sigma Aldrich chemical company. All reagents were purchased at the highest commercial quality and used without further purification. Reactions were carried out under an atmosphere of nitrogen unless otherwise stated. All reactions were monitored by TLC, $^1$H NMR spectra taken from reaction samples, and liquid chromatography mass spectrometry (LCMS) using an Agilent 6310 Quadrupole Mass Spectrometer for MS analysis. Melting points (m.p.) were recorded using a Büchi B-450 melting point apparatus and are reported uncorrected. $Tf_2O$ (99%) was purchased from Oakwood Chemical and used without further purification but was routinely stored in a −20° C. fridge. DBU was distilled before use. 200 proof ethanol was purchased from PHARMCO-AAPER and used without further purification. HCl (4.0 M in dioxanes) and trifluoromethanesulfonic acid (98%) were purchased from Sigma Aldrich chemical company and used without further purification but were routinely stored in a −20° C. fridge.

TABLE 1

Optimization of salt formation for trifluoromethylphosphine.

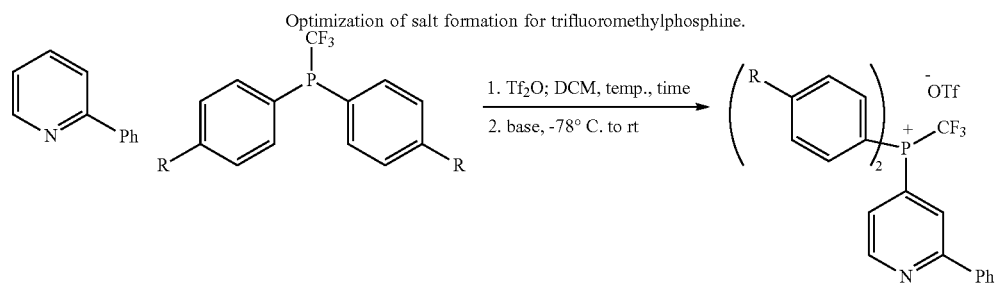

| entry | R | temp (° C.) | time (min) | base | T.M. yield$^a$ |
|---|---|---|---|---|---|
| 1 | H | −78 | 30 | DBU | n.d. |
| 2 | OMe | −78 | 30 | DBU | 54 |
| 3 | $NMe_2$ | −78 | 30 | DBU | 81 |
| 4 | N-pyrrolidinyl | −30 | 30 | DBU | 76 |

TABLE 1-continued

Optimization of salt formation for trifluoromethylphosphine.

| entry | R | temp (° C.) | time (min) | base | T.M. yield[a] |
|---|---|---|---|---|---|
| 5 | N-pyrrolidinyl | −50 | 30 | DBU | 81 |
| 6 | N-pyrrolidinyl | −78 | 30 | DBU | 85 |

[a]Yields were determined by $^1$H NMR using 1,3,5-trimethoxybenzene as an internal standard.

TABLE 2

Optimization of acid-promoted trifluoromethylation of heterocycles.

| entry | HOTf (eq) | solvent | time (h) | T.M. yield[a] |
|---|---|---|---|---|
| 1 | 1 | MeOH/H$_2$O = 1/1 | 18 | 76% |
| 2 | 1 | MeOH/H$_2$O = 4/1 | 18 | 79% |
| 3 | 1 | MeOH/H$_2$O = 9/1 | 18 | 71% |
| 4 | 1 | MeOH (0.5 ml), H$_2$O (10 eq) | 18 | 80% |
| 5 | 1.5 | MeOH (0.5 ml), H$_2$O (10 eq) | 12 | 84% |
| 6 | 2 | MeOH (0.5 ml), H$_2$O (10 eq) | 12 | 81% |
| 7 | 1.5 | MeOH (1.0 ml), H$_2$O (10 eq) | 12 | 85% |
| 8 | 1.5 | MeOH (0.25 ml), H$_2$O (10 eq) | 12 | 82% |
| 9 | 1.5 | THF (0.5 ml), H$_2$O (10 eq) | 12 | 79% |
| 10 | 1.5 | EtOH (0.5 ml), H$_2$O (10 eq) | 12 | 80% |
| 11 | 1.5 | IPA (0.5 ml), H$_2$O (10 eq) | 12 | 75% |
| 12 | 1.5 | TFE (0.5 ml), H$_2$O (10 eq) | 12 | — |
| 13 | 0 | MeOH (0.5 ml), H$_2$O (10 eq) | 24 | 77% |

[a]Yields were determined by $^1$H NMR using 1,3,5-trimethoxybenzene as an internal standard.

TABLE 3

Optimization of base-promoted trifluoromethylation of heterocycles.

| entry | Base (eq) | solvent | time (h) | T.M. yield[a] |
|---|---|---|---|---|
| 1 | NaOMe (3) | MeOH | 30 min | 0% |
| 2 | NaOMe (3) | THF | 30 min | 12% |
| 3 | NaHCO$_3$ (3) | THF | 24 h | 73% |
| 4 | Na$_2$CO$_3$ (3) | THF | 24 h | 13% |
| 5 | NaO$^t$Bu (3) | THF | 30 min | 0% |
| 6 | NaHCO$_3$ (3) | CH$_3$CN | 20 h | 57% |

TABLE 3-continued

Optimization of base-promoted trifluoromethylation of heterocycles.

| entry | Base (eq) | solvent | time (h) | T.M. yield[a] |
|---|---|---|---|---|
| 7 | NaHCO$_3$ (3) | DMF | 20 h | 0% |
| 8 | NaHCO$_3$ (3) | THF (0.5 ml), H$_2$O(10 eq) | 30 min | 78% |

[a]Yields were determined by $^1$H NMR using 1,3,5-trimethoxybenzene as an internal standard.

TABLE 4

Optimization of salt formation for difluoromethylphosphine.

| entry | R | temp (° C.) | time (min) | base | % yield[a] |
|---|---|---|---|---|---|
| 1 | H | −50 | 60 | DBU | 65 |
| 2 | OMe | −50 | 60 | DBU | 68 |
| 3 | Me | −50 | 60 | DBU | 83 |
| 4 | Me | −30 | 60 | DBU | 66 |
| 5 | Me | −78 | 60 | DBU | 84 |
| 6 | Me | −78 | 30 | DBU | 85 |
| 7 | Me | −78 | 15 | DBU | 79 |
| 8 | Me | −78 | 30 | NEt$_3$ | 79 |
| 9 | Me | −78 | 30 | TBD | 51 |
| 10 | Me | −78 | 30 | MTBD | 82 |
| 11 | Me | −78 | 30 | TMG | 70 |
| 12 | OMe | −78 | 30 | DBU | 90 |

[a]Yields were determined by $^1$H NMR using 1,3,5-trimethoxybenzene as an internal standard.

TABLE 5

Optimization of difluoromethylation reaction.

| entry | nucleophile | temp (° C.) | solvent | time | % yield[a] |
|---|---|---|---|---|---|
| 1 | MeOH | RT | MeOH | >48 h | — |
| 2 | MeOH | 40 | MeOH | >48 h | — |
| 3 | H$_2$O | RT | MeOH | >48 h | — |
| 4 | H$_2$O | 40 | MeOH | −36 h | 79 |
| 5 | H$_2$O | 40 | EtOH | −24 h | 81 |
| 6 | H$_2$O | 40 | THF | −24 h | 79 |
| 7 | H$_2$O | 40 | iPrOH | −24 h | 80 |
| 8 | CsF | RT | THF | >48 h | — |
| 9 | TBAF | 40 | THF | −14 h | 75 |

TABLE 5-continued

Optimization of difluoromethylation reaction.

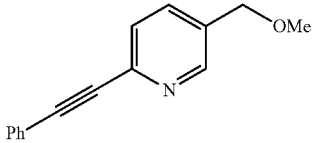 [SMILES: COCc1ccc(C#Cc2ccccc2)nc1]

1. Tf$_2$O; CH$_2$Cl$_2$, -78° C.
2. DBU, -78° C. to rt
3. H$^+$, nucleophile, solvent, temp

| entry | nucleophile | temp (° C.) | solvent | time | % yield[a] |
|---|---|---|---|---|---|
| 10 | TBAF | RT | THF | ~14 h | 61 |
| 11 | K$_2$CO$_3$[b] | RT | H$_2$O/THF | ~15 min | 64 |
| 12 | NaHCO$_3$[b] | RT | H$_2$O/THF | ~15 min | 43 |

[a]Yields were determined by $^1$H NMR using 1,3,5-trimethoxybenzene as an internal standard.
[b]Indicates 5 the reaction was carried out in the absence of acid.

TABLE 6

Reaction Guidelines.

Trifluoromethylation and Difluoromethylation

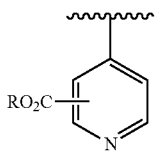

TBAF conditions should be used for functional groups sensitive to solvolysis

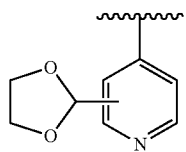

Alternatively, NaHCO$_3$ and K$_2$CO$_3$ conditions can also be used

Specific to Trifluoromethylation

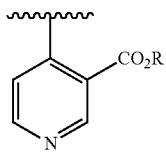

Hydrolysis under TfOH conditions
Using K$_2$CO$_3$ conditions resolves this issue Specific to Difluoromethylation

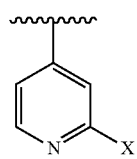

X = F, Cl, Br, I
Slow/No reaction under HCl conditions
Using K$_2$CO$_3$ conditions resolves this issue Example 2. Preparation of Heterocyclic Precursors

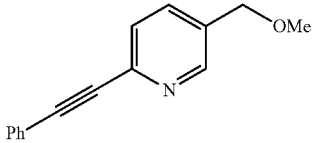 [SMILES: COCc1ccc(C#Cc2ccccc2)nc1]

5-(Methoxymethyl)-2-(phenylethynyl)pyridine. A 100 mL flask equipped with a magnetic stirring bar was charged with PdCl$_2$(PPh$_3$)$_2$ (140 mg, 0.20 mmol) and CuI (76 mg, 0.40 mmol) dissolved in diisopropylamine (20 mL) and N,N-dimethylformamide (15 mL). The resultant solution was stirred under nitrogen at room temperature for 10 minutes before adding 2-bromo-5-(methoxymethyl)pyridine (2.02 g, 10.00 mmol) in diisopropylamine (10 mL) and phenylacetylene (1.22 g, 12.00 mmol). Then, stirring was continued at room temperature for an additional hour. After this time, the reaction mixture was diluted with EtOAc and washed with a saturated NH$_4$Cl solution and with brine. The organic layer was separated, dried over Na$_2$SO$_4$, filtered, and concentrated under reduced pressure. The residue was purified by flash chromatography (silica gel: 33% EtOAc in hexanes) to provide the title compound as a light brown oil (2.12 g, 9.50 mmol, 95% yield). $^1$H NMR (400 MHz, CDCl$_3$) δ: 8.58 (d, J=2.2 Hz, 1H), 7.69 (dd, J=2.2, 8.0 Hz, 1H), 7.62-7.59 (m, 2H), 7.53 (d, J=8.0 Hz, 1H), 7.40-7.33 (m, 3H), 4.50 (s, 3H), 3.43 (s, 3H); $^{13}$C NMR (100 MHz, CDCl$_3$) δ: 149.33, 142.74, 135.60, 133.05, 132.12, 129.06, 128.47, 126.93, 122.32, 89.38, 88.58, 71.87, 58.52; IR ν$_{max}$/cm$^{-1}$ (film): 3055, 2986, 2926, 2892, 2817, 2220, 1725, 1590, 1559, 1491, 1470, 1442, 1394, 1356, 1314, 1279, 1191, 1153, 1098, 1024, 966, 914, 863, 839, 755, 689; m/z HRMS (DART): [M+H]$^+$ calculated for C$_{15}$H$_{14}$NO$^+$=224.1070, found 224.1079.

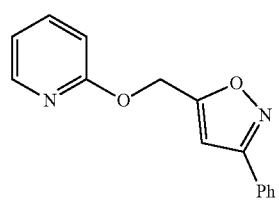 [SMILES: c1ccc(-c2cc(COc3ccccn3)on2)cc1]

3-Phenyl-5-((pyridin-2-yloxy)methyl)isoxazole. (3-Phenylisoxazol-5-yl) methanol (1.75 g, 10.00 mmol) was added portions under $N_2$ to a suspension of NaH (60%) (480 mg, 12.00 mmol) in anhydrous DMF (25 mL). After stirring at rt for 30 min, 2-fluoropyridine (1.03 mL, 12.00 mmol) was added dropwise and the mixture was stirred at room temperature overnight. The reaction mixture was quenched with cold $H_2O$ and extracted with EtOAc (3×50 mL). The organic extracts were washed with $H_2O$ (3×100 mL), dried over anhydrous $Na_2SO_4$, filtered and concentrated in vacuo. The crude material was purified by flash chromatography (silica gel: 17% EtOAc in hexanes) to provide the title compound as a yellow oil (2.26 g, 8.90 mmol, 89% yield). $^1$H NMR (400 MHz, CDCl$_3$) δ: 8.18 (dd, J=1.6, 5.1 Hz, 1H), 7.82-7.79 (m, 2H), 7.64-7.60 (m, 2H), 7.48-7.43 (m, 3H), 6.95-6.92 (m, 1H), 6.84 (d, J=8.4 Hz, 1H), 6.64 (s, 1H), 5.54 (s, 2H); $^{13}$C NMR (100 MHz, CDCl$_3$) δ: 169.15, 162.61, 162.55, 146.85, 139.14, 130.14, 129.12, 129.03, 126.99, 117.80, 111.38, 101.67, 58.30; IR $v_{max}$/cm$^{-1}$ (film): 3128, 3059, 2961, 1611, 1600, 1573, 1469, 1433, 1422, 1403, 1365, 1309, 1284, 1263, 1249, 1221, 1167, 1140, 1044, 1014, 993, 946, 910, 826, 772, 759, 738, 731, 689, 678; m/z HRMS (DART): [M+H]$^+$ calculated for $C_{15}H_{13}N_2O_2^+$=253.0972, found 253.0971.

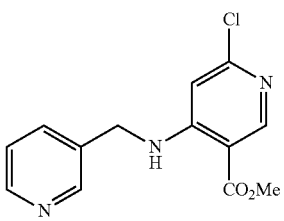 [SMILES: COC(=O)c1cnc(Cl)cc1NCc1cccnc1]

Methyl 6-chloro-4-((pyridin-3-ylmethyl)amino)nicotinate. An oven dried 50 mL flask was charged with pyridin-3-ylmethanamine (611 µL, 6.00 mmol), methyl 4,6-dichloronicotinate (1.03 g, 5.00 mmol), N,N-diisopropylethylamine (2.09 mL, 12.00 mmol) and EtOH (10 mL). The mixture was stirred at reflux for overnight. After cooling to room temperature, the mixture was poured into water (50 mL) and extracted with EtOAc (3×50 mL). The combined organic layer was dried over anhydrous $Na_2SO_4$, filtered and concentrated in vacuo. The crude material was purified by flash chromatography (silica gel: EtOAc) to provide the title compound as a white solid (1.19 g, 3.55 mmol, 71% yield). $^1$H NMR (400 MHz, CDCl$_3$) δ: 8.72 (s, 1H), 8.62-8.57 (m, 3H), 7.66-7.63 (m, 1H), 7.32 (ddd, J=0.9, 4.8, 7.2 Hz, 1H), 6.53 (s, 1H), 4.47 (d, J=5.0 Hz, 2H), 3.90 (s, 3H); $^{13}$C NMR (100 MHz, CDCl$_3$) δ: 168.06, 156.21, 155.84, 153.22, 149.46, 148.86, 134.99, 132.45, 124.04, 107.33, 105.14, 52.20, 44.24; IR $v_{max}$/cm$^{-1}$ (film): 3320, 3070, 3036, 2961, 1687, 1592, 1576, 1565, 1501, 1484, 1465, 1442, 1428, 1408, 1363, 1324, 1297, 1280, 1223, 1191, 1113, 1065, 1026, 928, 842, 791, 712, 607; m/z HRMS (DART): [M+H]$^+$ calculated for $C_{13}H_{13}ClN_3O_2^+$=278.0691, found 278.0704.

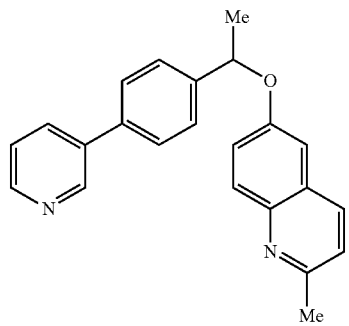 [SMILES: Cc1ccc2cc(OC(C)c3ccc(-c4cccnc4)cc3)ccc2n1]

2-Methyl-6-(1-(4-(pyridin-3-yl)phenyl)ethoxy)quinoline. To a mixture of 1-(4-(pyridin-3-yl)phenyl)ethan-1-ol (598 mg, 3.00 mmol), Et$_3$N (544 µL, 3.30 mmol) and CH$_2$Cl$_2$ (6.6 mL) was added MsCl (256 µL, 3.30 mmol) in one portion at −10° C. for 30 minutes under nitrogen. After the reaction completed, the mixture was poured into cold water (10 mL) and extracted with CH$_2$Cl$_2$ (3×20 mL). The combined organic layer was dried over anhydrous Na$_2$SO$_4$, filtered and concentrated in vacuo to give the product 1-(4-(pyridin-3-yl)phenyl)ethyl methanesulfonate, which was used without further purification. 2-methylquinolin-6-ol (477 mg, 3.00 mmol) was added portions under N$_2$ to a suspension of NaH (60%) (144 mg, 3.60 mmol) in anhydrous DMF (4.5 mL). After stirring at room temperature for 30 min, 1-(4-(pyridin-3-yl)phenyl)ethyl methanesulfonate (prepared accordingly) in anhydrous DMF (4.5 mL) was added dropwise and the mixture was stirred at rt overnight. The reaction mixture was quenched with cold H$_2$O and extracted with EtOAc (3×50 mL). The organic extracts were washed with H$_2$O (3×100 mL), dried over anhydrous Na$_2$SO$_4$, filtered and concentrated in vacuo. The crude material was purified by flash chromatography (silica gel: EtOAc) to provide the title compound as a colorless oil (130 mg, 0.38 mmol, 13% yield over two steps). $^1$H NMR (400 MHz, CDCl$_3$) δ: 8.83 (dd, J=0.8, 2.4 Hz, 1H), 8.58 (dd, J=1.6, 4.8 Hz, 1H), 7.90 (d, J=9.2 Hz, 1H), 7.86-7.81 (m, 2H), 7.58-7.52 (m, 4H), 7.40 (dd, J=2.8, 9.2 Hz, 1H), 7.34 (ddd, J=0.9, 4.8, 8.0 Hz, 1H), 7.18 (d, J=8.4 Hz, 1H), 6.97 (d, J=2.8 Hz, 1H), 5.50 (q, J=6.4 Hz, 1H), 2.67 (s, 3H), 1.74 (d, J=6.4 Hz, 3H); $^{13}$C NMR (100 MHz, CDCl$_3$) δ:156.54, 155.37, 148.59, 148.33, 143.78, 142.94, 137.22, 136.25, 135.25, 134.32, 130.08, 127.60, 127.25, 126.40, 123.64, 122.71, 122.23, 108.58, 76.05, 25.06, 24.53; IR $v_{max}$/cm$^{-1}$ (film): 3029, 2976, 2925, 1621, 1599, 1497, 1476, 1429, 1395, 1376, 1342, 1304, 1266, 1223, 1167, 1112, 1071, 1023, 1000, 967, 940, 897, 832, 802, 710; m/z HRMS (DART): [M+H]$^+$ calculated for $C_{23}H_{21}N_2O^+$=341.1648, found 341.1662.

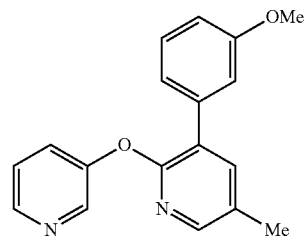 [SMILES: COc1cccc(-c2cc(C)cnc2Oc2cccnc2)c1]

3-(3-Methoxyphenyl)-5-methyl-2-(pyridin-3-yloxy)pyridine. To a mixture of (3-methoxyphenyl)boronic acid (547 mg, 3.60 mmol), 3-bromo-5-methyl-2-(pyridin-3-yloxy)

pyridine (795 mg, 3.00 mmol), Pd(PPh$_3$)$_4$ (173 mg, 0.15 mmol) and Na$_2$CO$_3$ (636 mg, 6.00 mmol) was added a degassed mixture of THF (14.4 mL) and H$_2$O (3.6 mL). The mixture was stirred at 70° C. for 24 hours under nitrogen. After cooling to room temperature, the mixture was poured into water (30 mL) and extracted with EtOAc (3×30 mL). The combined organic layer was dried over anhydrous Na$_2$SO$_4$, filtered and concentrated in vacuo. The crude material was purified by flash chromatography (silica gel: 67% EtOAc in hexanes to 75% EtOAc in hexanes to) to provide the title compound as a colorless oil (778 mg, 2.64 mmol, 88% yield). $^1$H NMR (400 MHz, CDCl$_3$) δ: 8.46 (d, J=2.6 Hz, 1H), 8.40 (dd, J=1.4, 4.7 Hz, 1H), 7.94 (dd, J=0.7, 2.4 Hz, 1H), 7.61 (dd, J=0.7, 2.4 Hz, 1H), 7.47-7.44 (m, 1H), 7.43 (dd, J=2.8, 9.2 Hz, 1H), 7.37 (ddd, J=0.9, 4.8, 8.0 Hz, 1H), 7.20 (d, J=8.4 Hz, 1H), 6.99 (d, J=2.8 Hz, 1H), 5.53 (q, J=6.4 Hz, 1H), 2.69 (s, 3H), 1.76 (d, J=6.4 Hz, 3H); $^{13}$C NMR (100 MHz, CDCl$_3$) δ:156.54, 155.37, 148.59, 148.33, 143.78, 142.94, 137.22, 136.25, 135.25, 134.32, 130.08, 127.60, 127.25, 126.40, 123.64, 122.71, 122.23, 108.58, 76.05, 25.06, 24.53; IR ν$_{max}$/cm$^{-1}$ (film): 3029, 2976, 2925, 1621, 1599, 1497, 1476, 1429, 1395, 1376, 1342, 1304, 1266, 1223, 1167, 1112, 1071, 1023, 1000,967, 940, 897, 832, 802, 710; m/z HRMS (DART): [M+H]$^+$ calculated for C$_{23}$H$_{21}$N$_2$O$^+$=341.1648, found 341.1662.

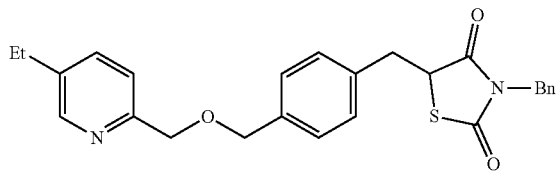 [SMILES: CCc1ccc(COCc2ccc(CC3SC(=O)N(Cc4ccccc4)C3=O)cc2)nc1]

3-benzyl-5-(4-(2-(5-ethylpyridin-2-yl)ethoxy)benzyl)thiazolidine-24-dione. To a mixture of 5-(4-(2-(5-ethylpyridin-2-yl)ethoxy)benzyl)thiazolidine-2,4-dione (535 mg, 1.5 mmol) in DMF (15 mL) was added NaH (60% dispersion in oil) (66 mg, 1.65 mmol) at 0° C. The reaction was warmed to rt over 15 minutes, then benzyl bromide (196 μL, 1.65 mmol) was added. The reaction was stirred at rt for 25 hours and then concentrated in vacuo. The crude material was purified by flash chromatography (silica gel: 100% hexanes to 25% EtOAc in hexanes) to provide the title compound as a light yellow solid (625 mg, 1.40 mmol, 93% yield). m.p. 94-97° C.; $^1$H NMR (400 MHz, CDCl$_3$) δ: 8.42 (d, J=2.2 Hz, 1H), 7.48 (dd, J=7.9, 2.3 Hz, 1H), 7.32-7.23 (m, 4H), 7.21 (d, J=7.9 Hz, 1H), 7.05 (d, J=8.6 Hz, 2H), 6.77 (d, J=8.5 Hz, 2H), 4.79-4.59 (m, 2H), 4.43 (dd, J=8.7, 4.0 Hz, 1H), 4.31 (t, J=6.6 Hz, 2H), 3.38 (dd, J=14.1, 4.0 Hz, 1H), 3.24 (t, J=6.6 Hz, 2H), 3.09 (dd, J=14.1, 8.7 Hz, 1H), 2.64 (q, J=7.6 Hz, 2H), 1.25 (t, J=7.6 Hz, 3H); $^{13}$C NMR (101 MHz, CDCl$_3$) δ: 173.78, 171.03, 158.32, 155.73, 149.02, 137.24, 136.01, 135.09, 130.49, 128.70 (d, J=4.3 Hz), 128.16, 127.45, 123.47, 115.98, 114.83, 67.32, 51.73, 45.22, 37.63 (d, J=1.8Hz), 25.82, 15.44. IR ν$_{max}$/cm$^{-1}$ (film): 3033, 2966, 2931, 2874, 2360, 2342, 1749, 1680, 1611, 1512, 1490, 1430, 1382, 1330, 1247, 1179, 1146, 1029, 908, 730, 700. m/z HRMS (DART): [M+H]$^+$ calculated for C$_{26}$H$_{27}$N$_2$O$_3$S$^+$=447.1737, found 447.1748.

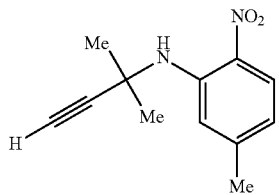 [SMILES: C#CC(C)(C)Nc1cc(C)ccc1[N+](=O)[O-]]

5-methyl-N-(2-methylbut-3-yn-2-yl)-2-nitroaniline. To a mixture of 2-fluoro-4-methyl-1-nitrobenzene (776 mg, 5 mmol) and K$_2$CO$_3$ (1.38 g, 10 mmol) in DMF was added 2-methylbut-3-yn-2-amine (2.63 mL, 25 mmol), and the reaction was heated to 60° C. for 72 hours. After cooling to room temperature, the reaction was poured into water (50 mL) and extracted with EtOAc (3×50 mL). The combined organic layer was washed with brine, dried over anhydrous MgSO$_4$, filtered and concentrated in vacuo. The crude material was purified by flash chromatography (silica gel: 5% CH$_2$Cl$_2$ in hexanes) to provide the title compound as a yellow solid (562 mg, 2.57 mmol, 51% yield). m.p. 104-106° C.; $^1$H NMR (400 MHz, CDCl$_3$) δ: 8.33-8.20 (m, 1H), 8.08 (d, J=8.8 Hz, 1H), 7.34 (dd, J=1.8, 0.9 Hz, 1H), 6.51 (dd, J=8.8, 1.7 Hz, 1H), 2.47 (s, 1H), 2.37 (s, 3H), 1.73 (s, 6H); $^{13}$C NMR (101 MHz, CDCl$_3$) δ:147.01, 143.60, 131.22, 127.03, 117.81, 116.26, 86.22, 71.92, 47.61, 30.51, 22.42. IR ν$_{max}$/cm$^{-1}$ (film): 3331, 3288, 2994, 2979, 2938, 2360, 2342, 1619, 1582, 1486, 1414, 1334, 1276, 1237, 1209, 1177, 1076, 988, 940, 753, 679, 647. m/z HRMS (DART): [M+H]$^+$ calculated for C$_{12}$H$_{15}$N$_2$O$_2$$^+$=219.1128, found 219.1119.

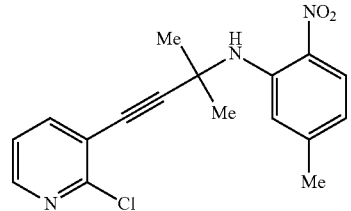 [SMILES: Cc1ccc([N+](=O)[O-])c(NC(C)(C)C#Cc2cccnc2Cl)c1]

N-(4-(2-chloropyridin-3-yl)-2-methylbut-3-yn-2-yl)-5-methyl-2-nitroaniline. To a mixture of 3-bromo-2-chloropyridine (620 mg, 3.22 mmol), CuI (37 mg, 0.193 mmol), PdCl$_2$(PPh$_3$)$_2$ (68 mg, 0.097 mmol) and Et$_3$N (6.5 mL) was added 5-methyl-N-(2-methylbut-3-yn-2-yl)-2-nitroaniline (704 mg, 3.22 mmol). The reaction was heated to 100° C. for 24 hours. After cooling to room temperature, EtOAc (20 mL) and water (20 mL) was added, the organic layer was separated, dried over anhydrous MgSO$_4$, filtered and concentrated in vacuo. The crude material was purified by flash chromatography (silica gel: 20% EtOAc in hexanes) to provide the title compound as a yellow oil (692 mg, 2.10 mmol, 65% yield). $^1$H NMR (400 MHz, CDCl$_3$) δ: 8.36 (s, 1H), 8.30 (dd, J=4.9, 1.8 Hz, 1H), 8.06 (d, J=8.7 Hz, 1H), 7.72 (dd, J=7.7, 2.0 Hz, 1H), 7.49-7.43 (m, 1H), 7.19 (dd, J=7.6, 4.8 Hz, 1H), 6.51 (dd, J=8.7, 1.7 Hz, 1H), 2.36 (s, 3H), 1.83 (s, 6H); $^{13}$C NMR (101 MHz, CDCl$_3$) δ: 152.48, 148.57, 147.11, 143.42, 141.51, 131.20, 126.92, 121.97, 119.95, 117.93, 116.31, 99.29, 78.80, 48.28, 30.32, 22.39. IR ν$_{max}$/cm$^{-1}$ (film): 3352, 2984, 2938, 2360, 2342, 2253, 1618, 1578, 1491, 1394, 1335, 1270, 1236, 1215, 1188, 1079, 908, 754, 730. m/z HRMS (DART): [M+H]$^+$ calculated for C$_{17}$H$_{17}$ClN$_3$O$_2$$^+$=330.1004, found 330.1011.

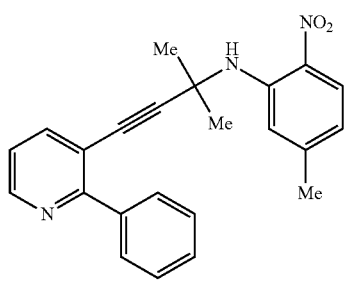 [SMILES: Cc1ccc([N+](=O)[O-])c(NC(C)(C)C#Cc2cccnc2-c2ccccc2)c1]

5-methyl-N-(2-methyl-4-(2-phenylpyridin-3-yl)but-3-yn-2-yl)-2-nitroaniline. To a mixture of N-(4-(2-chloropyridin-3-yl)-2-methylbut-3-yn-2-yl)-5-methyl-2-nitroaniline (241 mg, 0.73 mmol), phenylboronic acid (98 mg, 0.80 mmol), Pd(PPh$_3$)$_4$ (85 mg, 0.073 mmol) and Na$_2$CO$_3$ (164 mg, 1.55 mmol) was added toluene (6 mL) and EtOH (6 mL). The reaction was heated to 110° C. for 24 hours. After cooling to room temperature, the reaction was filtered through celite, EtOAc (20 mL) and water (20 mL) was added, the organic layer was separated, dried over anhydrous MgSO$_4$, filtered and concentrated in vacuo. The crude material was purified by flash chromatography (silica gel: 10% CH$_2$Cl$_2$ in hexanes) to provide the title compound as a yellow oil (252 mg, 0.678 mmol, 93% yield). $^1$H NMR (400 MHz, CDCl$_3$) δ: 8.63 (d, 1H), 8.32 (s, 1H), 8.06 (d, J=8.8 Hz, 1H), 7.88 (dd, J=6.7, 2.9 Hz, 2H), 7.78 (dd, J=7.8, 1.8 Hz, 1H), 7.39-7.29 (m, 3H), 7.21 (dd, J=7.8, 4.8 Hz, 1H), 7.15 (s, 1H), 6.52-6.39 (m, 1H), 2.13 (s, 3H), 1.73 (s, 6H); $^{13}$C NMR (101 MHz, CDCl$_3$) δ: 159.97, 148.89, 146.99, 143.57, 140.99, 139.26, 131.05, 129.21, 129.08, 127.89, 126.93, 121.46, 117.73, 117.32, 116.14, 96.73, 81.84, 48.30, 30.18, 22.29. IR ν$_{max}$/cm$^{-1}$ (film): 3351, 3058, 2980, 2932, 2360, 2342, 1618, 1578, 1490, 1422, 1334, 1265, 1237, 1186, 1077, 743. m/z HRMS (DART): [M+H]$^+$ calculated for C$_{23}$H$_{22}$N$_3$O$_2$$^+$=372.1707, found 372.1719.

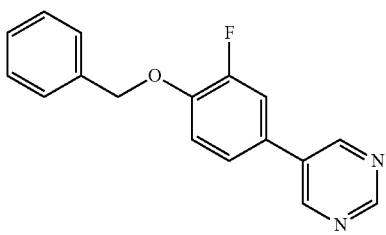 [SMILES: Fc1cc(-c2cncnc2)ccc1OCc1ccccc1]

5-(4-(benzyloxy)-3-fluorophenyl)pyrimidine. To a mixture of 5-bromopyrimidine (795 mg, 5.0 mmol), (4-(benzyloxy)-3-fluorophenyl)boronic acid (1.85 g, 7.5 mmol), Pd/C (10% w/w) (160 mg, 0.15 mmol) and K$_2$CO$_3$ (691 mg, 5.0 mmol) was added EtOH (30 mL) and H$_2$O (10 mL). The reaction was heated to 80° C. for 18 hours. After cooling to room temperature, the reaction was filtered through celite, EtOAc (50 mL) and water (50 mL) was added and extracted with EtOAc (3×50 mL). The combined organic layer was dried over anhydrous MgSO$_4$, filtered and concentrated in vacuo. The crude material was purified by flash chromatography (silica gel: 30% EtOAc in hexanes) to provide the title compound as a white solid (1.135 g, 4.05 mmol, 81% yield). m.p. 103-105° C.; $^1$H NMR (400 MHz, CDCl$_3$) δ: 9.18 (s, 1H), 8.89 (s, 2H), 7.49-7.44 (m, 2H), 7.41 (ddd, J=8.0, 6.9, 1.1 Hz, 2H), 7.38-7.34 (m, 1H), 7.33 (d, J=2.2 Hz, 1H), 7.29-7.24 (m, 2H), 7.13 (t, J=8.4 Hz, 1H), 5.22 (s, 2H); $^{13}$C NMR (101 MHz, CDCl$_3$) δ: 157.54, 154.64, 152.18, 147.67 (d, J=10.7 Hz), 136.17, 133.12 (d, J=1.9 Hz), 128.87, 128.47, 127.70 (d, J=6.8 Hz), 127.55, 122.99 (d, J=3.6 Hz), 116.45 (d, J=2.4 Hz), 114.99 (d, J=19.6 Hz), 71.52; $^{19}$F NMR (377 MHz, CDCl$_3$) δ: −131.81 (dd, J=11.8, 8.4 Hz). IR ν$_{max}$/cm$^{-1}$ (film): 3050, 3035, 2941, 2883, 2578, 2360, 2341, 1618, 1585, 1559, 1522, 1417, 1403, 1389, 1302, 1275, 1257, 1203, 1146, 1052, 1012, 1001, 898, 873, 855, 791, 749, 722, 699, 635, 625. m/z HRMS (DART): [M+H]$^+$ calculated for C$_{17}$H$_{14}$FN$_2$O$^+$=281.1085, found 281.1105.

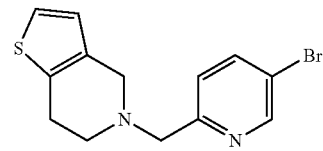 [SMILES: Brc1ccc(CN2CCc3sccc3C2)nc1]

5-((5-bromopyridin-2-yl)methyl)-4,5,6,7-tetrahydrothieno[3,2-c]pyridine. An oven-dried 200 mL round bottom flask was charged with 5-bromopicolinaldehyde (2.68 g, 14.4 mmol), 4,5,6,7-tetrahydrothieno[3,2-c]pyridine (2.20 g, 15.8 mmol), and sodium triacetoxyhydroborate (6.1 g, 28.8 mmol). The flask was subjected to three cycles of vacuum/nitrogen backfill. DCM (72 mL) was added to the reaction flask along with glacial AcOH (1.65 mL). After 19 hours at room temperature, the reaction was quenched with a saturated aqueous solution of NH$_4$Cl (30 mL), diluted with CH$_2$Cl$_2$, and the organic layer was separated. The aqueous layer was basified with a saturated aqueous solution of NaHCO$_3$ and extracted with CH$_2$Cl$_2$ (2×20 mL). The combined organic extracts were dried (MgSO$_4$), filtered and concentrated in vacuo. The crude material was purified by flash chromatography (silica gel: 40% EtOAc in hexanes) to provide the title compound as a white solid (4.17 g, 13.5 mmol, 94% yield). mp 88-89° C.; $^1$H NMR (400 MHz, CDCl$_3$) δ: 8.62 (d, J=2.2 Hz, 1H), 7.79 (dd, J=8.3, 2.4 Hz, 1H), 7.43 (d, J=8.3 Hz, 1H), 7.07 (d, J=5.1 Hz, 1H), 6.69 (d, J=5.1 Hz, 1H), 3.83 (s, 2H), 3.62 (s, 2H), 2.95-2.88 (m, 2H), 2.88-2.83 (m, 2H); $^{13}$C NMR (100 MHz, CDCl$_3$) δ: 157.67, 150.33, 139.28, 133.71, 133.42, 125.30, 124.54, 122.88, 119.22, 63.16, 53.31, 50.98, 25.57. IR ν$_{max}$/cm$^{-1}$ (film): 2962, 2901, 2826, 2771, 2360, 2342, 1573, 1468, 1446, 1376, 1365, 1320, 1171, 1108, 1086, 1001, 982, 843, 703, 652. m/z HRMS (DART): [M+H]$^+$ calculated for C$_{13}$H$_{14}$BrN$_2$S$^+$=309.0056, found 309.0041.

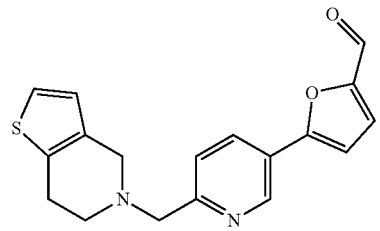 [SMILES: O=Cc1ccc(-c2ccc(CN3CCc4sccc4C3)nc2)o1]

5-(6-((6,7-dihydrothieno[3,2-c]pyridin-5(4H)-yl)methyl)pyridin-3-yl)furan-2-carbaldehyde. An oven dried 200 mL pressure tube was charged with 5-((5-bromopyridin-2-yl)methyl)-4,5,6,7-tetrahydrothieno[3,2-c]pyridine (4.02 g, 13.0 mmol), (5-formylfuran-2-yl)boronic acid (1.65 g, 11.8 mmol), K$_2$CO$_3$ (4.89 g, 35.4 mmol), Pd(OAc)$_2$ (132 mg, 0.59 mmol), triphenylphosphine (619 mg, 2.36 mmol) and subjected to three cycles of vacuum/nitrogen backfill. H$_2$O (43 mL) and dimethoxyethane (41 mL) were charged to the tube. The mixture was heated at 85° C. for 18 hours then diluted with CH₂Cl₂. The organic layer was separated, and the aqueous layer was extracted 2× with CH₂Cl₂. The combined organic layers were dried (MgSO₄), filtered, and concentrated in vacuo. The crude material was purified by flash chromatography (silica gel: 2% MeOH in CH₂Cl₂) to provide the title compound as a slightly impure white solid. Further purification was achieved by dissolving the compound in CH₂Cl₂ and adding an excess of 1M HCl. The aqueous phase was extracted with CH₂Cl₂, separated, and treated with sat. aq. NaHCO₃. The aqueous phase was then extracted with CH₂Cl₂ and the combined organic layers were washed with brine then dried (MgSO₄) and concentrated in vacuo to afford the title compound as pure white solid (1.45 g, 4.5 mmol, 38% yield). $^1$H NMR (400 MHz, CDCl₃) δ: 9.68 (s, 1H), 8.99 (d, J=2.1 Hz, 1H), 8.10 (dd, J=8.2, 2.3 Hz, 1H), 7.64 (d, J=8.2 Hz, 1H), 7.34 (d, J=3.7 Hz, 1H), 7.08 (d, J=5.1 Hz, 1H), 6.92 (d, J=3.7 Hz, 1H), 6.70 (d, J=5.1 Hz, 1H), 3.94 (s, 2H), 3.68 (s, 2H), 3.00-2.83 (m, 4H); $^{13}$C NMR (100 MHz, CDCl₃) δ: 177.43, 160.18, 156.71, 152.67, 146.18, 133.69, 133.42, 133.03, 125.31, 123.96, 123.28, 122.91, 108.62, 63.55, 53.36, 51.04, 25.55. IR $v_{max}$/cm⁻¹ (film): 3109, 2913, 2813, 2360, 2342, 1690, 1600, 1584, 1519, 1467, 1403, 1376, 1357, 1340, 1259, 1019, 965, 797, 768, 754, 700, 637. m/z HRMS (DART): [M+H]⁺ calculated for $C_{18}H_{17}N_2O_2S^+$=325.1005, found 325.1014.

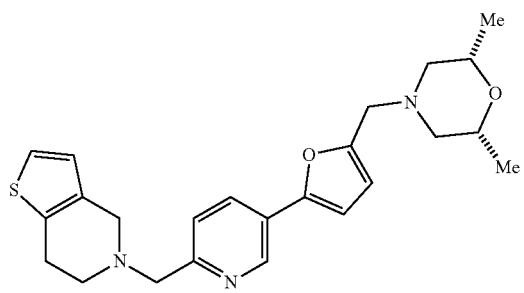 [SMILES: C[C@@H]1CN(Cc2ccc(-c3ccc(CN4CCc5sccc5C4)nc3)o2)C[C@H](C)O1]

5-(6-((6,7-dihydrothieno[3,2-c]pyridin-5(4H)-yl)methyl) pyridin-3-yl)furan-2-carbaldehyde. An oven-dried 100 mL round bottom flask was charged with 5-(6-((6,7-dihydrothieno[3,2-c]pyridin-5(4H)-yl)methyl)pyridin-3-yl)furan-2-carbaldehyde (0.973 g, 3.00 mmol), cis-2,6,-dimethylmorpholine (0.406 mL, 3.30 mmol), and sodium triacetoxyhydroborate (1.27 g, 6.00 mmol). The flask was subjected to three cycles of vacuum/nitrogen backfill. DCM (15 mL) was added to the reaction flask along with glacial AcOH (0.343 mL). After 3 hours stirring at room temperature, the reaction was quenched with a saturated aqueous solution of NH₄Cl (10 mL), diluted with CH₂Cl₂, and the organic layer was separated. The aqueous layer was basified with a saturated aqueous solution of NaHCO₃ and extracted with CH₂Cl₂ (2×10 mL). The combined organic extracts were dried (MgSO₄), filtered and concentrated in vacuo. The crude material was purified by flash chromatography (silica gel, gradient elution: 90% EtOAc in hexanes to 5% MeOH in CH₂Cl₂) to provide the title compound as an amber oil (1.17 g, 2.8 mmol, 92% yield). $^1$H NMR (400 MHz, CDCl₃) δ: 8.85 (d, J=1.9 Hz, 1H), 7.91 (dd, J=8.1, 2.3 Hz, 1H), 7.52 (d, J=8.1 Hz, 1H), 7.07 (d, J=5.1 Hz, 1H), 6.68 (dd, J=10.6, 4.2 Hz, 2H), 6.33 (d, J=3.3 Hz, 1H), 3.89 (s, 2H), 3.71 (ddq, J=12.5, 6.3, 3.1, 1.7 Hz, 2H), 3.63 (d, J=17.5 Hz, 4H), 2.99-2.83 (m, 4H), 2.78 (d, J=10.5 Hz, 2H), 1.86 (t, J=10.8 Hz, 2H), 1.15 (d, J=6.3 Hz, 6H); $^{13}$C NMR (100 MHz, CDCl₃) δ: 157.28, 152.06, 150.82, 144.70, 133.73, 133.34, 131.39, 125.48, 125.21, 122.94, 122.66, 111.19, 106.81, 71.63, 63.52, 58.94, 54.81, 53.20, 50.85, 25.47, 19.15. IR $v_{max}$/cm⁻¹ (film): 2970, 2929, 2811, 2771, 2360, 2342, 1591, 1566, 1477, 1453, 1397, 1374, 1300, 1197, 1141, 1082, 1065, 1018, 981, 837, 788, 733, 700. m/z HRMS (DART): [M+H]⁺ calculated for $C_{24}H_{30}N_3O_2S^+$=424.2053, found 424.2062.

Example 3. Preparation of Phosphines

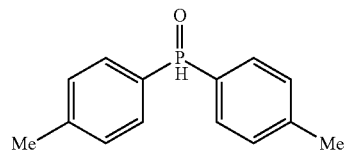

di-p-tolylphosphine oxide. An oven-dried 200 mL round bottom flask was charged with 4-bromotoluene (11.4 g, 66.6 mmol) and 70 mL THF. The resulting solution was added dropwise to a separate oven-dried 200 mL round bottom flask containing magnesium turnings (1.70 g, 70 mmol) at 0° C. Upon completion of the addition, the flask was allowed to warm to room temperature. After stirring for 2 hours at room temperature the mixture was cooled with an ice bath and a solution of diethyl phosphite (2.6 mL, 20 mmol) in 7.0 mL THF was added. The mixture was allowed to warm to room temperature and stirred for two hours. Subsequently 60 mL 0.1N HCl was added drop wise over a period of 5 minutes at 0° C., followed by addition of 60 mL methyl tert-butyl ether (MTBE) and stirring for further 5 minutes. The upper organic phase was decanted from the formed gel. 60 mL CH₂Cl₂ was added to the remaining gel and the mixture agitated well for additional 5 minutes. The resultant mixture was then filtered through a frit equipped with Celite. After washing the Celite with CH₂Cl₂ (2×60 mL) the organic phases were combined, dried over Na₂SO₄ and the solvent was removed in vacuo. The crude product was purified by flash chromatography (silica gel: 90% EtOAc in Hexanes) to give the product di-p-tolylphosphine oxide as a white solid (4.35 g, 18.9 mmol, 94% yield). $^1$H NMR (400 MHz, CDCl₃) δ: 8.63 (d, J=480 Hz, 1H), 7.57 (dd, J=13.5, 7.9 Hz, 4H), 7.29 (dd, J=8.0, 2.7 Hz, 4H), 2.41 (s, 6H); $^{13}$C NMR (101 MHz, CDCl₃) δ:143.04 (d, J=3.2 Hz), 130.70 (d, J=11.9 Hz), 129.56 (d, J=13.4 Hz), 128.32 (d, J=104.0 Hz), 21.64 (d, J=1.6 Hz); $^{31}$P NMR (162 MHz, CDCl₃) δ: 21.53.

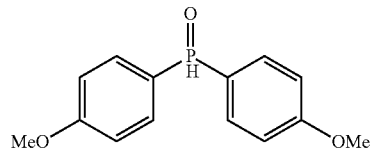

bis(4-methoxyphenyl)phosphine oxide. An oven-dried 200 mL round bottom flask was charged with 4-bromoanisole (8.3 mL, 66.6 mmol) and 70 mL THF. The resulting solution was added dropwise to a separate oven-dried 200 mL round bottom flask containing magnesium turnings (1.70 g, 70 mmol) at 0° C. Upon completion of the addition, the flask was allowed to warm to room temperature. After stirring for 2 hours at room temperature the mixture was cooled with an ice bath and a solution of diethyl phosphite (2.6 mL, 20 mmol) in 7.0 mL THF was added. The mixture was allowed to warm to room temperature and stirred for two hours. Subsequently 60 mL 0.1N HCl was added drop wise over a period of 5 minutes at 0° C., followed by addition of 60 mL methyl tert-butyl ether (MTBE) and stirring for further 5 minutes. The upper organic phase was decanted from the formed gel. 60 mL $CH_2Cl_2$ was added to the remaining gel and the mixture agitated well for additional 5 minutes. The resultant mixture was then filtered through a frit equipped with Celite. After washing the Celite with $CH_2Cl_2$ (2×60 mL) the organic phases were combined, dried over $Na_2SO_4$ and the solvent was removed in vacuo. The crude product was purified by flash chromatography (silica gel: 1% MeOH in EtOAc) to give the product bis(4-methoxyphenyl)phosphine oxide as a white solid (4.72 g, 18.0 mmol, 90% yield). $^1$H NMR (400 MHz, $CDCl_3$) δ: 8.03 (d, J=476 Hz, 1H), 7.61 (dd, J=13.2, 8.6 Hz, 4H), 6.99 (dd, J=8.7, 2.3 Hz, 4H), 3.85 (s, 6H); $^{13}$C NMR (101 MHz, $CDCl_3$) δ:162.88 (d, J=2.8 Hz), 132.63 (d, J=12.9 Hz), 123.01 (d, J=107.9 Hz), 114.43 (d, J=13.9 Hz), 55.36; $^{31}$P NMR (162 MHz, $CDCl_3$) δ: 20.56.

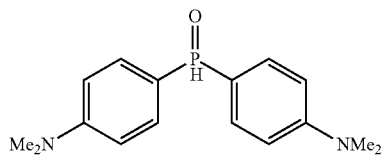

bis(4-(dimethylamino)phenyl)phosphine oxide. An oven-dried 100 mL round bottom flask was charged with 4-bromo-N,N-dimethylaniline (4.00 g, 20.00 mmol) and 20 mL THF. The resulting solution was added dropwise to a separate oven-dried 100 mL round bottom flask containing magnesium turnings (504 mg, 21.00 mmol) at 0° C. After stirring for four hours at room temperature, the mixture was cooled with an ice bath and a solution of diethyl phosphite (773 µL, 6.00 mmol) in 2 mL THF was added. The mixture was allowed to warm to room temperature and stirred for two hours. Subsequently 16 mL 0.1N HCl was added drop wise over a period of 5 minutes at 0° C., followed by addition of 16 mL methyl tert-butyl ether (MTBE) and stirring for further 5 minutes. The upper organic phase was decanted from the formed gel. 20 mL $CH_2Cl_2$ were added to the remaining gel and the mixture agitated well for additional 5 minutes. The resultant mixture was then filtered through a frit equipped with Celite. After washing the Celite with $CH_2Cl_2$ (2×30 mL) the organic phases were combined, dried over $Na_2SO_4$ and the solvent was removed in vacuo. The crude product was purified by flash chromatography (silica gel: EtOAc to 2% MeOH in EtOAc) to give the product bis(4-(dimethylamino)phenyl)phosphine oxide as a white solid (1.38 g, 16.00 mmol, 80% yield). $^1$H NMR (400 MHz, $CDCl_3$) δ: 7.97 (d, J=468 Hz, 1H), 7.50 (dd, J=13.0, 8.8 Hz, 4H), 6.71 (dd, J=8.9, 2.2 Hz, 4H), 3.01 (s, 12H); $^{13}$C NMR (100 MHz, $CDCl_3$) δ:152.64 (d, J=2.4 Hz), 132.21 (d, J=12.6 Hz), 117.18 (d, J=111.9 Hz), 111.41 (d, J=13.4 Hz), 39.96; $^{31}$P NMR (162 MHz, $CDCl_3$) δ: 22.11.

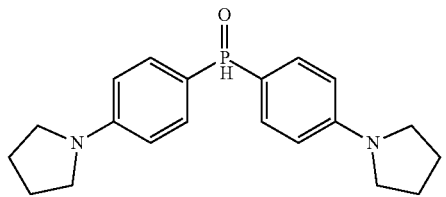

bis(4-(pyrrolidin-1-yl)phenyl)phosphine oxide. An oven-dried 500 mL round bottom flask was charged with 1-(4-bromophenyl)pyrrolidine (31.0 g, 137 mmol) and 140 mL THF. The resulting solution was added dropwise to a separate oven-dried 500 mL round bottom flask containing magnesium turnings (3.51 g, 144 mmol) at 0° C. Upon completion of the addition, the flask was allowed to warm to room temperature. After stirring for 2 hours at room temperature the mixture was cooled with an ice bath and a solution of diethyl phosphite (5.31 mL, 41.2 mmol) in 14.0 mL THF was added. The mixture was allowed to warm to room temperature and stirred for two hours. Subsequently 140 mL 0.1N HCl was added drop wise over a period of 5 minutes at 0° C., followed by addition of 140 mL methyl tert-butyl ether (MTBE) and stirring for further 5 minutes. The upper organic phase was decanted from the formed gel. 140 mL $CH_2Cl_2$ was added to the remaining gel and the mixture agitated well for additional 5 minutes. The resultant mixture was then filtered through a frit equipped with Celite. After washing the Celite with $CH_2Cl_2$ (2×100 mL) the organic phases were combined, dried over $Na_2SO_4$ and the solvent was removed in vacuo. The crude product was purified by flash chromatography (silica gel: 3% MeOH in $CH_2Cl_2$) to give the product bis(4-(pyrrolidin-1-yl)phenyl) phosphine oxide as a white solid (11.9 g, 34.8 mmol, 84% yield). mp 176-178° C.; $^1$H NMR (400 MHz, $CDCl_3$) δ: 7.95 (d, J=468.6 Hz, 1H), 7.48 (dd, J=13.0, 8.7 Hz, 4H), 6.56 (dd, J=8.8, 2.3 Hz, 4H), 3.40-3.20 (m, 8H), 2.11-1.92 (m, 8H); $^{13}$C NMR (101 MHz, $CDCl_3$) δ: 150.27 (d, J=2.3 Hz), 132.50 (d, J=12.9 Hz), 116.72 (d, J=112.6 Hz), 111.45 (d, J=13.6 Hz), 47.57, 25.56; $^{31}$P NMR (162 MHz, $CDCl_3$) δ: −22.61. IR $v_{max}/cm^{-1}$ (film): 2953, 2850, 2270, 1594, 1542, 1482, 1459, 1385, 1283, 1175, 1125, 1003, 961, 927, 802, 708. m/z HRMS (DART): $[M+H]^+$ calculated for $C_{20}H_{26}N_2OP^+$=341.1777, found 341.1769.

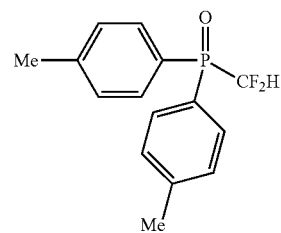 [SMILES: Cc1ccc(P(=O)(c2ccc(C)cc2)C(F)F)cc1]

difluoromethyl)di-p-tolylphosphine oxide. An oven-dried 300 mL round bottom flask was charged with di-p-tolylphosphine oxide (3.45 g, 15 mmol) and $K_2CO_3$ (10.4 g, 75 mmol) and subjected to three cycles of vacuum/nitrogen backfill. $CH_2Cl_2$ (30 mL) and $H_2O$ (90 mL) were added and the mixture was stirred until all solids dissolved. The flask was cooled to 0° C. and a solution of bromodifluoromethyl) trimethylsilane (6.92 mL, 45 mmol) in $CH_2Cl_2$ (15 mL) was added. After being stirred at 0° C. for 16 h, the reaction was quenched by adding water (150 mL), followed by extraction with EtOAc (2×100 mL). The organic layers were combined and dried over anhydrous MgSO$_4$ and filtered. After removal of the solvents in vacuo, the crude material was purified by flash chromatography (silica gel: 50% EtOAc in petroleum ether) to provide the title compound as a white solid (2.92 g, 10.4 mmol, 69% yield). mp 127-128° C.; $^1$H NMR (400 MHz, CDCl$_3$) δ: 7.75 (dd, J=11.6, 8.0 Hz, 4H), 7.35 (dd, J=7.9, 2.5 Hz, 4H), 6.29 (td, J=49.2, 22.0 Hz, 1H), 2.44 (s, 6H); $^{13}$C NMR (100 MHz, CDCl$_3$) δ:144.20 (d, J=2.9 Hz), 132.20 (d, J=10.0 Hz), 129.80 (d, J=12.7 Hz), 123.45 (d, J=104.8 Hz), 115.51 (td, J=266.1, 104.6 Hz), 21.85 (d, J=1.1 Hz); $^{19}$F NMR (376 MHz, CDCl$_3$) δ: −132.25 (dd, J=69.5, 49.2 Hz); $^{31}$P NMR (162 MHz, CDCl$_3$) δ: 23.08 (t, J=69.4 Hz). IR ν$_{max}$/cm$^{-1}$ (film): 3041, 2967, 2360, 2342, 1602, 1384, 1347, 1220, 1200, 1194, 1121, 1080, 1040, 805, 664, 641, 629. m/z HRMS (DART): [M+H]$^+$ calculated for C$_{15}$H$_{16}$F$_2$OP$^+$=281.0901, found 281.0913.

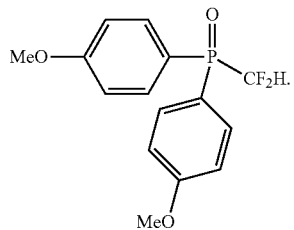 [SMILES: COc1ccc(P(=O)(c2ccc(OC)cc2)C(F)F)cc1]

(difluoromethyl)bis(4-methoxyphenyl)phosphine oxide. An oven-dried round 100 mL round bottom flask was charged with bis(4-methoxyphenyl)phosphine oxide (13.1 g, 50 mmol) and brought into a nitrogen-filled glovebox. LiH (0.48 g, 60 mmol) and LiCl (8.5 g, 200 mmol) were added and the flask was brought out of the glovebox and equipped with a nitrogen line. After cooling to 0° C., the flask was charged with DMF while stirring and allowed to warm to room temperature. After 30 minutes, trifluoromethyltrimethylsilane (30 mL, 200 mmol) was added dropwise at 0° C., and the reaction mixture was allowed to warm to room temperature. After 20 minutes, the solution was cooled to 0° C. and a 1M solution of aqueous K$_2$CO$_3$ was added slowly, and the reaction was allowed to warm to room temperature. After 2 hours, the solution was treated with 60 mL of 1M HCl and extracted (3×) with EtOAc. The combined organic layers were dried over anhydrous MgSO$_4$, filtered, and concentrated in vacuo. The crude material was purified by flash chromatography (silica gel: 25% EtOAc in CH$_2$Cl$_2$) to provide the title compound as white solid (12.3 g, 39.5 mmol, 79% yield). mp 87-89° C.; $^1$H NMR (400 MHz, CDCl$_3$) δ: 7.79 (dd, J=11.1, 8.7 Hz, 4H), 7.04 (dd, J=8.8, 2.2 Hz, 4H), 6.27 (td, J=49.3, 21.9 Hz, 1H), 3.87 (s, 6H); $^{13}$C NMR (100 MHz, CDCl$_3$) δ:163.62 (d, J=2.9 Hz), 134.15 (d, J=10.9 Hz), 117.74 (d, J=109.4 Hz), 115.58 (td, J=265.7, 105.7 Hz), 114.67 (d, J=13.2 Hz); $^{19}$F NMR (376 MHz, CDCl$_3$) δ: −132.26 (dd, J=69.4, 49.3 Hz); $^{31}$P NMR (162 MHz, CDCl$_3$) δ: 22.84 (t, J=69.4 Hz). IR ν$_{max}$/cm$^{-1}$ (film): 3012, 2964, 2845, 2360, 2342, 1594, 1567, 1499, 1458, 1411, 1318, 1294, 1256, 1199, 1185, 1123, 1107, 1081, 1024, 828, 815, 800, 670, 640, 575. m/z HRMS (DART): [M+H]$^+$ calculated for C$_{15}$H$_{16}$F$_2$O$_3$P$^+$=313.0800, found 313.0812.

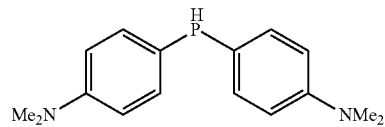

4,4'-phosphanediylbis(N,N-dimethylaniline). A 100 mL flask was equipped with a gas inlet, a bubbler and an addition funnel. The addition funnel was charged with a solution of the bis(4-(dimethylamino)phenyl)phosphine oxide (577 mg, 2.00 mmol) in 4 mL THF. This solution was added over a period of 15 minutes to a 1M solution of DIBAL-H in hexane (6 mL, 6.00 mmol) and stirred for overnight at room temperature (caution: gas evolution). Subsequently 7 mL freshly degased MTBE was added via the addition funnel over ten minutes. After cooling the solution to 0° C., 4 mL 2N aq. NaOH (freshly degassed) was added via the addition funnel over 15 minutes (caution: vigorous gas evolution), followed by 2 mL sat. aq. NaCl over 5 minutes. The solution was stirred for additional 5 minutes and warmed to room temperature. Stirring was subsequently stopped, and the layers allowed to separate. The organic layer was then transferred via cannula to a second 250 mL flask charged with Na$_2$SO$_4$ (4.00 g). After stirring for 10 minutes the mixture was filtered under N$_2$ atmosphere and the solvent removed in vacuo yielding 4,4'-phosphanediylbis(N,N-dimethylaniline) as a white solid (495 mg, 1.82 mmol, 91% yield) (caution: the phosphine is air sensitive and stored in glovebox).

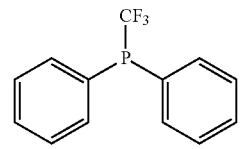 [SMILES: FC(F)(F)P(c1ccccc1)c1ccccc1]

diphenyl(trifluoromethyl)phosphane (7). An oven dried 100 mL round bottom flask was charged with CsF, diethyl ether, and phenoxydiphenylphosphane under nitrogen. Trifluoromethyltrimethylsilane was added and the reaction was stirred for 16 hours at room temperature, then the solvent was removed in vacuo. The crude product was purified by flash chromatography (silica gel: 2% EtOAc in hexanes) to yield the title compound as a pale-yellow oil. $^1$H NMR (400 MHz, CDCl$_3$) δ: 7.47 (t, J=8.2 Hz, 1H), 7.40-7.27 (m, 2H); $^{13}$C NMR (100 MHz, CDCl$_3$) δ: 134.09 (d, J=21.0 Hz), 130.52, 129.54 (dq, J=9.9, 3.2 Hz), 128.90 (d, J=7.9 Hz); $^{31}$P NMR (162 MHz, CDCl$_3$) δ: 2.54 (q, J=73.3 Hz).); $^{19}$F NMR (376 MHz, CDCl$_3$) δ: −55.16 (d, J=73.4 Hz).

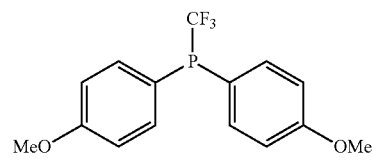 [SMILES: COc1ccc(P(c2ccc(OC)cc2)C(F)(F)F)cc1]

bis(4-methoxyphenyl)(trifluoromethyl)phosphane (8). An oven-dried 300 mL round bottom flask was charged with bis(4-methoxyphenyl)phosphine oxide (5.24 g, 20.0 mmol) and 18-crown-6 (6.34 g, 24.0 mmol) and then subjected to 3 cycles of vacuum/nitrogen backfill. THF (400 mL) was added and the reaction was cooled to 0° C. KH (2.65 g, 24.0 mmol, 36% dispersion in paraffin) was added in one portion, and the reaction was stirred at room temperature for 30 minutes. Trimethyl(trifluoromethyl)silane (12.0 mL, 80.0 mmol) was added dropwise, and the reaction was stirred at room temperature for 10 minutes. The reaction was quenched with water (100 mL) and extracted with EtOAc (3×100 mL). The combined organic layer was dried over anhydrous MgSO$_4$, filtered and concentrated in vacuo. The crude material was purified by flash chromatography (silica gel: 20% CH$_2$Cl$_2$ in hexanes) to provide the title compound as a pale yellow oil (1.34 g, 4.2 mmol, 21% yield). $^1$H NMR (400 MHz, CDCl$_3$) δ: 7.59-7.49 (m, 4H), 7.00-6.92 (m, 4H), 3.84 (s, 6H); $^{13}$C NMR (100 MHz, CDCl$_3$) δ: 161.54, 135.74 (d, J=22.1 Hz), 120.36 (dq, J=6.7, 3.3 Hz), 114.57 (d, J=9.1 Hz), 55.24; $^{31}$P NMR (162 MHz, CDCl$_3$) δ: −0.54 (q, J=73.3 Hz); $^{19}$F NMR (377 MHz, CDCl$_3$) δ: −56.23 (d, J=72.8 Hz).

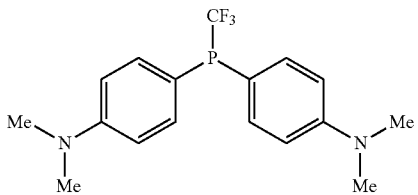 [SMILES: CN(C)c1ccc(P(c2ccc(N(C)C)cc2)C(F)(F)F)cc1]

4,4'-((Trifluoromethyl)phosphanediyl)bis(N,N-dimethylaniline) (9). To a stirred solution of 4,4'-phosphanediylbis(N,N-dimethylaniline) (495 mg, 1.82 mmol) and pyridine (147 μL, 1.82 mmol) in 7.5 mL of DMF was added 2,8-difluoro-S-(trifluoromethyl) dibenzothiophenium triflate (760 mg, 1.73 mmol) under N$_2$ atmosphere. The mixture was stirred at rt for overnight. After the reaction was completed, the mixture was poured into water (20 mL) and extracted with EtOAc (3×50 mL). The combined organic layer was dried over anhydrous Na$_2$SO$_4$, filtered and concentrated in vacuo. The crude material was purified by flash chromatography (silica gel: 5% EtOAc in Hexanes) to give 4,4'-((trifluoromethyl)phosphanediyl) bis(N,N-dimethylaniline) as a white powder (366 mg, 1.07 mmol, 62% yield). mp 79-82° C.; $^1$H NMR (400 MHz, CDCl$_3$) δ: 7.49 (t, J=8.5 Hz, 4H), 6.72 (dd, J=1.2, 9.0 Hz, 4H), 2.99 (s, 12H); $^{13}$C NMR (100 MHz, CDCl$_3$) δ: 151.68, 135.54 (d, J=22.3 Hz), 131.65 (dq, J=33.0, 319.9 Hz), 114.89, 112.21 (d, J=8.8 Hz), 40.11; $^{19}$F NMR (376 MHz, CDCl$_3$) δ: −56.54 (d, J=71.4 Hz); $^{31}$P NMR (162 MHz, CDCl$_3$) δ: −1.02 (q, J=71.3 Hz); IR ν$_{max}$/cm$^{-1}$ (film): 3087, 2895, 2820, 1593, 1544, 1513, 1481, 1443, 1365, 1230, 1199, 1176, 1144, 1100, 1078, 999, 946, 800; m/z HRMS (DART): [M+H]$^+$ calculated for C$_{17}$H$_{21}$F$_3$N$_2$P$^+$=341.1389, found 341.1360.

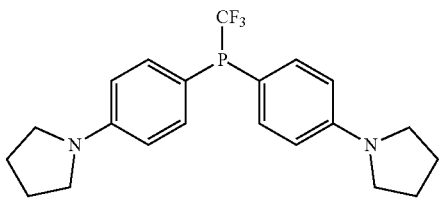 [SMILES: FC(F)(F)P(c1ccc(N2CCCC2)cc1)c1ccc(N2CCCC2)cc1]

1,1'-(((Trifluoromethyl)phosphanediyl)bis(4,1-phenylene)dipyrrolidine (10). An oven-dried 300 mL round bottom flask was charged with bis(4-(pyrrolidin-1-yl)phenyl)phosphine oxide (6.81 g, 20.0 mmol) and 18-crown-6 (6.34 g, 24.0 mmol) and then subjected to 3 cycles of vacuum/nitrogen backfill. THF (136 mL) was added and the reaction was cooled to 0° C. KHMDS (1.0 M in THF) (24 mL, 24.0 mmol) was added dropwise, and the reaction was stirred at room temperature for 30 minutes. Trimethyl(trifluoromethyl)silane (11.82 mL, 80.0 mmol) was added dropwise, and the reaction was stirred at room temperature for 10 minutes. The reaction was quenched with water (100 mL) and extracted with EtOAc (3×100 mL). The combined organic layer was dried over anhydrous MgSO$_4$, filtered and concentrated in vacuo. The crude material was purified by flash chromatography (silica gel: 20% CH$_2$Cl$_2$ in hexanes) to provide the title compound as a peach solid (5.08 g, 12.9 mmol, 65% yield). m.p. 163-165° C.; $^1$H NMR (400 MHz, CDCl$_3$) δ: 7.48 (t, J=8.4 Hz, 4H), 6.58 (d, J=8.3 Hz, 4H), 3.38-3.22 (m, 8H), 2.07-1.94 (m, 8H); $^{13}$C NMR (101 MHz, CDCl$_3$) δ: 149.13, 135.66 (d, J=22.5 Hz), 113.82-113.51 (m), 47.56, 25.62; $^{31}$P NMR (162 MHz, CDCl$_3$) δ: −0.42 (q, J=71.3 Hz); $^{19}$F NMR (376 MHz, CDCl$_3$) δ: −56.83 (d, J=71.4 Hz). IR ν$_{max}$/cm$^{-1}$ (film): 2974, 2847, 1594, 1543, 1511, 1484, 1460, 1381, 1277, 1148, 1100, 1084, 1000, 962, 803, 716, 698. m/z HRMS (DART): [M+H]$^+$ calculated for C$_{21}$H$_{25}$F$_3$N$_2$P$^+$=393.1702, found 393.1702.

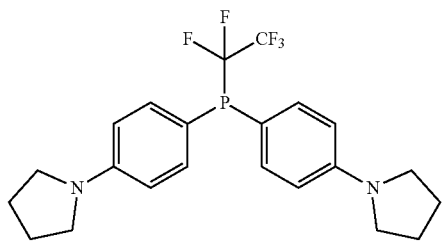 [SMILES: FC(F)(F)C(F)(F)P(c1ccc(N2CCCC2)cc1)c1ccc(N2CCCC2)cc1]

1,1'-(((perfluoroethyl)phosphanediyl)-bis(4,1-phenylene) dipyrrolidine. An oven-dried 300 mL round bottom flask was charged with bis(4-(pyrrolidin-1-yl)phenyl)phosphine oxide (681 mg, 2.0 mmol) and 18-crown-6 (634 mg, 2.4 mmol) and then subjected to 3 cycles of vacuum/nitrogen backfill. THF (13.6 mL) was added and the reaction was cooled to 0° C. KHMDS (1.0 M in THF) (2.4 mL, 2.4 mmol) was added dropwise, and the reaction was stirred at room temperature for 30 minutes. Trimethyl(perfluoroethyl)silane (1.41 mL, 8.0 mmol) was added dropwise, and the reaction was stirred at room temperature for 10 minutes. The reaction was quenched with water (20 mL) and extracted with EtOAc (3×50 mL). The combined organic layer was dried over anhydrous MgSO$_4$, filtered and concentrated in vacuo. The crude material was purified by flash chromatography (silica gel: 20% CH$_2$Cl$_2$ in hexanes) to provide the title compound as a yellow solid (93 mg, 0.210 mmol, 11% yield). m.p. 149-150° C.; $^1$H NMR (400 MHz, CDCl$_3$) δ: 7.59 (t, J=8.6 Hz, 4H), 6.70-6.50 (m, 4H), 3.43-3.22 (m, 8H), 2.09-1.96 (m, 8H); $^{13}$C NMR (101 MHz, CDCl$_3$) δ: 149.23, 136.51 (d, J=24.3 Hz), 122.37-119.90 (m), 119.32-118.33 (m), 112.60 (q, J=4.0 Hz), 111.77 (d, J=9.8 Hz), 47.48, 25.59; $^{31}$P NMR (162 MHz, CDCl$_3$) δ: −4.89 (td, J=56.5, 17.1 Hz); $^{19}$F NMR (377 MHz, CDCl$_3$) δ: −80.51 (dt, J=17.2, 3.4 Hz), −113.74 (dq, J=56.5, 3.4 Hz). IR ν$_{max}$/cm$^{-1}$ (film): 2847, 1593, 1543, 1510, 1484, 1384, 1323, 1279, 1248, 1229, 1187, 1098, 1077, 947, 809, 742, 714, 699. m/z HRMS (DART): [M+H]$^+$ calculated for C$_{22}$H$_{25}$F$_5$N$_2$P$^+$=443.1670, found 443.1689.

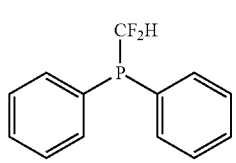 [SMILES: FC(F)P(c1ccccc1)c1ccccc1]

(difluoromethyl)diphenylphosphane. An oven-dried 300 mL round bottom flask was charged with LiBF$_4$ (1.12 g, 12.0 mmol), LiH (95 mg, 12.0 mmol), DMF (50 mL) and then subjected to 3 cycles of vacuum/nitrogen backfill. The reaction was cooled to 0° C., then diphenylphosphane (1.74 mL, 10.0 mmol) was added and the reaction was stirred for 5 minutes. Trimethyl(trifluoromethyl)silane (7.4 mL, 50.0 mmol) was added, and the reaction was stirred at room temperature for 24 hours. TBAF (1 M in THF) (40 mL, 40 mmol) was added, and the reaction was stirred at room temperature for 10 minutes. The reaction was quenched with water (100 mL) and extracted with EtOAc (2×100 mL). The combined organic layer was washed with water (3×200 mL) and brine (200 mL), dried over anhydrous MgSO$_4$, filtered and concentrated in vacuo. The crude material was purified by flash chromatography (silica gel: 100% hexanes) to provide the title compound as a colorless oil (1.075 g, 4.55 mmol, 46% yield). $^1$H NMR (400 MHz, CDCl$_3$) δ: 7.63-7.52 (m, 4H), 7.51-7.39 (m, 6H), 6.55 (td, J=51.7, 14.0 Hz, 1H); $^{13}$C NMR (101 MHz, CDCl$_3$) δ 133.92 (d, J=18.9 Hz), 131.41 (dt, J=10.3, 5.8 Hz), 130.05, 128.95 (d, J=7.1 Hz), 122.35 (td, J=264.7, 12.6 Hz); $^{31}$P NMR (162 MHz, CDCl$_3$) δ: −10.09 (t, J=117.4 Hz); $^{19}$F NMR (376 MHz, CDCl$_3$) δ: −117.40 (dd, J=117.5, 51.7 Hz). IR $\nu_{max}$/cm$^{-1}$ (film): 3075, 3056, 2933, 2360, 2342, 1483, 1435, 1307, 1288, 1064, 1022, 734, 692. m/z HRMS (DART): [M+H]$^+$ calculated for C$_{13}$H$_{12}$F$_2$P$^+$=237.0639, found 237.0638.

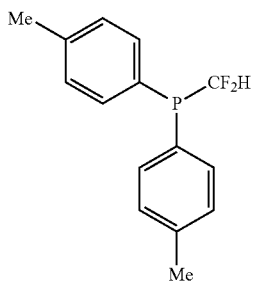 [SMILES: Cc1ccc(P(c2ccc(C)cc2)C(F)F)cc1]

(difluoromethyl)di-p-tolylphosphine. An oven-dried 300 mL round bottom flask was charged with (difluoromethyl)di-p-tolylphosphine oxide (2.80 g, 10 mmol) and subjected to 3 cycles of vacuum/nitrogen backfill. Toluene (120 mL) was added and the flask was cooled to 0° C. Trichlorosilane (4.04 mL, 40 mmol) and TfOH (0.132 mL, 1.5 mmol) were added and the reaction was immediately warmed to 70° C. After 22 h, the reaction was quenched with saturated aqueous sodium carbonate (500 mL) at 0° C. while stirring vigorously. The mixture was allowed to warm to room temperature and filtered through a pad of celite, rinsing liberally with EtOAc. The organic layer was separated and dried with anhydrous MgSO4, filtered, and concentrated in vacuo. The crude material was purified by flash chromatography (silica gel: 10% EtOAc in hexanes) to provide the title compound as a colorless oil (2.28 g, 8.6 mmol, 86% yield). $^1$H NMR (400 MHz, CDCl$_3$) δ: 7.44 (t, J=7.8 Hz, 4H), 7.28-7.21 (m, 4H), 6.49 (td, J=51.9, 13.9 Hz, 1H), 2.40 (s, 6H); $^{13}$C NMR (100 MHz, CDCl$_3$) δ: 140.20, 133.90 (d, J=19.2 Hz), 129.75 (d, J=7.4 Hz), 128.00 (dt, J=8.9, 5.8 Hz), 122.56 (td, J=264.6, 12.7 Hz), 21.48; $^{19}$F NMR (376 MHz, CDCl$_3$) δ: −117.62 (dd, J=117.5, 51.9 Hz); $^{31}$P NMR (162 MHz, CDCl$_3$) δ: −11.58 (t, J=117.5 Hz). IR $\nu_{max}$/cm$^{-1}$ (film): 3073, 3019, 2922, 2866, 2361, 2342, 1599, 1498, 1448, 1398, 1307, 1287, 1188, 1094, 1065, 1019, 804, 627. m/z HRMS (DART): [M+H]$^+$ calculated for C$_{15}$H$_{16}$F$_2$P$^+$=265.0952, found 265.0968.

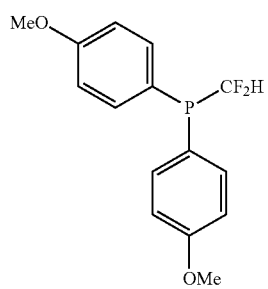

difluoromethyl)bis(4-methoxyphenyl)phosphine (11). An oven-dried 2 L round bottom flask was charged with (difluoromethyl)bis(4-methoxyphenyl)phosphine oxide (20.6 g, 66 mmol) and subjected to 3 cycles of vacuum/nitrogen backfill. Toluene (800 mL) was added and the flask was cooled to 0° C. Trichlorosilane (26.7 mL, 264 mmol) and TfOH (0.874 mL, 9.9 mmol) were added and the reaction was immediately warmed to 70° C. After 22 h, the reaction was quenched with saturated aqueous sodium carbonate (1 L) at 0° C. while stirring vigorously. The mixture was allowed to warm to room temperature and filtered through a pad of celite, rinsing liberally with EtOAc. The organic layer was separated and dried with anhydrous MgSO4, filtered, and concentrated in vacuo. The crude material was purified by flash chromatography (silica gel: 7.5% EtOAc in hexanes) to provide the title compound as a white solid (13.8 g, 46.5 mmol, 70% yield). mp 34-35° C.; $^1$H NMR (400 MHz, CDCl$_3$) δ: 7.46 (tt, J=7.5, 2.3 Hz, 4H), 7.01-6.85 (m, 4H), 6.45 (td, J=51.9, 14.9 Hz, 1H), 3.83 (s, 6H). $^{13}$C NMR (100 MHz, CDCl$_3$) δ: 161.21, 135.48 (d, J=20.6 Hz), 122.59 (td, J=264.8, 13.5 Hz), 122.17 (q, J=6.0 Hz), 114.65 (d, J=8.1 Hz), 55.32; $^{19}$F NMR (376 MHz, CDCl$_3$) δ: −118.06 (dd, J=116.0, 51.9 Hz); $^{31}$P NMR (162 MHz, CDCl$_3$) δ: −12.74 (t, J=116.0 Hz). IR $\nu_{max}$/cm$^{-1}$ (film): 3012, 2969, 2947, 2932, 2840, 2361, 2342, 1590, 1568, 1497, 1281, 1249, 1217, 1186, 1108, 1095, 1066, 1024, 842, 827, 812, 798. m/z HRMS (DART): [M+H]$^+$ calculated for C$_{15}$H$_{16}$F$_2$O$_2$P$^+$=297.0850, found 297.0878.

Example 4. Preparation of Trifluoromethylated Heterocycles

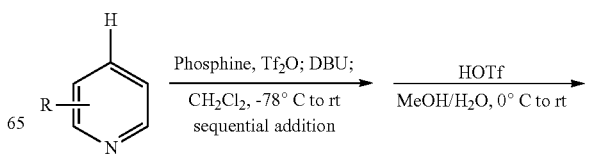

-continued

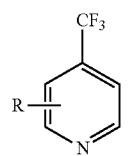

General Procedure A. An oven dried 8 mL vial (<0.30 mmol scale) or a round bottom flask (>0.30 mmol scale) equipped with a stir bar was charged with the heterocycle (1.0 equiv) and 1,1'-(((trifluoromethyl)phosphanediyl)bis(4,1-phenylene))dipyrrolidine (1.1 equiv) and placed under a nitrogen atmosphere. $CH_2Cl_2$ (0.1 M) was added, the reaction vessel cooled to −78° C. and $Tf_2O$ (1.0 equiv) was added dropwise over 5 minutes. The reaction was stirred for 1 hour before DBU (1.0 equiv) was added dropwise via syringe, the cooling bath removed and the reaction warmed to room temperature while stirring (approximately 15-30 minutes). Then, the reaction mixture was cooled to 0° C., HOTf (1.5 equiv), MeOH (0.2 M) and $H_2O$ (10 equiv) were added sequentially. The mixture was warmed to room temperature and stirred for 12 hours. The reaction was quenched with a saturated aqueous solution of $NaHCO_3$ and extracted with $CH_2Cl_2$ (3×). The combined organic extracts were washed with a saturated aqueous solution of brine, dried ($Na_2SO_4$), filtered and concentrated in vacuo. The residue was purified by flash column chromatography under the stated conditions to provide the trifluoromethylated heterocyle.

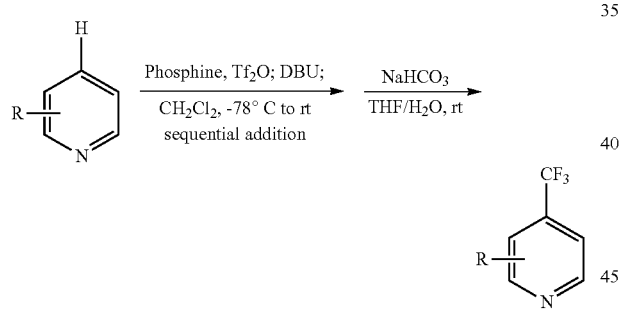

General Procedure B. An oven dried 8 mL vial (<0.30 mmol scale) or a round bottom flask (>0.30 mmol scale) equipped with a stir bar was charged with the heterocycle (1.0 equiv) and 1,1'-(((trifluoromethyl)phosphanediyl)bis(4,1-phenylene))dipyrrolidine (1.1 equiv) and placed under a nitrogen atmosphere. $CH_2Cl_2$ (0.1 M) was added, the reaction vessel cooled to −78° C. and $Tf_2O$ (1.0 equiv) was added dropwise over 5 minutes. The reaction was stirred for 1 hour before DBU (1.0 equiv) was added dropwise via syringe, the cooling bath removed and the reaction warmed to room temperature while stirring (approximately 15-30 minutes). Then, the mixture was stirred for additional 30 minutes after $NaHCO_3$ (3 equiv), THF (0.2 M) and $H_2O$ (10 equiv) were added sequentially. The reaction was quenched with $H_2O$ and extracted with $CH_2Cl_2$ (3×). The combined organic extracts were washed with a saturated aqueous solution of brine, dried ($Na_2SO_4$), filtered and concentrated in vacuo. The residue was purified by flash column chromatography under the stated conditions to provide the trifluoromethylated heterocyle.

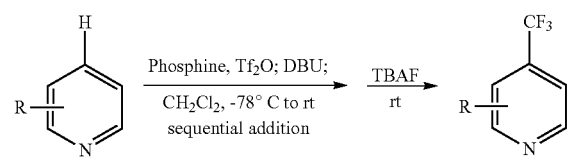

General Procedure C. An oven dried 8 mL vial (<0.30 mmol scale) or a round bottom flask (>0.30 mmol scale) equipped with a stir bar was charged with the heterocycle (1.0 equiv) and 1,1'-(((trifluoromethyl)phosphanediyl)bis(4,1-phenylene))dipyrrolidine (1.1 equiv) and placed under a nitrogen atmosphere. $CH_2Cl_2$ (0.1 M) was added, the reaction vessel cooled to −78° C. and $Tf_2O$ (1.0 equiv) was added dropwise over 5 minutes. The reaction was stirred for 1 hour before DBU (1.0 equiv) was added dropwise via syringe, the cooling bath was removed and the reaction warmed to room temperature while stirring (approximately 15-30 minutes). Then, the reaction mixture was cooled to 0° C., HOTf (1.5 equiv) and TBAF (1M in THF, 1 equiv) were added sequentially. The mixture was warmed to room temperature and stirred for 12 hours. The reaction was quenched with a saturated aqueous solution of $NaHCO_3$ and extracted with $CH_2Cl_2$ (3×). The combined organic extracts were washed with a saturated aqueous solution of brine, dried ($Na_2SO_4$), filtered and concentrated in vacuo. The residue was purified by flash column chromatography under the stated conditions to provide the trifluoromethylated heterocyle.

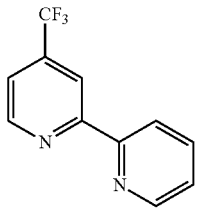 [SMILES: FC(F)(F)c1ccnc(-c2ccccn2)c1]

4-(Trifluoromethyl)-2,2'-bipyridine (16). Prepared according to general procedure A using 2,2'-bipyridine (78 mg, 0.50 mmol), 1,1'-(((trifluoromethyl)phosphanediyl)bis(4,1-phenylene))dipyrrolidine (216 mg, 0.55 mmol), $Tf_2O$ (84 µL, 0.50 mmol), DBU (75 µL, 0.50 mmol), $CH_2Cl_2$ (5 mL), HOTf (111 L, 1.25 mmol), MeOH (2.5 mL) and $H_2O$ (90 µL, 5.00 mmol) at 40° C. for 24 hours. The crude material was purified by flash chromatography (silica gel: 17% EtOAc in hexanes to 33% EtOAc in hexanes) to provide the title compound as a white solid (83 mg, 0.37 mmol, 74% yield). $^1$H NMR (400 MHz, $CDCl_3$) δ: 8.83 (d, J=5.0 Hz, 1H), 8.71-8.68 (m, 2H), 8.44 (td, J=1.2, 7.9 Hz, 1H), 7.84 (dt, J=1.8, 7.7 Hz, 1H), 7.51 (dd, J=1.7, 5.1 Hz, 1H), 7.35 (ddd, J=1.2, 4.8, 7.6 Hz, 1H); $^{13}$C NMR (100 MHz, $CDCl_3$) δ: 157.69, 154.81, 150.16, 149.47, 139.39 (q, J=33.9 Hz), 137.19, 124.60, 123.11 (q, J=271.6 Hz), 121.40, 119.17 (q, J=3.5 Hz), 116.98 (q, J=3.7 Hz); $^{19}$F NMR (376 MHz, $CDCl_3$) δ: −64.78.

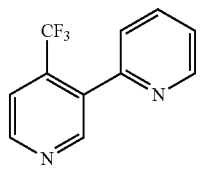 [SMILES: FC(F)(F)c1ccncc1-c1ccccn1]

4'-(Trifluoromethyl)-2,3'-bipyridine (17). Prepared according to general procedure A using 2,3'-bipyridine (78 mg, 0.50 mmol), 1,1'-(((trifluoromethyl)phosphanediyl)bis(4,1-phenylene))dipyrrolidine (216 mg, 0.55 mmol), Tf$_2$O (84 μL, 0.50 mmol), DBU (75 μL, 0.50 mmol), CH$_2$Cl$_2$ (5 mL), HOTf (111 L, 1.25 mmol), MeOH (2.5 mL) and H$_2$O (90 μL, 5.00 mmol) at rt for 24 hours. The crude material was purified by flash chromatography (silica gel: 17% EtOAc in hexanes to 33% EtOAc in hexanes) to provide the title compound as a light yellow oil (83 mg, 0.37 mmol, 74% yield). $^1$H NMR (400 MHz, CDCl$_3$) δ: 8.83-8.81 (m, 2H), 8.72 (td, J=1.4, 4.8 Hz, 1H), 7.79 (dt, J=1.8, 7.8 Hz, 1H), 7.63 (d, J=5.2 Hz, 1H), 7.45 (d, J=7.8 Hz, 1H), 7.38-7.34 (m, 1H); $^{13}$C NMR (100 MHz, CDCl$_3$) δ:154.52, 152.45, 150.27, 149.74, 136.45, 135.81 (q, J=32.3 Hz), 134.18 (q, J=0.9 Hz), 124.34 (q, J=2.2 Hz), 123.27, 122.88 (q, J=273.2 Hz), 119.73 (q, J=4.8 Hz); $^{19}$F NMR (376 MHz, CDCl$_3$) δ: −59.29.

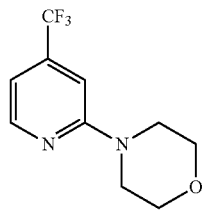 [SMILES: FC(F)(F)c1ccnc(N2CCOCC2)c1]

4-(4-(Trifluoromethyl)pyridin-2-yl)morpholine (18). Prepared according to general procedure A (except that the reaction was done in a pressure tube), using 4-(pyridin-2-yl)morpholine (82 mg, 0.50 mmol), Tf$_2$O (84 μL, 0.50 mmol), 1,1'-(((trifluoromethyl)phosphanediyl)bis(4,1-phenylene))dipyrrolidine (216 mg, 0.55 mmol), DBU (75 μL, 0.50 mmol), CH$_2$Cl$_2$ (5 mL), HOTf (68 μL, 0.77 mmol), MeOH (2.5 mL), and H$_2$O (90 μL, 5.00 mmol) at 60° C. for 12 hours. The crude material was purified by flash chromatography (silica gel: 10% EtOAc in hexanes) to provide the title compound as a colorless oil (19 mg, 0.08 mmol, 16% yield). $^1$H NMR (400 MHz, CDCl$_3$) δ: 8.32 (d, J=5.1 Hz, 1H), 6.82 (d, J=5.2 Hz, 1H), 6.79 (s, 1H), 3.85-3.81 (m, 4H), 3.59-3.55 (m, 4H); $^{13}$C NMR (100 MHz, CDCl$_3$) δ:159.73, 149.37, 139.94 (q, J=32.9 Hz), 123.30 (q, J=273.0 Hz), 108.87 (q, J=3.3 Hz), 102.51 (q, J=4.4 Hz), 66.75, 45.43; $^{19}$F NMR (376 MHz, CDCl$_3$) δ: −65.16, IR ν$_{max}$/cm$^{-1}$ (film): 2925, 1610, 1320, 1040, 957, 761, 667, 531. m/z HRMS (DART): [M+H]$^+$ calculated for C$_{10}$H$_{12}$F$_3$N$_2$O$^+$=233.0902, found 233.0898.

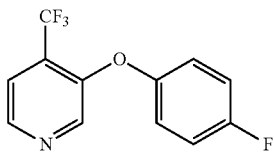 [SMILES: Fc1ccc(Oc2cnccc2C(F)(F)F)cc1]

3-(4-Fluorophenoxy)-4-(trifluoromethyl)pyridine (19). Prepared according to general procedure A using 3-(4-fluorophenoxy)pyridine (95 mg, 0.50 mmol), 1,1'-(((trifluoromethyl)phosphanediyl)bis(4,1-phenylene))dipyrrolidine (216 mg, 0.55 mmol), Tf$_2$O (84 μL, 0.50 mmol), DBU (75 μL, 0.50 mmol), CH$_2$Cl$_2$ (5 mL), HOTf (67 μL, 0.75 mmol), MeOH (2.5 mL) and H$_2$O (90 μL, 5.00 mmol) at 40° C. for 12 hours. The crude material was purified by flash chromatography (silica gel: 17% EtOAc in hexanes) to provide the title compound as a light-yellow oil (106 mg, 0.41 mmol, 82% yield). $^1$H NMR (400 MHz, CDCl$_3$) δ: 8.49 (d, J=5.0 Hz, 1H), 8.29 (s, 1H), 7.55 (d, J=4.9 Hz, 1H), 7.13-7.02 (m, 4H); $^{13}$C NMR (100 MHz, CDCl$_3$) δ: 159.80 (d, J=242.7 Hz), 151.56 (d, J=2.7 Hz), 151.23, 144.49, 141.39, 127.97 (q, J=32.8 Hz), 122.21 (q, J=272.1 Hz), 121.02 (d, J=8.4 Hz), 120.44 (q, J=3.1 Hz), 117.00 (d, J=23.5 Hz); $^{19}$F NMR (376 MHz, CDCl$_3$) δ: −63.66, −117.55; IR ν$_{max}$/cm$^{-1}$ (film): 3047, 1599, 1572, 1501, 1489, 1411, 1322, 1290, 1257, 1218, 1181, 1138, 1090, 1069, 1057, 1011, 881, 832, 823, 769, 732, 649, 617; m/z HRMS (DART): [M+H]$^+$ calculated for C$_{12}$H$_{12}$F$_4$NO$^+$=258.0537, found 258.0551.

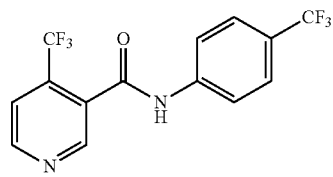 [SMILES: O=C(Nc1ccc(C(F)(F)F)cc1)c1cnccc1C(F)(F)F]

4-(Trifluoromethyl)-N-(4-(trifluoromethyl)phenyl)nicotinamide (20). Prepared according to general procedure A (except that after Tf$_2$O added, the reaction mixture was stirred for 1 hour at −50° C.) using N-(4-(trifluoromethyl)phenyl)nicotinamide (133 mg, 0.50 mmol), 1,1'-(((trifluoromethyl)phosphanediyl)bis(4,1-phenylene))dipyrrolidine (216 mg, 0.55 mmol), Tf$_2$O (84 μL, 0.50 mmol), DBU (75 μL, 0.50 mmol), CH$_2$Cl$_2$ (20 mL), HOTf (67 μL, 0.75 mmol), MeOH (2.5 mL) and H$_2$O (90 μL, 5.00 mmol) at 40° C. for 72 hours. The crude material was purified by flash chromatography (silica gel: 33% EtOAc in hexanes) to provide the title compound as a light-yellow solid (58 mg, 0.18 mmol, 35% yield). mp 167-171° C.; $^1$H NMR (400 MHz, CDCl$_3$) δ: 8.93 (br s, 2H), 7.88 (s, 1H), 7.73 (d, J=8.4 Hz, 2H), 7.66-7.64 (m, 3H); $^{13}$C NMR (100 MHz, d$_6$-Acetone) δ: 164.61, 153.24, 150.29, 143.05, 135.40 (q, J=33.3 Hz), 130.86, 127.11-127.07 (m), 126.40 (q, J=32.3 Hz), 125.35 (q, J=269.1 Hz), 123.64 (q, J=272.4 Hz), 121.08-120.92 (m), 120.72-120.53 (m); $^{19}$F NMR (376 MHz, CDCl$_3$) δ: −61.24, −62.31; IR ν$_{max}$/cm$^{-1}$ (film): 3255, 1649, 1605, 1548, 1413, 1404, 1317, 1289, 1272, 1190, 1141, 1065, 1048, 1019, 898, 841, 703, 658; m/z HRMS (DART): [M+H]$^+$ calculated for C$_{14}$H9F$_6$N$_2$O$^+$=335.0614, found 335.0621.

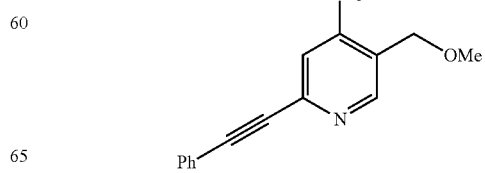

5-(Methoxymethyl)-2-(phenylethynyl)-4-(trifluoromethyl)pyridine (21). Prepared according to general procedure A using 5-(methoxymethyl)-2-(phenylethynyl)pyridine (112 mg, 0.50 mmol), 1,1'-(((trifluoromethyl)phosphanediyl)bis(4,1-phenylene))dipyrrolidine (216 mg, 0.55 mmol), Tf$_2$O (84 μL, 0.50 mmol), DBU (75 μL, 0.50 mmol), CH$_2$Cl$_2$ (5 mL), HOTf (67 μL, 0.75 mmol), MeOH (2.5 mL) and H$_2$O (90 μL, 5.00 mmol) at 40° C. for 20 hours. The crude material was purified by flash chromatography (silica gel: 9% EtOAc in hexanes to 17% EtOAc in hexanes) to provide the title compound as an off-white solid (117 mg, 0.40 mmol, 80% yield). mp 65-68° C.; $^1$H NMR (400 MHz, CDCl$_3$) δ: 8.91 (s, 1H), 7.72 (s, 1H), 7.62-7.60 (m, 2H), 7.42-7.35 (m, 3H), 4.67 (s, 2H), 3.48 (s, 3H); $^{13}$C NMR (100 MHz, CDCl$_3$) δ: 151.37, 143.72, 135.75 (q, J=32.7 Hz), 132.24, 129.95 (q, J=1.6 Hz), 129.51, 128.56, 122.81 (q, J=273.5 Hz), 122.62 (q, J=5.2 Hz), 121.75, 91.04, 87.71, 68.69 (q, J=2.5 Hz), 58.98; $^{19}$F NMR (376 MHz, CDCl$_3$) δ: −62.62; IR ν$_{max}$/cm$^{-1}$ (film): 3064, 2984, 2920, 2888, 2825, 2226, 1600, 1496, 1471, 1458, 1445, 1392, 1299, 1283, 1270, 1204, 1185, 1165, 1136, 1117, 1054, 971, 932, 922, 905, 894, 760, 690, 678; m/z HRMS (DART): [M+H]$^+$ calculated for C$_{16}$H$_{13}$F$_3$NO$^+$=292.0944, found 292.0973.

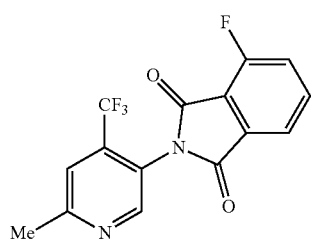 [SMILES: Cc1cc(C(F)(F)F)c(N2C(=O)c3cccc(F)c3C2=O)cn1]

4-Fluoro-2-(6-methyl-4-(trifluoromethyl)pyridin-3-yl)isoindoline-1,3-dione (22). Prepared according to general procedure A (except that after Tf$_2$O added, the reaction mixture was stirred for 1 hour at −50° C.) using 4-fluoro-2-(6-methylpyridin-3-yl)isoindoline-1,3-dione (128 mg, 0.50 mmol), 1,1'-(((trifluoromethyl)phosphanediyl)bis(4,1-phenylene)) dipyrrolidine (216 mg, 0.55 mmol), Tf$_2$O (84 μL, 0.50 mmol), DBU (75 μL, 0.50 mmol), CH$_2$Cl$_2$ (5 mL), HOTf (67 μL, 0.75 mmol), MeOH (2.5 mL) and H$_2$O (90 μL, 5.00 mmol) at rt for 43 hours. The crude material was purified by flash chromatography (silica gel: 33% EtOAc in hexanes to 50% EtOAc in hexanes) to provide the title compound as an off-white solid (141 mg, 0.44 mmol, 87% yield). mp 163-166° C.; $^1$H NMR (400 MHz, CDCl$_3$) δ: 8.52 (s, 1H), 7.86-7.78 (m, 2H), 7.58 (s, 1H), 7.49 (dt, J=1.1, 8.4 Hz, 1H), 2.73 (s, 3H); $^{13}$C NMR (100 MHz, CDCl$_3$) δ: 165.76 (d, J=2.9 Hz), 163.45 (d, J=1.5 Hz), 162.17, 158.05 (d, J=265.7 Hz), 151.58, 137.51 (d, J=7.7 Hz), 137.21 (q, J=32.4 Hz), 133.84 (d, J=1.3 Hz), 123.19 (d, J=19.4 Hz), 122.21 (q, J=2.0 Hz), 121.86 (q, J=273.0 Hz), 120.64 (q, J=4.2 Hz), 120.46 (d, J=3.8 Hz), 117.74 (d, J=12.4 Hz), 24.58; $^{19}$F NMR (376 MHz, CDCl$_3$) δ: −63.14, −110.89; IR ν$_{max}$/cm$^{-1}$ (film): 3501, 3083, 1784, 1724, 1664, 1610, 1495, 1479, 1442, 1391, 1294, 1267, 1251, 1216, 1197, 1169, 1135, 1099, 1062, 1040, 968, 915, 892, 869, 822, 794, 781, 743, 704, 670, 635, 607, 557; m/z HRMS (DART): [M+H]$^+$ calculated for C$_{15}$H$_9$F$_4$N$_2$O$_2$$^+$=325.0595, found 325.062.

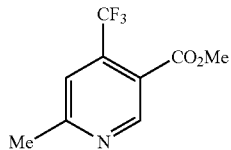

Methyl 6-methyl-4-(trifluoromethyl)nicotinate (23). Prepared according to general procedure B using methyl 6-methylnicotinate (76 mg, 0.50 mmol), 1,1'-(((trifluoromethyl)phosphanediyl)bis(4,1-phenylene))dipyrrolidine (216 mg, 0.55 mmol), Tf$_2$O (84 μL, 0.50 mmol), DBU (75 μL, 0.50 mmol), CH$_2$Cl$_2$ (5 mL), NaHCO$_3$ (126 mg, 1.50 mmol), THF (2.5 mL) and H$_2$O (90 μL, 5.00 mmol) at rt for 30 minutes. The crude material was purified by flash chromatography (silica gel: 33% EtOAc in hexanes) to provide the title compound as a light-yellow solid (92 mg, 0.42 mmol, 84% yield). mp 31-33° C.; $^1$H NMR (400 MHz, CDCl$_3$) δ: 9.00 (s, 1H), 7.49 (s, 1H), 3.96 (s, 3H), 2.69 (s, 3H); $^{13}$C NMR (100 MHz, CDCl$_3$) δ: 165.19, 163.59, 151.53, 137.10 (q, J=34.0 Hz), 122.30 (q, J=1.7 Hz), 122.26 (q, J=272.8 Hz), 119.96 (q, J=5.1 Hz), 53.09, 24.90; $^{19}$F NMR (376 MHz, CDCl$_3$) δ: −61.98; IR ν$_{max}$/cm$^{-1}$ (film): 3453, 3078, 2964, 2858, 1733, 1694, 1602, 1569, 1442, 1384, 1367, 1257, 1232, 1214, 1147, 1125, 1050, 956, 890, 817, 790, 732, 671; m/z HRMS (DART): [M+H]$^+$ calculated for C$_9$H$_9$F$_3$NO$_2$$^+$=220.0580, found 220.0587.

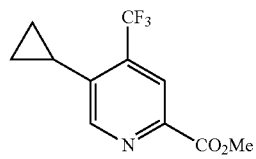 [SMILES: COC(=O)c1cc(C(F)(F)F)c(C2CC2)cn1]

Methyl 5-cyclopropyl-4-(trifluoromethyl)picolinate (24). Prepare according to general procedure A using methyl 5-cyclopropylpicolinate (89 mg, 0.50 mmol), 1,1'-(((trifluoromethyl)phosphanediyl)bis(4,1-phenylene))dipyrrolidine (216 mg, 0.55 mmol), Tf$_2$O (84 μL, 0.50 mmol), DBU (75 μL, 0.50 mmol), CH$_2$Cl$_2$ (5 mL), HOTf (67 μL, 0.75 mmol), MeOH (2.5 mL) and H$_2$O (90 μL, 5.00 mmol) at rt for 48 hours. The crude material was purified by flash chromatography (silica gel: 17% EtOAc in hexanes to 33% EtOAc in hexanes) to provide the title compound as a white solid (115 mg, 0.47 mmol, 93% yield). mp 76-78° C.; $^1$H NMR (400 MHz, CDCl$_3$) δ: 8.44 (s, 1H), 8.29 (s, 1H), 4.02 (s, 3H), 2.25-2.19 (m, 1H), 1.25-1.20 (m, 2H), 1.00-0.96 (m, 2H); $^{13}$C NMR (100 MHz, CDCl$_3$) δ: 164.73, 148.52, 146.02, 140.71, 138.10 (q, J=31.9 Hz), 123.05 (q, J=273.3 Hz), 120.78 (q, J=5.1 Hz), 53.11, 10.87, 9.67; $^{19}$F NMR (376 MHz, CDCl$_3$) δ: −62.60; IR ν$_{max}$/cm$^{-1}$ (film): 3424, 3029, 2963, 1718, 1680, 1601, 1558, 1491, 1456, 1442, 1323, 1310, 1258, 1154, 1124, 1069, 1042, 1017, 986, 923, 909, 879, 863, 806, 788, 754, 746, 669, 629; m/z HRMS (DART): [M+H]$^+$ calculated for C$_{11}$HF$_3$NO$_2$$^+$=246.0736, found 246.0752.

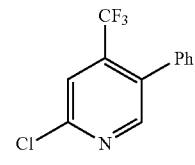 [SMILES: FC(F)(F)c1cc(Cl)ncc1-c1ccccc1]

2-Chloro-5-phenyl-4-(trifluoromethyl)pyridine (25). Prepared according to general procedure A using 2-chloro-5-phenylpyridine (95 mg, 0.50 mmol), 1,1'-(((trifluoromethyl)phosphanediyl)bis(4,1-phenylene))dipyrrolidine (216 mg, 0.55 mmol), Tf$_2$O (84 µL, 0.50 mmol), DBU (75 µL, 0.50 mmol), CH$_2$Cl$_2$ (5 mL), HOTf (67 µL, 0.75 mmol), THF (2.5 mL) and H$_2$O (90 µL, 5.00 mmol) at 80° C. for 72 20 hours. The crude material was purified by flash chromatography (silica gel: 33% CH$_2$Cl$_2$ in hexanes) to provide the title compound as a colorless oil (92 mg, 0.37 mmol, 73% yield). $^1$H NMR (400 MHz, CDCl$_3$) δ: 8.43 (s, 1H), 7.67 (s, 1H), 7.48-7.43 (m, 3H), 7.34-7.31 (m, 2H); $^{13}$C NMR (100 MHz, CDCl$_3$) δ: 152.64, 151.36, 138.59 (q, J=32.1 Hz), 134.67 (q, J=1.8 Hz), 134.55, 129.26 (q, J=1.5 Hz), 128.94, 128.44, 122.19 (q, J=273.7 Hz), 120.67 (q, J=5.2 Hz); $^{19}$F NMR (376 MHz, CDCl$_3$) δ: −59.70; IR ν$_{max}$/cm$^{-1}$ (film): 3061, 1586, 1463, 1445, 1303, 1284, 1253, 1215, 1122, 1076, 1035, 885, 840, 775, 757, 699, 684, 665; m/z HRMS (DART): [M+H]$^+$ calculated for C$_{12}$H$_8$ClF$_3$N$^+$=258.0292, found 258.0297.

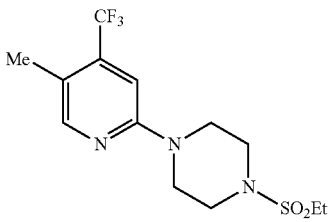

1-(Ethylsulfonyl)-4-(5-methyl-4-(trifluoromethyl)pyridin-2-yl)piperazin (26). Prepared according to general procedure A using 1-(ethylsulfonyl)-4-(5-methylpyridin-2-yl)piperazine (135 mg, 0.50 mmol), 1,1'-(((trifluoromethyl)phosphanediyl)bis(4,1-phenylene))dipyrrolidine (216 mg, 0.55 mmol), Tf$_2$O (84 µL, 0.50 mmol), DBU (75 µL, 0.50 mmol), CH$_2$Cl$_2$ (5 mL), HOTf (67 µL, 0.75 mmol), MeOH (2.5 mL) and H$_2$O (90 µL, 5.00 mmol) at 40° C. for 48 hours. The crude material was purified by flash chromatography (silica gel: 33% EtOAc in hexanes) to provide the title compound as an off-white solid (28 mg, 0.08 mmol, 16% yield). mp 103-106° C.; $^1$H NMR (400 MHz, CDCl$_3$) δ: 8.11 (s, 1H), 6.83 (s, 1H), 3.65-3.63 (m, 4H), 3.41-3.38 (m, 4H), 2.98 (q, J=7.4 Hz, 2H), 2.30 (q, J=1.8 Hz, 3H), 1.38 (t, J=7.4 Hz, 3H); $^{13}$C NMR (100 MHz, CDCl$_3$) δ:157.79, 150.94, 138.26 (q, J=30.7 Hz), 123.55 (q, J=273.0 Hz), 119.74 (q, J=1.6 Hz), 103.46 (d, J=5.5 Hz), 45.63, 45.54, 44.10, 15.18 (q, J=1.5 Hz), 7.88; $^{19}$F NMR (376 MHz, CDCl$_3$) δ: −64.34; IR ν$_{max}$/cm$^{-1}$ (film): 2980, 2926, 2870, 1726, 1612, 1499, 1433, 1386, 1354, 1342, 1326, 1303, 1276, 1244, 1219, 1193, 1138, 1117, 1067, 1048, 1005, 957, 937, 868, 847, 837, 779, 753, 715, 678; m/z HRMS (DART): [M+H]$^+$ calculated for C$_{13}$H$_{19}$F$_3$N$_3$O$_2$S$^+$=338.1145, found 338.1149.

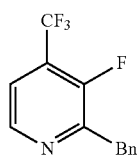

2-Benzyl-3-fluoro-4-(trifluoromethyl)pyridine (27) Prepared according to general procedure B, using 2-benzyl-3-fluoropyridine (94 mg, 0.50 mmol), Tf$_2$O (84 µL, 0.50 mmol), 1,1'-(((trifluoromethyl)phosphanediyl)bis(4,1-phenylene))dipyrrolidine (216 mg, 0.55 mmol), DBU (75 µL, 0.50 mmol), CH$_2$Cl$_2$ (5 mL), NaHCO$_3$ (126 mg, 1.50 mmol), H$_2$O (90 µL, 5.00 mmol), THF (2.5 mL) at rt for 30 minutes. The crude material was purified by flash chromatography (silica gel: 50% EtOAc in hexanes) to provide the title compound as a colorless oil (75 mg, 0.29 mmol, 58% yield). $^1$H NMR (400 MHz, CDCl$_3$) δ: 8.51 (d, J=4.9 Hz, 1H), 7.39-7.21 (m, 6H), 4.27 (d, J=3.1 Hz, 2H); $^{13}$C NMR (100 MHz, CDCl$_3$) δ: 153.77 (dq, J=267.0, 2.3 Hz), 151.46 (d, J=15.0 Hz), 145.54 (d, J=7.2 Hz), 137.51, 129.12, 128.81, 126.94, 125.64 (qd, J=34.0, 11.1 Hz), 121.62 (q, J=273.6 Hz), 119.0 (qd, J=4.0, 1.2 Hz), 38.08; $^{19}$F NMR (376 MHz, CDCl$_3$) δ: −62.72 (J=12.5 Hz, 3F), −127.75-(−127.61) (m, 1F), IR ν$_{max}$/cm$^{-1}$ (film): 3032, 2932, 1430, 1226, 1149, 907, 728. m/z HRMS (DART): [M+H]$^+$ calculated for C$_{13}$H$_{10}$F$_4$N$^+$=256.0749, found 256.0772.

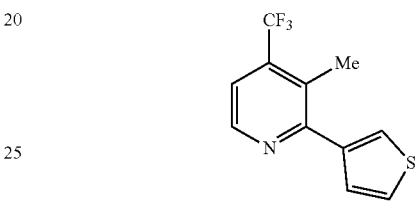

3-Methyl-2-(thiophen-3-yl)-4-(trifluoromethyl)pyridine (28). Prepared according to general procedure A, using 3-methyl-2-(thiophen-3-yl)pyridine (88 mg, 0.50 mmol), Tf$_2$O (84 µL, 0.50 mmol), 1,1'-(((trifluoromethyl)phosphanediyl)bis(4,1-phenylene))dipyrrolidine (216 mg, 0.55 mmol), DBU (75 µL, 0.50 mmol), CH$_2$Cl$_2$ (5 mL), HOTf (68 µL, 0.77 mmol), H$_2$O (90 µL, 5.00 mmol), MeOH (2.5 mL) at rt for 20 hours. The crude material was purified by flash chromatography (silica gel: 10% EtOAc in hexanes) to provide the title compound as a colorless oil (72 mg, 0.29 mmol, 59% yield). $^1$H NMR (400 MHz, CDCl$_3$) δ: 8.64 (d, J=5.0 Hz, 1H), 7.55 (dd, J=3.0, 1.3 Hz, 1H), 7.46 (d, J=5.0 Hz, 1H), 7.43 (dd, J=5.0, 3.0 Hz, 1H), 7.36 (dd, J=5.0, 1.3 Hz, 1H), 2.53 (d, J=1.6 Hz, 3H); $^{13}$C NMR (100 MHz, CDCl$_3$) δ: 156.79, 147.37, 140.62, 137.76 (q, J=30.8 Hz), 128.84 (m), 128.78, 125.87, 125.61, 123.50 (q, J=275.1 Hz), 118.23 (q, J=5.3 Hz), 16.24 (q, J=1.9 Hz); $^{19}$F NMR (376 MHz, CDCl$_3$) δ: −63.10, IR ν$_{max}$/cm$^{-1}$ (film): 2928, 2359, 1425, 1317, 1129, 1057, 907, 732, 530. m/z HRMS (DART): [M+H]$^+$ calculated for C$_{11}$H$_9$F$_3$NS$^+$=244.0408, found 244.0404.

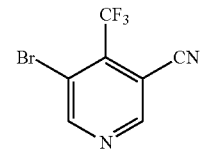 [SMILES: N#Cc1cncc(Br)c1C(F)(F)F]

5-Bromo-4-(trifluoromethyl)nicotinonitrile (29). Prepared according to general procedure A (except that after Tf$_2$O added, the reaction mixture was stirred for 1 hour at −30° C.) using 5-bromonicotinonitrile (92 mg, 0.50 mmol), 1,1'-(((trifluoromethyl)phosphanediyl)bis(4,1-phenylene))dipyrrolidine (216 mg, 0.55 mmol), Tf$_2$O (84 µL, 0.50 mmol), DBU (75 µL, 0.50 mmol), CH$_2$Cl$_2$ (5 mL), HOTf (67 µL, 0.75 mmol), MeOH (2.5 mL) and H$_2$O (90 µL, 5.00 mmol) at rt for 12 hours. The crude material was purified by flash chromatography (silica gel: 80% CH$_2$Cl$_2$ in hexanes) to provide the title compound as a white solid (65 mg, 0.26 mmol, 51% yield). mp 40-43° C.; $^1$H NMR (400 MHz, CDCl$_3$) δ: 9.11 (s, 1H), 8.97 (s, 1H); $^{13}$C NMR (100 MHz, CDCl$_3$) δ: 158.07, 153.44, 138.75 (q, J=32.9 Hz), 122.71 (q, J=275.9 Hz), 119.11, 113.23, 108.54 (q, J=1.3 Hz); $^{19}$F NMR (376 MHz, CDCl$_3$) δ: −60.76; IR ν$_{max}$/cm$^{-1}$ (film): 3070, 2923, 2240, 1547, 1535, 1407, 1277, 1233, 1208, 1196, 1171, 1148, 1057, 916, 850, 757, 687, 609; m/z HRMS (DART): [M+H]$^+$ calculated for C$_7$H$_3$BrF$_3$N$_2$$^+$=250.9426, found 250.9429.

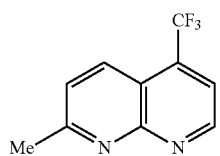 [SMILES: Cc1ccc2c(C(F)(F)F)ccnc2n1]

2-Methyl-5-(trifluoromethyl)-1,8-naphthyridine (30). Prepared according to general procedure A (except that after Tf$_2$O added, the reaction mixture was stirred for 1 hour at −50° C.) using 2-methyl-1,8-naphthyridine (72 mg, 0.50 mmol), 1,1'-(((trifluoromethyl)phosphanediyl)bis(4,1-phenylene))dipyrrolidine (216 mg, 0.55 mmol), Tf$_2$O (84 µL, 0.50 mmol), DBU (75 µL, 0.50 mmol), CH$_2$Cl$_2$ (5 mL), HOTf (111 µL, 1.25 mmol), MeOH (2.5 mL) and H$_2$O (90 µL, 5.00 mmol) at rt for 12 hours. The crude material was purified by flash chromatography (silica gel: 33% EtOAc, 2% Et$_3$N in hexanes) to provide the title compound as a brown solid (55 mg, 0.26 mmol, 51% yield). $^1$H NMR (400 MHz, CDCl$_3$) δ: 9.21 (d, J=4.4 Hz, 1H), 8.39 (qd, J=1.9, 8.7 Hz, 1H), 7.72 (d, J=4.4 Hz, 1H), 7.51 (d, J=8.7 Hz, 1H), 2.85 (s, 3H); $^{13}$C NMR (100 MHz, CDCl$_3$) δ: 164.21, 156.26, 152.75, 135.34 (q, J=32.2 Hz), 133.18 (q, J=2.2 Hz), 124.43, 123.01 (q, J=272.8 Hz), 118.13 (q, J=5.0 Hz), 116.13 (q, J=0.5 Hz), 25.67; $^{19}$F NMR (376 MHz, CDCl$_3$) δ: −60.81.

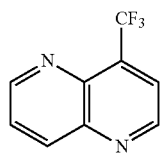

4-(Trifluoromethyl)-1,5-naphthyridine (31). Prepared according to general procedure A (except that after Tf$_2$O added, the reaction mixture was stirred for 1 hour at −50° C.) using 1,5-naphthyridine (65 mg, 0.50 mmol), 1,1'-(((trifluoromethyl)phosphanediyl)bis(4,1-phenylene))dipyrrolidine (216 mg, 0.55 mmol), Tf$_2$O (84 µL, 0.50 mmol), DBU (75 µL, 0.50 mmol), CH$_2$Cl$_2$ (5 mL), HOTf (111 µL, 1.25 mmol), MeOH (2.5 mL) and H$_2$O (90 µL, 5.00 mmol) at 40° C. for 16 hours. The crude material was purified by flash chromatography (silica gel: 33% EtOAc in hexanes) to provide the title compound as a white solid (41 mg, 0.21 mmol, 41% yield). $^1$H NMR (400 MHz, CDCl$_3$) δ: 9.15-9.13 (m, 2H), 8.51 (dd, J=1.8, 8.6 Hz, 1H), 7.93 (d, J=4.3 Hz, 1H), 7.77 (dd, J=4.2, 8.6 Hz, 1H); $^{13}$C NMR (100 MHz, CDCl$_3$) δ:152.22, 150.77, 144.75, 139.46, 137.86, 135.58 (q, J=31.2 Hz), 125.32, 122.97 (q, J=273.1 Hz), 121.29 (q, J=5.0 Hz); $^{19}$F NMR (376 MHz, CDCl$_3$) δ: −61.68.

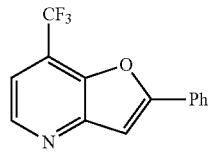 [SMILES: FC(F)(F)c1ccnc2cc(-c3ccccc3)oc12]

2-Phenyl-7-(trifluoromethyl)furo[3,2-b]pyridine (32). Prepared according to general procedure A using 2-phenyl-furo[3,2-b]pyridine (98 mg, 0.50 mmol), 1,1'-(((trifluoromethyl)phosphanediyl)bis(4,1-phenylene))dipyrrolidine (216 mg, 0.55 mmol), Tf$_2$O (84 µL, 0.50 mmol), DBU (75 µL, 0.50 mmol), CH$_2$Cl$_2$ (5 mL), HOTf (67 µL, 0.75 mmol), MeOH (2.5 mL) and H$_2$O (90 µL, 5.00 mmol) at rt for 12 hours. The crude material was purified by flash chromatography (silica gel: 17% EtOAc in hexanes to 33% EtOAc in hexanes) to provide the title compound as a light yellow solid (112 mg, 0.43 mmol, 85% yield). $^1$H NMR (400 MHz, CDCl$_3$) δ: 8.66 (d, J=5.0 Hz, 1H), 7.95-7.92 (m, 2H), 7.53-7.43 (m, 3H), 7.38 (d, J=5.0 Hz, 1H), 7.29 (s, 1H); $^{13}$C NMR (100 MHz, CDCl$_3$) δ: 161.36, 151.27, 146.32, 142.78, 130.28, 129.06, 128.84, 125.64, 122.28 (q, J=271.4 Hz), 120.71 (q, J=35.6 Hz), 114.36, 102.21; $^{19}$F NMR (376 MHz, CDCl$_3$) δ: −62.06.

4-(Trifluoromethyl)pyridazine-3-carbonitrile (33). Prepared according to general procedure A (except that after Tf$_2$O added, the reaction mixture was stirred for 1 hour at −50° C.) using pyridazine-3-carbonitrile (53 mg, 0.50 mmol), 1,1'-(((trifluoromethyl)phosphanediyl)bis(4,1-phenylene))dipyrrolidine (216 mg, 0.55 mmol), Tf$_2$O (84 µL, 0.50 mmol), DBU (75 µL, 0.50 mmol), CH$_2$Cl$_2$ (5 mL), HOTf (67 µL, 0.75 mmol), THF (2.5 mL) and H$_2$O (90 µL, 5.00 mmol) at rt for 12 hours. The crude material was purified by flash chromatography (silica gel: 33% EtOAc in hexanes) to provide the title compound as a light-yellow oil (32 mg, 0.19 mmol, 37% yield). $^1$H NMR (400 MHz, CDCl$_3$) δ: 9.64 (d, J=5.4 Hz, 1H), 7.93 (d, J=5.6 Hz, 1H); $^{13}$C NMR (100 MHz, CDCl$_3$) δ:152.62, 135.72 (q, J=0.9 Hz), 132.56 (q, J=36.2 Hz), 122.85 (q, J=4.1 Hz), 120.65 (q, J=273.6 Hz), 112.47; $^{19}$F NMR (376 MHz, CDCl$_3$) δ: −64.21; IR ν$_{max}$/cm$^{-1}$ (film): 3078, 1555, 1435, 1344, 1307, 1194, 1149, 1108, 1072, 1028, 867, 834, 783, 750, 663; m/z LRMS (ESI+APCI): [M+H]$^+$ calculated for C$_6$H$_3$F$_3$N$_3$$^+$=174.0, found 174.0.

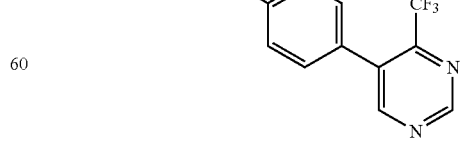

5-(4-Methoxyphenyl)-4-(trifluoromethyl)pyrimidine (34). Prepared according to general procedure A (except that after Tf$_2$O added, the reaction mixture was stirred for 1 hour at −50° C.) using 5-(4-methoxyphenyl)pyrimidine (93 mg, 0.50 mmol), 1,1'-(((trifluoromethyl)phosphanediyl)bis(4,1-phenylene))dipyrrolidine (216 mg, 0.55 mmol), Tf$_2$O (84 μL, 0.50 mmol), DBU (75 μL, 0.50 mmol), CH$_2$Cl$_2$ (5 mL), HOTf (67 μL, 0.75 mmol), MeOH (2.5 mL) and H$_2$O (90 μL, 5.00 mmol) at rt for 30 hours. The crude material was purified by flash chromatography (silica gel: 17% EtOAc in hexanes to 33% EtOAc in hexanes) to provide the title compound as an off-white solid (100 mg, 0.39 mmol, 78% yield). mp 66-70° C.; $^1$H NMR (400 MHz, CDCl$_3$) δ: 9.31 (s, 1H), 8.84 (s, 1H), 7.29-7.26 (m, 2H), 7.02-6.98 (m, 2H), 3.86 (s, 3H); $^{13}$C NMR (100 MHz, CDCl$_3$) δ: 160.97, 160.48, 156.98, 151.96 (q, J=33.9 Hz), 133.64, 130.29 (q, J=1.6 Hz), 125.31, 121.05 (q, J=275.2 Hz), 114.23, 55.42; $^{19}$F NMR (376 MHz, CDCl$_3$) δ: −63.60; IR ν$_{max}$/cm$^{-1}$ (film): 3021, 2966, 2934, 2839, 1612, 1572, 1548, 1515, 1459, 1450, 1440, 1416, 1398, 1326, 1308, 1294, 1251, 1231, 1180, 1166, 1132, 1110, 1085, 1032, 1018, 997, 930, 833, 819, 800, 786, 730, 658; m/z HRMS (DART): [M+H]$^+$ calculated for C$_{12}$H$_{10}$F$_3$N$_2$O$^+$=255.0740, found 255.0739.

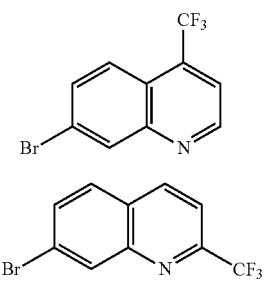

7-Bromo-4-(trifluoromethyl)quinoline (50). Prepared according to general procedure A using 7-bromoquinoline (104 mg, 0.50 mmol), 1,1'-(((trifluoromethyl)phosphanediyl)bis(4,1-phenylene))dipyrrolidine (216 mg, 0.55 mmol), Tf$_2$O (84 μL, 0.50 mmol), DBU (75 μL, 0.50 mmol), CH$_2$Cl$_2$ (5 mL), HOTf (67 μL, 0.75 mmol), THF (2.5 mL) and H$_2$O (90 μL, 5.00 mmol) at 40° C. for 24 hours. The crude material was purified by flash chromatography (silica gel: 33% EtOAc in hexanes to 50% EtOAc in hexanes) to provide the mixture of compounds as a light-brown solid (122 mg, 0.44 mmol, 88% yield). Major, $^1$H NMR (400 MHz, CDCl$_3$) δ: 9.03 (d, J=4.4 Hz, 1H), 8.40 (s, 1H), 7.99 (d, J=9.0 Hz, 1H), 7.76 (d, J=8.5 Hz, 1H), 7.70 (d, J=4.1 Hz, 1H); Major, $^{13}$C NMR (100 MHz, CDCl$_3$) δ: 150.75, 149.68, 134.60 (d, J=32.0 Hz), 132.87, 132.01, 125.44 (q, J=2.3 Hz), 124.74, 123.27 (q, J=273.0 Hz), 121.71, 118.31 (d, J=5.2 Hz); Major, $^{19}$F NMR (376 MHz, CDCl$_3$) δ: −61.44; IR ν$_{max}$/cm$^1$ (film): 3055, 3023, 2923, 1606, 1499, 1443, 1347, 1323, 1287, 1271, 1252, 1187, 1145, 1113, 1092, 1062, 977, 886, 856, 824, 775, 739, 653, 623, 610; m/z HRMS (DART): [M+H]$^+$ calculated for C$_{10}$H$_6$BrF$_3$N$^+$=275.9630, found 275.9616.

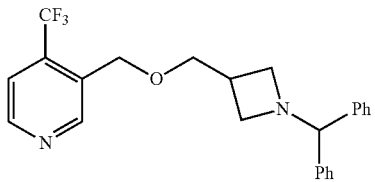 [SMILES: FC(F)(F)c1ccncc1COCC1CN(C(c2ccccc2)c2ccccc2)C1]

3-(((1-Benzhydrylazetidin-3-yl)methoxy)methyl)-4-(trifluoromethyl)pyridine (54). Prepared according to general procedure A (except that after Tf$_2$O added, the reaction mixture was stirred for 1 hour at −50° C.) using 3-(((1-benzhydrylazetidin-3-yl)methoxy)methyl)pyridine (86 mg, 0.25 mmol), 1,1'-(((trifluoromethyl)phosphanediyl)bis(4,1-phenylene))dipyrrolidine (108 mg, 0.28 mmol), Tf$_2$O (42 μL, 0.25 mmol), DBU (38 μL, 0.25 mmol), CH$_2$Cl$_2$ (2.5 mL), HOTf (56 μL, 0.63 mmol), MeOH (1.25 mL) and H$_2$O (45 μL, 2.50 mmol) at rt for 12 hours. The crude material was purified by flash chromatography (silica gel: 33% EtOAc, 2% Et$_3$N in hexanes) to provide the title compound as an off-white solid (77 mg, 0.19 mmol, 75% yield). mp 56-58° C.; $^1$H NMR (400 MHz, CDCl$_3$) δ: 8.90 (s, 1H), 8.70 (d, J=5.1 Hz, 1H), 7.48 (d, J=5.1 Hz, 1H), 7.40-7.37 (m, 4H), 7.27-7.23 (m, 4H), 7.18-7.13 (m, 2H), 4.69 (s, 2H), 4.33 (s, 2H), 3.69 (d, J=6.5 Hz, 2H), 3.29 (t, J=7.5 Hz, 2H), 2.93 (t, J=7.5 Hz, 2H), 2.81-2.71 (m, 1H); $^{13}$C NMR (100 MHz, CDCl$_3$) δ: 151.16, 149.83, 142.32, 135.37 (q, J=32.5 Hz), 131.02 (q, J=1.7 Hz), 128.50, 127.60, 127.13, 123.12 (q, J=273.2 Hz), 119.23 (q, J=5.1 Hz), 78.13, 73.70, 67.31 (q, J=2.2 Hz), 56.43, 29.82; $^{19}$F NMR (376 MHz, CDCl$_3$) δ: −62.39; IR ν$_{max}$/cm$^{-1}$ (film): 3031, 2942, 2911, 2853, 1731, 1724, 1596, 1489, 1451, 1404, 1368, 1348, 1318, 1301, 1235, 1205, 1181, 1151, 1129, 1067, 1036, 976, 840, 821, 808, 780, 747, 707, 659, 638, 614; m/z HRMS (DART): [M+H]$^+$ calculated for C$_{24}$H$_{24}$F$_3$N$_2$O$^+$=413.1835, found 413.1864.

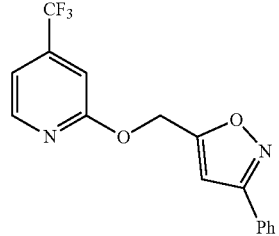 [SMILES: FC(F)(F)c1ccnc(OCc2cc(-c3ccccc3)no2)c1]

3-Phenyl-5-(((4-(trifluoromethyl)pyridin-2-yl)oxy)methyl)isoxazole (55). Prepared according to general procedure A using 3-phenyl-5-((pyridin-2-yloxy)methyl)isoxazole (63 mg, 0.25 mmol), 1,1'-(((trifluoromethyl)phosphanediyl)bis(4,1-phenylene))dipyrrolidine (108 mg, 0.28 mmol), Tf$_2$O (42 μL, 0.25 mmol), DBU (38 μL, 0.25 mmol), CH$_2$Cl$_2$ (2.5 mL), HOTf (56 μL, 0.63 mmol), MeOH (1.25 mL) and H$_2$O (90 μL, 5.00 mmol) at 80° C. for 72 hours. The crude material was purified by flash chromatography (silica gel: CH$_2$Cl$_2$) to provide the title compound as an off-white solid (56 mg, 0.18 mmol, 70% yield). mp 56-59° C.; $^1$H NMR (400 MHz, CDCl$_3$) δ: 8.34 (d, J=5.4 Hz, 1H), 7.83-7.79 (m, 2H), 7.49-7.43 (m, 3H), 7.16 (dd, J=1.0, 5.4 Hz, 1H), 7.08 (s, 1H), 6.65 (s, 1H), 5.58 (s, 2H); $^{13}$C NMR (100 MHz, CDCl$_3$) δ: 168.32, 162.96, 162.64, 148.31, 141.49 (q, J=33.8 Hz), 130.23, 129.05, 128.94, 126.96, 122.64 (q, J=271.6 Hz), 113.42 (q, J=3.2 Hz), 108.07 (q, J=4.0 Hz), 101.90, 58.81; $^{19}$F NMR (376 MHz, CDCl$_3$) δ: −64.96; IR ν$_{max}$/cm$^{-1}$ (film): 3120, 3053, 2920, 2850, 1622, 1569, 1490, 1473, 1426, 1407, 1337, 1289, 1271, 1231, 1170, 1160, 1131, 1081, 1037, 1002, 985, 951, 908, 884, 838, 826, 786, 766, 689, 667; m/z HRMS (DART): [M+H]$^+$ calculated for C$_{16}$H$_{12}$F$_3$N$_2$O$_2$$^+$=321.0845, found 321.0862.

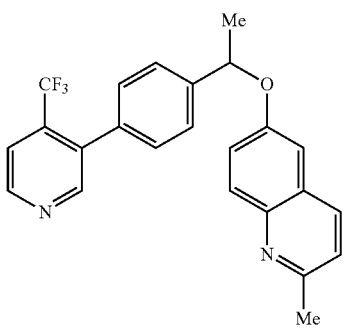 [SMILES: Cc1ccc2cc(OC(C)c3ccc(-c4cnccc4C(F)(F)F)cc3)ccc2n1]

2-Methyl-6-(1-(4-(4-(trifluoromethyl)pyridin-3-yl)phenyl)ethoxy)quinoline (56). Prepared according to general procedure A using 2-methyl-6-(1-(4-(pyridin-3-yl)phenyl)ethoxy)quinoline (85 mg, 0.25 mmol), 1,1'-(((trifluoromethyl)phosphanediyl)bis(4,1-phenylene))dipyrrolidine (108 mg, 0.28 mmol), Tf$_2$O (42 µL, 0.25 mmol), DBU (38 µL, 0.25 mmol), CH$_2$Cl$_2$ (2.5 mL), HOTf (56 µL, 0.63 mmol), MeOH (1.25 mL) and H$_2$O (45 µL, 2.50 mmol) at rt for 12 hours. The crude material was purified by flash chromatography (silica gel: 33% EtOAc, 2% Et$_3$N in hexanes to 33% EtOAc, 5% Et$_3$N in hexanes) to provide the title compound as a colorless oil (45 mg, 0.11 mmol, 44% yield). $^1$H NMR (400 MHz, CDCl$_3$) δ: 8.75 (d, J=5.2 Hz, 1H), 8.63 (s, 1H), 7.91 (d, J=9.2 Hz, 1H), 7.82 (d, J=8.4 Hz, 1H), 7.59 (d, J=5.2 Hz, 1H), 7.50 (d, J=8.1 Hz, 1H), 7.40 (dd, J=2.8, 9.2 Hz, 1H), 7.32 (d, J=8.0 Hz, 1H), 7.18 (d, J=8.5 Hz, 1H), 6.97 (d, J=2.8 Hz, 1H), 5.50 (q, J=6.4 Hz, 1H), 2.67 (s, 3H), 1.74 (d, J=6.4 Hz, 3H); $^{13}$C NMR (100 MHz, CDCl$_3$) δ: 156.64, 155.35, 152.70, 149.48, 143.95, 143.37, 135.91 (q, J=31.6 Hz), 135.18, 135.05, 130.18, 129.67 (q, J=1.7 Hz), 127.30, 125.52, 122.94 (q, J=273.3 Hz), 122.71, 122.29, 119.55 (q, J=4.8 Hz), 108.69, 76.13, 25.14, 24.33; $^{19}$F NMR (376 MHz, CDCl$_3$) δ: −59.25; IR ν$_{max}$/cm$^{-1}$ (film): 3031, 2979, 2929, 1622, 1601, 1563, 1497, 1478, 1443, 1398, 1376, 1342, 1320, 1304, 1255, 1224, 1179, 1134, 1064, 1001, 968, 940, 908, 831, 730, 659, 615; m/z HRMS (DART): [M+H]$^+$ calculated for C$_{24}$H$_{20}$F$_3$N$_2$O$^+$=409.1522, found 409.1541.

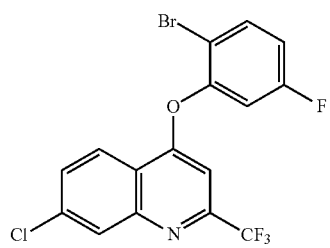 [SMILES: Fc1ccc(Br)c(Oc2cc(C(F)(F)F)nc3cc(Cl)ccc23)c1]

4-(2-Bromo-5-fluorophenoxy)-7-chloro-2-(trifluoromethyl)quinoline (57). Prepared according to general procedure A (except that after Tf$_2$O added, the reaction mixture was stirred for 1 hour at −50° C.) using 4-(2-bromo-5-fluorophenoxy)-7-chloroquinoline (88 mg, 0.25 mmol), 1,1'-(((trifluoromethyl)phosphanediyl)bis(4,1-phenylene))dipyrrolidine (108 mg, 0.28 mmol), Tf$_2$O (42 µL, 0.25 mmol), DBU (38 µL, 0.25 mmol), CH$_2$Cl$_2$ (2.5 mL), HOTf (33 µL, 0.38 mmol), THF (1.25 mL) and H$_2$O (45 µL, 2.50 mmol) at rt for 22 hours. The crude material was purified by flash chromatography (silica gel: 5% EtOAc in hexanes) to provide the title compound as a white solid (90 mg, 0.22 mmol, 86% yield). mp 150-153° C.; $^1$H NMR (400 MHz, CDCl$_3$) δ: 8.38 (d, J=8.9 Hz, 1H), 8.24 (d, J=2.0 Hz, 1H), 7.75-7.67 (m, 2H), 7.08-7.03 (m, 2H), 6.70 (s, 1H); $^{13}$C NMR (100 MHz, CDCl$_3$) δ: 162.60 (d, J=249.8 Hz), 161.89, 151.01 (d, J=10.5 Hz), 150.11 (q, J=34.8 Hz), 149.40, 138.05, 135.33 (d, J=9.0 Hz), 129.58, 128.97, 123.40, 121.09 (q, J=273.9 Hz), 119.74, 115.73 (d, J=22.2 Hz), 111.36 (d, J=24.8 Hz), 110.83 (d, J=4.2 Hz), 99.91 (q, J=2.2 Hz); $^{19}$F NMR (376 MHz, CDCl$_3$) δ: −67.87, −109.55; IR ν$_{max}$/cm$^{-1}$ (film): 3101, 3081, 1614, 1588, 1569, 1478, 1438, 1424, 1412, 1372, 1285, 1244, 1197, 1158, 1147, 1128, 1118, 1102, 1073, 1038, 963, 950, 925, 914, 880, 865, 842, 829, 815, 739, 621, 600; m/z HRMS (DART): [M+H]$^+$ calculated for C$_{16}$H$_8$BrClF$_4$NO$^+$=419.9408, found 419.9420.

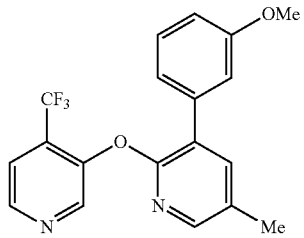 [SMILES: COc1cccc(-c2cc(C)cnc2Oc2cnccc2C(F)(F)F)c1]

3-(3-Methoxyphenyl)-5-methyl-2-((4-(trifluoromethyl)pyridin-yl) oxy)pyridine (58). Prepared according to general procedure A using 3-(3-methoxyphenyl)-5-methyl-2-(pyridin-3-yloxy)pyridine (73 mg, 0.25 mmol), 1,1'-(((trifluoromethyl)phosphanediyl)bis(4,1-phenylene))dipyrrolidine (108 mg, 0.28 mmol), Tf$_2$O (42 µL, 0.25 mmol), DBU (38 µL, 0.25 mmol), CH$_2$Cl$_2$ (2.5 mL), HOTf (56 µL, 0.63 mmol), MeOH (1.25 mL) and H$_2$O (45 µL, 2.50 mmol) at 40° C. for 24 hours. The crude material was purified by flash chromatography (silica gel: 33% EtOAc, 2% Et$_3$N in hexanes) to provide the title compound as a colorless oil (66 mg, 0.18 mmol, 73% yield). $^1$H NMR (400 MHz, CDCl$_3$) δ: 8.55-8.53 (m, 2H), 7.90 (dd, J=0.8, 2.4 Hz, 1H), 7.63 (dd, J=0.8, 2.4 Hz, 1H), 7.56 (d, J=5.0 Hz, 1H), 7.39-7.35 (m, 1H), 7.22-7.20 (m, 2H), 6.94 (ddd, J=1.4, 2.2, 8.2 Hz, 1H), 3.85 (s, 3H), 2.35 (s, 3H); $^{13}$C NMR (100 MHz, CDCl$_3$) δ: 159.62, 157.51, 147.69, 146.57, 145.82, 145.53, 141.19, 136.95, 129.83 (q, J=32.6 Hz), 129.73, 129.51, 125.05, 122.28 (q, J=272.2 Hz), 121.66, 120.26 (q, J=4.5 Hz), 114.69, 114.09, 55.31, 17.54; $^{19}$F NMR (376 MHz, CDCl$_3$) δ: −63.10; IR ν$_{max}$/cm$^{-1}$ (film): 2938, 2836, 1571, 1490, 1456, 1440, 1407, 1322, 1288, 1231, 1184, 1137, 1068, 1056, 1040, 937, 869, 836, 820, 784, 743, 698, 649, 615; m/z HRMS (DART): [M+H]$^+$ calculated for C$_{19}$H$_{16}$F$_3$N$_2$O$_2^+$=361.1158, found 361.1173.

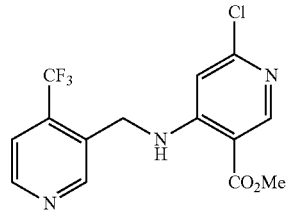 [SMILES: COC(=O)c1cnc(Cl)cc1NCc1cnccc1C(F)(F)F]

Methyl 6-chloro-4-(((4-(trifluoromethyl)pyridin-3-yl)methyl)amino)nicotinate (59). Prepared according to general procedure A using methyl 6-chloro-4-((pyridin-3-ylmethyl)amino)nicotinate (70 mg, 0.25 mmol), 1,1'-(((trifluoromethyl)phosphanediyl)bis(4,1-phenylene))

dipyrrolidine (108 mg, 0.28 mmol), Tf$_2$O (42 µL, 0.25 mmol), DBU (38 µL, 0.25 mmol), CH$_2$Cl$_2$ (2.5 mL), HOTf (56 µL, 0.63 mmol), MeOH (1.25 mL) and H$_2$O (45 µL, 2.50 mmol) at rt for 12 hours. The crude material was purified by flash chromatography (silica gel: 33% EtOAc in hexanes to 33% EtOAc, 2% Et$_3$N in hexanes) to provide the title compound as a white solid (77 mg, 0.22 mmol, 89% yield). mp 115-118° C.; $^1$H NMR (400 MHz, CDCl$_3$) δ: 8.78-8.73 (m, 3H), 8.66 (t, J=5.9 Hz, 1H), 7.59 (d, J=5.1 Hz, 1H), 6.47 (s, 1H), 4.67 (d, J=5.9 Hz, 2H), 3.90 (s, 3H); $^{13}$C NMR (100 MHz, CDCl$_3$) δ:167.89, 156.25, 155.61, 153.19, 150.53, 150.44, 135.99 (q, J=32.5 Hz), 129.21, 123.05 (q, J=273.2 Hz), 119.81 (q, J=5.0 Hz), 107.44, 104.89, 52.18, 41.25 (q, J=2.6 Hz); $^{19}$F NMR (376 MHz, CDCl$_3$) δ: −62.47; IR ν$_{max}$/cm$^{-1}$ (film): 3310, 3009, 2955, 2846, 1710, 1586, 1559, 1500, 1448, 1436, 1419, 1393, 1358, 1309, 1275, 1261, 1244, 1215, 1182, 1152, 1109, 1062, 977, 960, 934, 888, 838, 786, 776, 750, 717, 661, 613; m/z HRMS (DART): [M+H]$^+$ calculated for C$_{14}$H$_{12}$ClF$_3$N$_3$O$_2$$^+$=346.0565, found 346.0570.

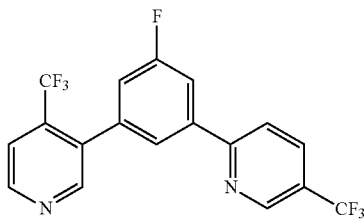

2-(3-Fluoro-5-(4-(trifluoromethyl)pyridin-3-yl)phenyl)-5-(trifluoromethyl)pyridine (60). Prepared according to general procedure A using 2-(3-fluoro-5-(pyridin-3-yl)phenyl)-5-(trifluoromethyl)pyridine (80 mg, 0.25 mmol), 1,1'-(((trifluoromethyl)phosphanediyl)bis(4,1-phenylene)) dipyrrolidine (108 mg, 0.28 mmol), Tf$_2$O (42 µL, 0.25 mmol), DBU (38 µL, 0.25 mmol), CH$_2$Cl$_2$ (2.5 mL), HOTf (56 µL, 0.63 mmol), MeOH (1.25 mL) and H$_2$O (45 µL, 2.50 mmol) at rt for 12 hours. The crude material was purified by flash chromatography (silica gel: 33% EtOAc in hexanes) to provide the title compound as a white solid (84 mg, 0.22 mmol, 87% yield). mp 87-90° C.; $^1$H NMR (400 MHz, CDCl$_3$) δ: 8.96-8.95 (m, 1H), 8.86 (d, J=5.2 Hz, 1H), 8.73 (s, 1H), 8.02 (dd, J=2.4, 4.4 Hz, 1H), 7.91-7.83 (m, 3H), 7.67 (d, J=5.1 Hz, 1H); $^{13}$C NMR (100 MHz, CDCl$_3$) δ:162.91 (d, J=246.6 Hz), 161.67, 158.56 (q, J=1.3 Hz), 152.36, 150.31, 146.93 (q, J=4.0 Hz), 140.25 (d, J=8.1 Hz), 138.39 (d, J=8.3 Hz), 136.05 (q, J=31.9 Hz), 134.38 (q, J=3.5 Hz), 133.83, 125.88 (q, J=33.0 Hz), 124.01 (q, J=1.5 Hz), 123.65 (q, J=270.6 Hz), 122.86 (q, J=273.2 Hz), 120.21, 119.68 (q, J=4.5 Hz), 118.02 (dd, J=1.6, 22.8 Hz), 114.59 (d, J=23.0 Hz); $^{19}$F NMR (376 MHz, CDCl$_3$) δ: −59.27, −62.37, −111.82; IR ν$_{max}$/cm$^{-1}$ (film): 3046, 2924, 2360, 1599, 1573, 1492, 1430, 1399, 1384, 1330, 1316, 1279, 1239, 1183, 1170, 1153, 1135, 1113, 1081, 1067, 1042, 1014, 938, 922, 882, 840, 769, 697, 658, 633, 616; m/z HRMS (DART): [M+H]$^+$ calculated for C$_{18}$H$_{10}$F$_7$N$_2$$^+$=387.0727, found 387.0748.

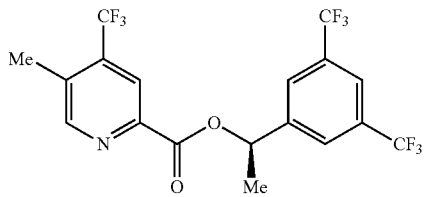 [SMILES: Cc1cnc(C(=O)O[C@H](C)c2cc(C(F)(F)F)cc(C(F)(F)F)c2)cc1C(F)(F)F]

(R)-1-(3,5-Bis(trifluoromethyl)phenyl)ethyl 5-methyl-4-(trifluoromethyl)picolinate (63). Prepared according to general procedure A using (R)-1-(3,5-bis(trifluoromethyl)phenyl) ethyl 5-methylpicolinate (76 mg, 0.20 mmol), 1,1'-(((trifluoromethyl)phosphanediyl)bis(4,1-phenylene)) dipyrrolidine (86 mg, 0.22 mmol), Tf$_2$O (34 µL, 0.20 mmol), DBU (30 µL, 0.20 mmol), CH$_2$Cl$_2$ (2 mL), HOTf (18 µL, 0.20 mmol), TBAF (0.2 mL, 0.20 mmol, 1M in THF) at rt for 24 hours. The crude material was purified by flash chromatography (silica gel: 50% DCM in hexanes to 80% DCM in hexanes) to provide the title compound as a white solid (76 mg, 0.17 mmol, 85% yield). mp 55-57° C.; $^1$H NMR (400 MHz, CDCl$_3$) δ: 8.75 (s, 1H), 8.28 (s, 1H), 7.93 (s, 2H), 7.83 (s, 1H), 6.28 (q, J=6.7 Hz, 1H), 2.57 (s, 3H) 1.80 (d, J=6.7 Hz, 3H); $^{13}$C NMR (100 MHz, CDCl$_3$) δ: 163.59, 153.46, 146.63, 143.76, 137.73 (q, J=32.2 Hz), 135.51 (q, J=1.7 Hz), 132.23 (q, J=33.2 Hz), 126.72 (q, J=3.8 Hz), 123.28 (q, J=271.0 Hz), 122.87 (q, J=273.1 Hz), 122.42-122.23 (m), 121.18 (q, J=5.1 Hz), 72.93, 22.05, 16.51 (q, J=1.9 Hz); $^{19}$F NMR (376 MHz, CDCl$_3$) δ: −62.90, −64.10; IR ν$_{max}$/cm$^{-1}$ (film): 1746, 1382, 1370, 1361, 1321, 1303, 1283, 1268, 1243, 1200, 1163, 1114, 1103, 1067, 1059, 1005, 915, 900, 857, 841, 816, 787, 744, 728, 707, 683, 677; LRMS (ESI+APCI): [M+H]$^+$ calculated for C$_{18}$H$_{13}$F$_9$NO$_2$$^+$=446.1, found 446.2.

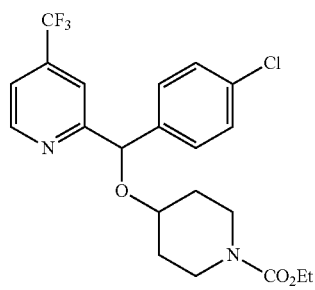 [SMILES: CCOC(=O)N1CCC(OC(c2ccc(Cl)cc2)c2cc(C(F)(F)F)ccn2)CC1]

Ethyl 4-((4-chlorophenyl)(4-(trifluoromethyl)pyridin-2-yl)methoxy)piperidine-1-carboxylate (65). Prepared according to general procedure A (except that after Tf$_2$O added, the reaction mixture was stirred for 1 hour at −50° C.) using ethyl 4-((4-chlorophenyl)(pyridin-2-yl)methoxy)piperidine-1-carboxylate (94 mg, 0.25 mmol), 1,1'-(((trifluoromethyl) phosphanediyl) bis(4,1-phenylene))dipyrrolidine (108 mg, 0.28 mmol), Tf$_2$O (42 µL, 0.25 mmol), DBU (38 µL, 0.25 mmol), CH$_2$Cl$_2$ (2.5 mL), HOTf (33 µL, 0.38 mmol), MeOH (1.25 mL) and H$_2$O (45 µL, 2.50 mmol) at rt for 12 hours. The crude material was purified by flash chromatography (silica gel: 33% EtOAc in hexanes) to provide the title compound as a colorless oil (85 mg, 0.19 mmol, 77% yield). $^1$H NMR (400 MHz, CDCl$_3$) δ: 8.67 (d, J=5.1 Hz, 1H), 7.77 (s, 1H), 7.39-7.35 (m, 3H), 7.32-7.28 (m, 2H), 5.67 (s, 1H), 4.12 (q, J=7.1 Hz, 2H), 3.80-3.76 (m, 2H), 3.66-3.60 (m, 1H), 3.22-3.15 (m, 2H), 1.87-1.81 (m, 2H), 1.71-1.62 (m, 2H), 1.24 (t, J=7.1 Hz, 3H); $^{13}$C NMR (100 MHz, CDCl$_3$)

δ: 163.79, 155.59, 150.05, 139.35, 139.34 (q, J=33.8 Hz), 133.94, 128.90, 128.31, 122.87 (q, J=271.7 Hz), 118.21 (q, J=3.6 Hz), 116.08 (q, J=3.7 Hz), 80.60, 73.08, 61.40, 41.18, 41.09, 31.39, 30.89, 14.76; $^{19}$F NMR (376 MHz, CDCl$_3$) δ: −64.73; IR $v_{max}$/cm$^{-1}$ (film): 2931, 1692, 1488, 1473, 1432, 1407, 1383, 1331, 1273, 1227, 1204, 1167, 1135, 1083, 1029, 1014, 964, 921, 832, 767, 723, 665; m/z HRMS (DART): [M+H]$^+$ calculated for $C_{21}H_{23}ClF_3N_2O_3^+$=443.1344, found 443.1347.

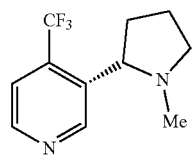

(S)-3-(1-Methylpyrrolidin-2-yl)-4-(trifluoromethyl)pyridine (69). Prepared according to general procedure A using (S)-3-(1-methylpyrrolidin-2-yl)pyridine (33 mg, 0.20 mmol), 1,1'-(((trifluoromethyl)phosphanediyl)bis(4,1-phenylene))dipyrrolidine (86 mg, 0.22 mmol), Tf$_2$O (34 μL, 0.20 mmol), DBU (30 μL, 0.20 mmol), CH$_2$Cl$_2$ (2 mL), HOTf (44 μL, 0.50 mmol), MeOH (1 mL) and H$_2$O (36 μL, 2.00 mmol) at rt for 12 hours. The crude material was purified by flash chromatography (silica gel: EtOAc) to provide the title compound as a light-yellow oil (30 mg, 0.13 mmol, 65% yield). $^1$H NMR (400 MHz, CDCl$_3$) δ: 9.18 (s, 1H), 8.64 (s, 1H), 7.43 (d, J=5.1 Hz, 1H), 3.53 (t, J=7.9 Hz, 1H), 3.27 (t, J=7.9 Hz, 1H), 2.38-2.24 (m, 2H), 2.18 (m, 3H), 2.05-1.93 (m, 1H), 1.88-1.78 (m, 1H), 1.71-1.62 (m, 1H); $^{13}$C NMR (100 MHz, CDCl$_3$) δ: 151.88, 148.71, 137.15, 136.03 (q, J=31.5 Hz), 123.34 (q, J=273.2 Hz), 118.57, 64.85, 56.88, 40.39, 35.91, 23.04; $^{19}$F NMR (376 MHz, CDCl$_3$) δ: −60.50; IR $v_{max}$/cm$^{-1}$ (film): 2944, 2779, 1454, 1409, 1315, 1290, 1235, 1170, 1128, 1062, 1043, 900, 835, 659, 614; m/z HRMS (DART): [M+H]$^+$ calculated for $C_{11}H_{14}F_3N_2^+$=231.1104, found 231.1106.

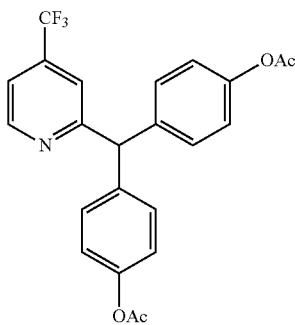 [SMILES: CC(=O)Oc1ccc(C(c2ccc(OC(C)=O)cc2)c2cc(C(F)(F)F)ccn2)cc1]

((4-(Trifluoromethyl)pyridin-2-yl)methylene)bis(4,1-phenylene) diacetate (70). Prepared according to general procedure B using (pyridin-2-ylmethylene)bis(4,1-phenylene) diacetate (72 mg, 0.20 mmol), 1,1'-(((trifluoromethyl)phosphanediyl)bis(4,1-phenylene))dipyrrolidine (86 mg, 0.22 mmol), Tf$_2$O (34 μL, 0.20 mmol), DBU (30 μL, 0.20 mmol), CH$_2$Cl$_2$ (2 mL), NaHCO$_3$ (50 mg, 0.60 mmol), THF (1 mL) and H$_2$O (36 μL, 2.00 mmol) at rt for 50 minutes. The crude material was purified by flash chromatography (silica gel: 33% EtOAc in hexanes) to provide the title compound as a white solid (78 mg, 0.18 mmol, 90% yield). mp 131-133° C.; $^1$H NMR (400 MHz, CDCl$_3$) δ: 8.78 (d, J=5.0 Hz, 1H), 7.39-7.37 (m, 2H), 7.19 (d, J=8.6 Hz, 4H), 7.05 (d, J=8.6 Hz, 4H), 5.71 (s, 1H), 2.81 (s, 6H); $^{13}$C NMR (100 MHz, CDCl$_3$) δ: 169.49, 164.31, 150.80, 149.68, 139.25, 139.06 (q, J=33.7 Hz), 130.32, 122.86 (q, J=271.7 Hz), 121.80, 119.31 (q, J=3.6 Hz), 117.48 (q, J=3.5 Hz), 58.14, 21.23; $^{19}$F NMR (376 MHz, CDCl$_3$) δ: −64.65; IR $v_{max}$/cm$^{-1}$ (film): 3053, 2926, 1749, 1607, 1570, 1503, 1479, 1403, 1367, 1330, 1269, 1216, 1201, 1162, 1140, 1107, 1087, 1046, 1015, 958, 919, 879, 862, 848, 838, 800, 777, 750, 697, 677, 657, 644, 630, 593; HRMS (DART): [M+H]$^+$ calculated for $C_{23}H_{19}F_3NO_4^+$=430.1261, found 430.1271.

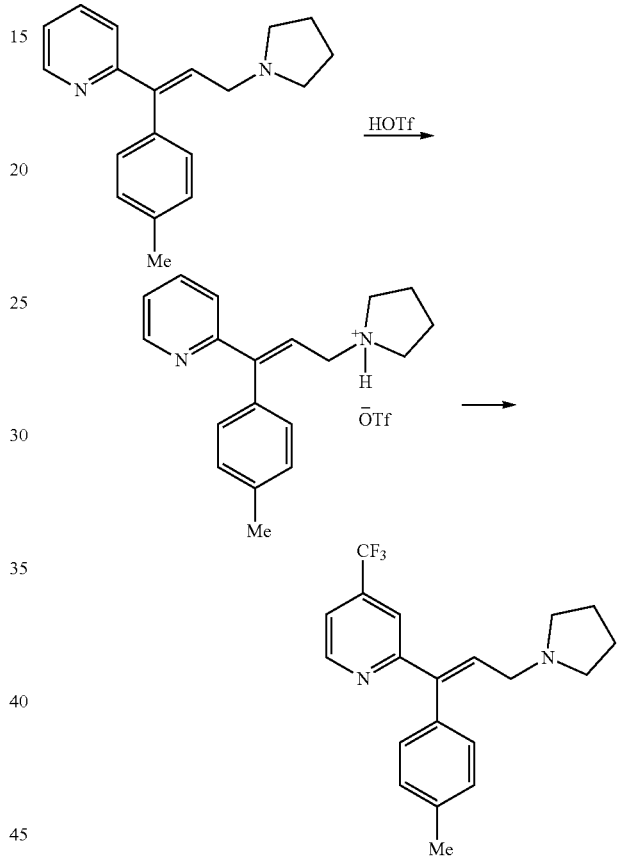

(E)-2-(3-(Pyrrolidin-1-yl)-1-(p-tolyl)prop-1-en-1-yl)-4-(trifluoromethyl)pyridine (72). (E)-2-(3-(pyrrolidin-1-yl)-1-(p-tolyl)prop-1-en-1-yl)pyridine (56 mg, 0.20 mmol) was dissolved in Et$_2$O (1 mL) and cooled to 0° C. Trifluoromethanesulfonic acid (18 μL, 0.20 mmol) was added dropwise, the ice bath was removed, and the solution was stirred for 10 minutes at room temperature. The solution was concentrated in vacuo and the resulting acid salt was subjected to general procedure A (except that after Tf$_2$O added, the reaction mixture was stirred for 1 hour at −50° C.) using 1,1'-(((trifluoromethyl)phosphanediyl)bis(4,1-phenylene))dipyrrolidine (86 mg, 0.22 mmol), Tf$_2$O (34 μL, 0.20 mmol), DBU (60 μL, 0.40 mmol), CH$_2$Cl$_2$ (2 mL), HOTf (44 μL, 0.50 mmol), MeOH (1 mL) and H$_2$O (36 μL, 2.00 mmol) at rt for 12 hours. The crude material was purified by flash chromatography (silica gel: 2% Et$_3$N in EtOAc) to provide the title compound as a light-yellow solid (43 mg, 0.12 mmol, 62% yield). mp 39-41° C.; $^1$H NMR (400 MHz, CDCl$_3$) δ: 8.73 (d, J=5.0 Hz, 1H), 7.31 (dd, J=1.6, 5.1 Hz, 1H), 7.24-7.22 (m, 3H), 7.08 (d, J=8.0 Hz, 2H), 7.03 (t, J=6.8 Hz, 1H), 3.23 (d, J=6.9 Hz, 2H), 2.56-2.51 (m, 4H), 2.40 (s, 3H), 1.79-1.74 (m, 4H); $^{13}$C NMR (100 MHz, CDCl$_3$) δ:160.26, 150.18, 141.11, 138.65 (q, J=33.4 Hz), 137.55, 134.64, 132.76, 129.76, 129.48, 123.01 (q, J=271.5 Hz), 117.40 (q, J=3.7 Hz), 117.25 (q, J=3.4 Hz), 54.84, 54.29, 23.64, 21.42; $^{19}$F NMR (376 MHz, CDCl$_3$) δ: −64.83; IR ν$_{max}$/cm$^{-1}$ (film): 3386, 3024, 2969, 2877, 2790, 1630, 1605, 1568, 1512, 1460, 1434, 1397, 1327, 1233, 1168, 1139, 1083, 957, 932, 902, 878, 839, 816, 782, 750, 729, 711, 690, 659, 641; HRMS (DART): [M+H]$^+$ calculated for C$_{20}$H$_{22}$F$_3$N$_2^+$=347.1730, found 347.1735.

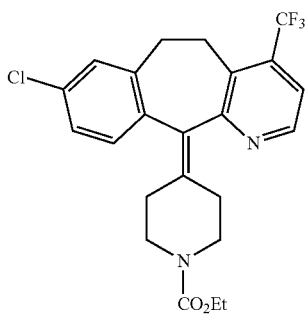 [SMILES: CCOC(=O)N1CCC(=C2c3ccc(Cl)cc3CCc3c(C(F)(F)F)ccnc32)CC1]

Ethyl 4-(8-chloro-4-(trifluoromethyl)-5,6-dihydro-11H-benzo[5,6]cyclohepta[1,2-b]pyridin-11-ylidene)piperidine-1-carboxylate (74). Prepared according to general procedure A using ethyl 4-(8-chloro-5,6-dihydro-11H-benzo[5,6]cyclohepta[1,2-b]pyridin-11-ylidene)piperidine-1-carboxylate (77 mg, 0.20 mmol), 1,1'-(((trifluoromethyl)phosphanediyl)bis(4,1-phenylene))dipyrrolidine (86 mg, 0.22 mmol), Tf$_2$O (34 µL, 0.20 mmol), DBU (30 µL, 0.20 mmol), CH$_2$Cl$_2$ (2 mL), HOTf (27 µL, 0.30 mmol), MeOH (1 mL) and H$_2$O (36 µL, 2.00 mmol) at rt for 16 hours. The crude material was purified by flash chromatography (silica gel: 33% EtOAc in hexanes to 50% EtOAc in hexanes) to provide the title compound as a colorless oil (75 mg, 0.17 mmol, 83% yield). $^1$H NMR (400 MHz, CDCl$_3$) δ: 8.55 (d, J=5.2 Hz, 1H), 7.41 (d, J=5.2 Hz, 2H), 7.11-7.09 (m, 3H), 4.14 (q, J=7.0 Hz, 2H), 3.82-3.75 (m, 2H), 3.44-3.36 (m, 2H), 3.29-3.13 (m, 3H), 2.97-2.88 (m, 1H), 2.51-2.33 (m, 3H), 2.14-2.08 (m, 1H), 1.24 (t, J=7.0 Hz, 3H); $^{13}$C NMR (100 MHz, CDCl$_3$) δ: 162.47, 155.57, 147.72, 138.37, 137.83, 136.35 (q, J=31.4 Hz), 134.63, 133.64, 133.47, 131.89, 131.31, 130.32, 126.23, 123.33 (q, J=273.5 Hz), 118.59 (q, J=5.2 Hz), 61.52, 44.89, 44.64, 31.92, 30.86, 30.62, 26.18, 14.77; $^{19}$F NMR (376 MHz, CDCl$_3$) δ: −61.88; IR ν$_{max}$/cm$^{-1}$ (film): 2980, 2909, 1692, 1590, 1476, 1430, 1406, 1326, 1300, 1278, 1222, 1155, 1119, 1092, 1061, 1028, 999, 981, 907, 844, 813, 766, 729, 690, 682; HRMS (DART): [M+H]$^+$ calculated for C$_{23}$H$_{23}$ClF$_3$N$_2$O$_2^+$=451.1395, found 451.1412.

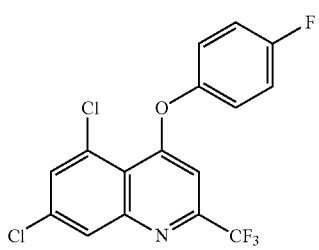 [SMILES: Fc1ccc(Oc2cc(C(F)(F)F)nc3cc(Cl)cc(Cl)c23)cc1]

5,7-Dichloro-4-(4-fluorophenoxy)-2-(trifluoromethyl)quinoline (70). Prepared according to general procedure A (except that after Tf$_2$O added, the reaction mixture was stirred for 1 hour at −50° C.) using 5,7-dichloro-4-(4-fluorophenoxy)quinoline (62 mg, 0.20 mmol), 1,1'-(((trifluoromethyl)phosphanediyl)bis(4,1-phenylene))dipyrrolidine (86 mg, 0.22 mmol), Tf$_2$O (34 µL, 0.20 mmol), DBU (30 µL, 0.20 mmol), CH$_2$Cl$_2$ (2 mL), HOTf (27 µL, 0.30 mmol), THF (1 mL) and H$_2$O (36 µL, 2.00 mmol) at rt for 22 hours. The crude material was purified by flash chromatography (silica gel: 5% EtOAc in hexanes) to provide the title compound as a white solid (68 mg, 0.18 mmol, 90% yield). mp 82-85° C.; $^1$H NMR (400 MHz, CDCl$_3$) δ: 8.12 (s, 1H), 7.70 (s, 1H), 7.26-7.15 (m, 5H), 6.86 (s, 1H); $^{13}$C NMR (100 MHz, CDCl$_3$) δ: 164.61, 160.67 (d, J=244.6 Hz), 150.88, 150.39 (q, J=35.0 Hz), 149.15 (d, J=2.8 Hz), 136.63, 131.53, 130.68, 128.55, 122.61 (d, J=8.5 Hz), 120.85 (q, J=274.0 Hz), 118.50, 117.68 (q, J=23.4 Hz), 102.15 (q, J=2.4 Hz); $^{19}$F NMR (376 MHz, CDCl$_3$) δ: −68.35, −115.41; IR ν$_{max}$/cm$^{-1}$ (film): 3103, 1750, 1599, 1586, 1565, 1503, 1431, 1386, 1366, 1330, 1316, 1266, 1241, 1214, 1186, 1139, 1123, 1099, 1070, 1014, 964, 926, 855, 835, 770, 738, 724, 694, 611; HRMS (DART): [M+H]$^+$ calculated for C$_{16}$H$_8$Cl$_2$F$_4$NO$^+$=375.9914, found 375.9930.

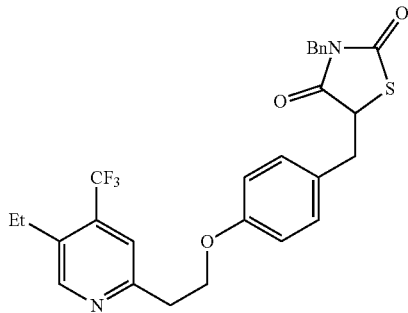 [SMILES: CCc1cnc(CCOc2ccc(CC3SC(=O)N(Cc4ccccc4)C3=O)cc2)cc1C(F)(F)F]

3-Benzyl-5-(4-(2-(5-ethyl-4-(trifluoromethyl)pyridin-2-yl)ethoxy)benzyl)thiazolidine-2,4-dione (77). Prepared according to general procedure B using 3-benzyl-5-(4-(2-(5-ethylpyridin-2-yl)ethoxy)benzyl)thiazolidine-2,4-dione (89 mg, 0.20 mmol), 1,1'-(((trifluoromethyl) phosphanediyl)bis(4,1-phenylene))dipyrrolidine (86 mg, 0.22 mmol), Tf$_2$O (34 µL, 0.20 mmol), DBU (30 L, 0.20 mmol), CH$_2$Cl$_2$ (2 mL), NaHCO$_3$ (50 mg, 0.60 mmol), THF (1 mL) and H$_2$O (36 µL, 2.00 mmol) at rt for 30 minutes. The crude material was purified by flash chromatography (silica gel: 33% EtOAc in hexanes) to provide the title compound as a white solid (50 mg, 0.10 mmol, 49% yield). mp 111-114° C.; $^1$H NMR (400 MHz, CDCl$_3$) δ: 8.57 (s, 1H), 7.45 (s, 1H), 7.25 (s, 5H), 7.04 (d, J=8.6 Hz, 2H), 6.75 (d, J=8.6 Hz, 2H), 4.72-4.64 (m, 2H), 4.42 (dd, J=4.0, 8.8 Hz, 1H), 4.32 (t, J=6.4 Hz, 2H), 3.38 (dd, J=4.0, 14.2 Hz, 1H), 3.28 (t, J=6.4 Hz, 2H), 3.38 (dd, J=8.8, 14.2 Hz, 1H), 2.81 (q, J=7.6 Hz, 2H), 1.27 (t, J=7.6 Hz, 3H); $^{13}$C NMR (100 MHz, CDCl$_3$) δ: 173.79, 171.02, 158.17, 157.13, 152.07, 136.14 (q, J=31.0 Hz), 135.12, 134.66 (q, J=1.6 Hz), 130.55, 128.73, 128.17, 127.70, 123.52 (q, J=273.1 Hz), 119.50 (q, J=5.2 Hz), 114.83, 66.82, 51.693, 45.24, 37.68, 37.62, 23.14 (q, J=1.8 Hz), 15.76; $^{19}$F NMR (376 MHz, CDCl$_3$) δ: −62.14; IR ν$_{max}$/cm$^{-1}$ (film): 3032, 2921, 1740, 1679, 1610, 1582, 1514, 1493, 1467, 1456, 1436, 1380, 1335, 1324, 1308, 1296, 1279, 1265, 1247, 1198, 1180, 1146, 1122, 1080, 1069, 1054, 1029, 964, 899, 879, 824, 810, 790, 745, 722, 696, 678, 668, 626, 601; HRMS (DART): [M+H]+ calculated for $C_{27}H_{26}F3N_2O_3S^+$=515.1611, found 515.1646.

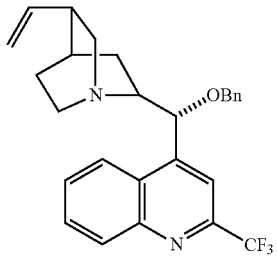 [SMILES: C=CC1CN2CCC1CC2[C@H](OCc1ccccc1)c1cc(C(F)(F)F)nc2ccccc12]

(1R,4R,5R)-2-((R)-(Benzyloxy)(2-(trifluoromethyl)quinolin-4-yl)methyl)-5-vinylquinuclidine (79). Prepared according to general procedure A (except that after Tf$_2$O added, the reaction mixture was stirred for 1 hour at −50° C.) using (1R,4R,5R)-2-((R)-(benzyloxy)(quinolin-4-yl)methyl)-5-vinylquinuclidine (77 mg, 0.20 mmol), 1,1'-(((trifluoromethyl)phosphanediyl) bis(4,1-phenylene))dipyrrolidine (86 mg, 0.22 mmol), Tf$_2$O (34 μL, 0.20 mmol), DBU (30 μL, 0.20 mmol), CH$_2$Cl$_2$ (2 mL), HOTf (44 μL, 0.50 mmol), MeOH (1 mL) and H$_2$O (36 μL, 2.00 mmol) at 40° C. for 20 hours. The crude material was purified by flash chromatography (silica gel: 2% Et$_3$N in EtOAc) to provide the title compound as a colorless oil (48 mg, 0.11 mmol, 53% yield). $^1$H NMR (400 MHz, CDCl$_3$) δ: 8.29 (d, J=8.1 Hz, 1H), 8.22 (d, J=8.6 Hz, 1H), 7.86-7.81 (m, 2H), 7.72-7.68 (m, 1H), 7.37-7.27 (m, 5H), 5.79-5.70 (m, 1H), 5.33 (s, 1H), 4.98-4.90 (m, 2H), 4.42 (dd, J=1.1, 13.1 Hz, 2H), 3.38-3.31 (m, 1H), 3.18-3.03 (m, 2H), 2.71-2.57 (m, 2H), 2.29-2.24 (m, 1H), 1.84-1.65 (s, 4H), 1.55-1.48 (m, 1H); $^{13}$C NMR (100 MHz, CDCl$_3$) δ:149.87, 147.86 (q, J=34.2 Hz), 147.77, 141.88, 137.41, 131.33, 130.54, 128.79, 128.66, 128.15, 128.14, 127.35, 123.41, 121.78 (q, J=273.8 Hz), 119.89, 114.51, 81.06, 72.00, 61.14, 57.09, 43.19, 40.03, 27.93, 27.79, 22.85; $^{19}$F NMR (376 MHz, CDCl$_3$) δ: −67.43; IR $\nu_{max}$/cm$^{-1}$ (film): 3066, 2934, 2864, 1636, 1596, 1569, 1511, 1467, 1454, 1423, 1363, 1320, 1251, 1212, 1180, 1132, 1095, 1046, 1027, 990, 905, 807, 761, 732, 698, 669; HRMS (DART): [M+H]+ calculated for $C_{27}H_{28}F_3N_2O^+$=453.2148, found 453.2177.

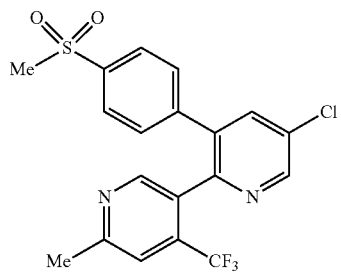 [SMILES: Cc1cc(C(F)(F)F)c(-c2ncc(Cl)cc2-c2ccc(S(C)(=O)=O)cc2)cn1]

5-Chloro-6'-methyl-3-(4-(methylsulfonyl)phenyl)-4'-(trifluoromethyl)-2,3'-bipyridine (80). Prepared according to general procedure A (except that after Tf$_2$O added, the reaction mixture was stirred for 1 hour at −50° C.) using 5-chloro-6'-methyl-3-(4-(methylsulfonyl)phenyl)-2,3'-bipyridine (72 mg, 0.20 mmol), 1,1'-(((trifluoromethyl)phosphanediyl)bis(4,1-phenylene))dipyrrolidine (86 mg, 0.22 mmol), Tf$_2$O (34 μL, 0.20 mmol), DBU (30 μL, 0.20 mmol), CH$_2$Cl$_2$ (2 mL), HOTf (44 μL, 0.50 mmol), MeOH (1 mL) and H$_2$O (36 μL, 2.00 mmol) at rt for 60 hours. The crude material was purified by flash chromatography (silica gel: 20% EtOAc in CH$_2$Cl$_2$ to 33% EtOAc in CH$_2$Cl$_2$) to provide the title compound as a colorless oil (68 mg, 0.16 mmol, 80% yield). $^1$H NMR (400 MHz, CDCl$_3$) δ: 8.70 (d, J=1.9 Hz, 1H), 8.25 (s, 1H), 7.83 (d, J=8.1 Hz, 2H), 7.79 (d, J=2.4 Hz, 1H), 7.42 (s, 1H), 7.31 (d, J=8.0 Hz, 2H), 3.02 (s, 3H), 2.61 (s, 3H); $^{13}$C NMR (100 MHz, CDCl$_3$) δ: 160.09, 151.81, 150.96, 148.02, 142.68, 140.36, 137.47, 136.81 (q, J=32.0 Hz), 136.59, 132.15, 130.33, 129.04, 127.82, 122.77 (q, J=273.5 Hz), 120.04 (q, J=3.5 Hz), 44.48, 24.48; $^{19}$F NMR (376 MHz, CDCl$_3$) δ: −60.13; IR $\nu_{max}$/cm$^{-1}$ (film): 3054, 2926, 1601, 1573, 1538, 1493, 1431, 1386, 1367, 1310, 1268, 1218, 1140, 1089, 1033, 1012, 956, 906, 888, 836, 790, 771, 728, 674, 661, 646, 593; HRMS (DART): [M+H]+ calculated for $C_{19}H_{15}Cl_2F_3N_2O_2S^+$=427.0489, found 427.0503.

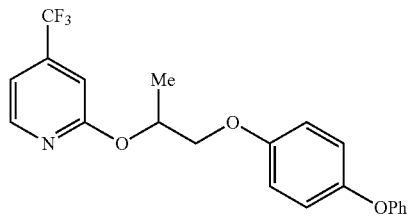 [SMILES: CC(COc1ccc(Oc2ccccc2)cc1)Oc1cc(C(F)(F)F)ccn1]

2-((1-(4-Phenoxyphenoxy)propan-2-yl)oxy)-4-(trifluoromethyl)pyridine (81). Prepared according to general procedure A using 2-((1-(4-phenoxyphenoxy)propan-2-yl)oxy) pyridine (64 mg, 0.20 mmol), 1,1'-(((trifluoromethyl) phosphanediyl)bis(4,1-phenylene))dipyrrolidine (86 mg, 0.22 mmol), Tf$_2$O (34 μL, 0.20 mmol), DBU (30 μL, 0.20 mmol), CH$_2$Cl$_2$ (2 mL), HOTf (27 μL, 0.30 mmol), MeOH (1 mL) and H$_2$O (36 μL, 2.00 mmol) at 60° C. for 68 hours. The crude material was purified by flash chromatography (silica gel: 33% CH$_2$Cl$_2$ in hexanes to 50% CH$_2$Cl$_2$ in hexanes) to provide the title compound as a colorless oil (55 mg, 0.14 mmol, 71% yield). $^1$H NMR (400 MHz, CDCl$_3$) δ: 8.31 (d, J=5.3 Hz, 1H), 7.33-7.28 (m, 2H), 7.08-7.03 (m, 2H), 7.00-6.90 (m, 7H), 5.67-5.62 (m, 1H), 4.20 (dd, J=5.6, 10.0 Hz, 1H), 4.09 (dd, J=4.6, 10.0 Hz, 1H), 1.50 (d, J=6.4 Hz, 3H); $^{13}$C NMR (100 MHz, CDCl$_3$) δ:163.78, 158.57, 155.18, 150.60, 148.33, 141.17 (q, J=33.6 Hz), 129.76, 122.80 (q, J=271.6 Hz), 122.64, 120.90, 117.81, 115.90, 112.42 (q, J=3.2 Hz), 108.46 (q, J=4.0 Hz), 71.01, 70.54, 16.93; $^{19}$F NMR (376 MHz, CDCl$_3$) δ: −65.01; IR $\nu_{max}$/cm$^{-1}$ (film): 3041, 2934, 1615, 1589, 1569, 1503, 1488, 1416, 1335, 1306, 1217, 1171, 1135, 1073, 1045, 989, 966, 872, 826, 767, 748, 690, 668; HRMS (DART): [M+H]+ calculated for $C_{21}H_{19}F3NO_3'$=390.1312, found 390.1338.

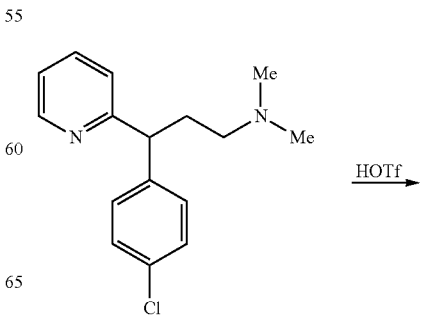

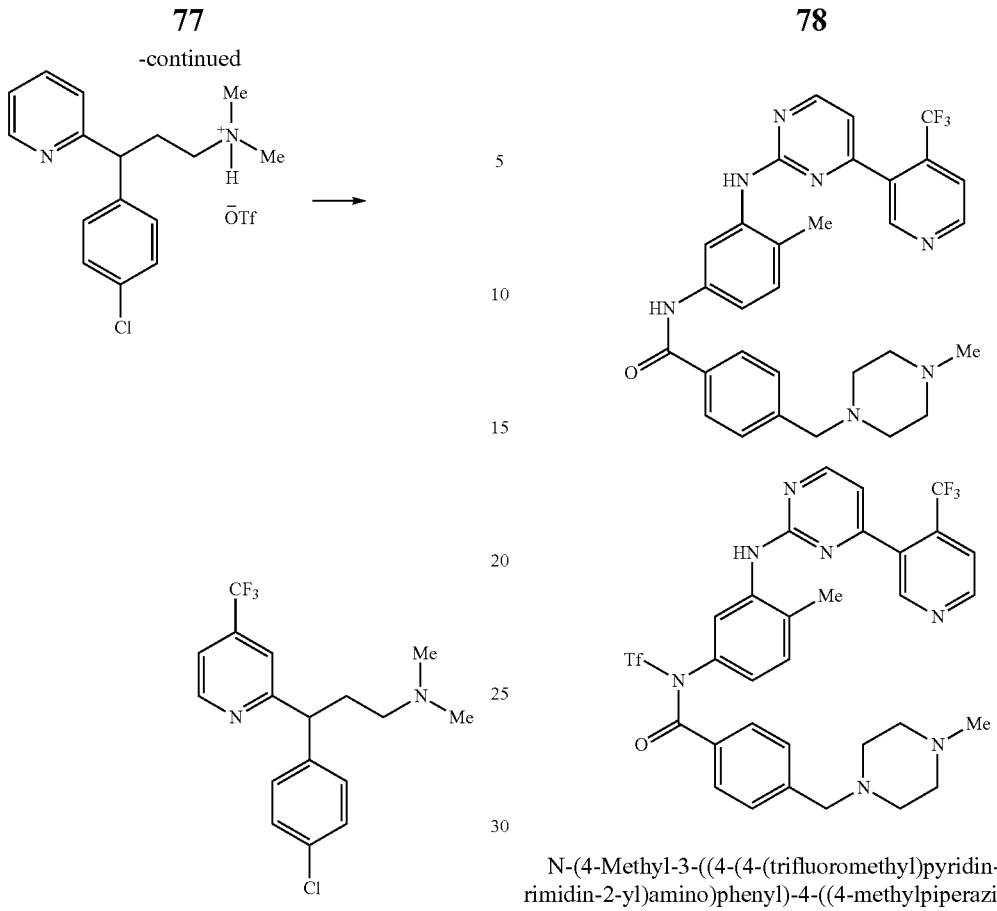

3-(4-Chlorophenyl)-N,N-dimethyl-3-(4-(trifluoromethyl)pyridin-2-yl)propan-1-amine (83). 4-chlorophenyl)-N,N-dimethyl-3-(pyridin-2-yl)propan-1-amine (55 mg, 0.20 mmol) was dissolved in Et$_2$O (1 mL) and cooled to 0° C. Trifluoromethanesulfonic acid (18 µL, 0.20 mmol) was added dropwise, the ice bath was removed, and the solution was stirred for 10 minutes at room temperature. The solution was concentrated in vacuo and the resulting acid salt was subjected to general procedure A (except that after Tf$_2$O added, the reaction mixture was stirred for 1 hour at −50° C.) using 1,1'-(((trifluoromethyl)phosphanediyl)bis(4,1-phenylene)) dipyrrolidine (86 mg, 0.22 mmol), Tf$_2$O (34 µL, 0.20 mmol), DBU (60 µL, 0.40 mmol), CH$_2$Cl$_2$ (2 mL), HOTf (44 µL, 0.50 mmol), MeOH (1 mL) and H$_2$O (36 µL, 2.00 mmol) at rt for 12 hours. The crude material was purified by flash chromatography (silica gel: 5% Et$_3$N in EtOAc) to provide the title compound as a light-yellow oil (52 mg, 0.15 mmol, 76% yield). $^1$H NMR (400 MHz, CDCl$_3$) δ: 8.75 (d, J=5.2 Hz, 1H), 7.37-7.26 (m, 6H), 4.25-4.22 (m, 1H), 2.48-2.36 (m, 1H), 2.26-2.15 (m, 9H); $^{13}$C NMR (100 MHz, CDCl$_3$) δ:164.86, 150.54, 141.35, 138.80 (q, J=33.7 Hz), 132.73, 129.57, 128.91, 122.93 (q, J=271.6 Hz), 118.64 (q, J=3.7 Hz), 117.22 (q, J=3.5 Hz), 57.45, 50.57, 45.52, 33.05; $^{19}$F NMR (376 MHz, CDCl$_3$) δ: −64.75; IR ν$_{max}$/cm$^{-1}$ (film): 2943, 2858, 2817, 2767, 1609, 1570, 1490, 1460, 1403, 1328, 1264, 1238, 1167, 1135, 1088, 1043, 1014, 895, 842, 828, 744, 721, 667; HRMS (DART): [M+H]$^+$ calculated for C$_{17}$H$_{19}$ClF$_3$N$_2$$^+$=343.1183, found 343.1187.

N-(4-Methyl-3-((4-(4-(trifluoromethyl)pyridin-3-yl)pyrimidin-2-yl)amino)phenyl)-4-((4-methylpiperazin-1-yl)methyl)benzamide (84). An oven dried 8 mL vial with a stir bar was charged with N-(4-methyl-3-((4-(pyridin-3-yl)pyrimidin-2-yl)amino)phenyl)-4-((4-methylpiperazin-1-yl)methyl)benzamide (74 mg, 0.15 mmol) and placed under a nitrogen atmosphere. CH$_2$Cl$_2$ (3.8 mL) was added, the reaction vessel cooled to −78° C. and Tf$_2$O (26 µL, 0.15 mmol) was added dropwise over 5 minutes. The reaction was stirred for 2 hours before 1,1'-(((trifluoromethyl)phosphanediyl)bis(4,1-phenylene)) dipyrrolidine (65 mg, 0.17 mmol) was added in one portion. The reaction was subjected to three rapid cycles of vacuum/nitrogen backfill and was stirred for a further 1 hour at −50° C. The DBU (23 L, 0.15 mmol) was added dropwise via syringe at the same temperature and stirred for another 2 hours. Then HOTf (47 µL, 0.53 mmol), MeOH (0.75 mL) and H$_2$O (27 µL, 1.50 mmol) were added sequentially at −50° C., the cooling bath was removed and the reaction was allowed to warm to room temperature for stirring further 5 hours. The reaction was quenched with a saturated aqueous solution of NaHCO$_3$ and extracted with CH$_2$Cl$_2$ (3×). The combined organic extracts were washed with a saturated aqueous solution of brine, dried (Na$_2$SO$_4$), filtered and concentrated in vacuo. The crude material was purified by flash chromatography (silica gel: 30% toluene, 3% MeOH and 2% Et$_3$N in CH$_2$Cl$_2$) to provide the mixture of compounds as a yellow oil (36 mg, 0.06 mmol, 42% yield). Major, $^1$H NMR (400 MHz, CDCl$_3$) δ: 8.87-8.86 (m, 2H), 8.52 (d, J=5.0 Hz, 1H), 8.25 (s, 1H), 7.89 (s, 1H), 7.80 (d, J=8.1 Hz, 1H), 7.64 (d, J=5.2 Hz, 1H), 7.50 (dd, J=2.2, 8.1 Hz, 1H), 7.42 (d, J=8.0 Hz, 1H), 7.18 (d, J=8.2 Hz, 1H), 7.10 (s, 1H), 6.87 (d, J=5.0 Hz, 1H), 3.55 (s, 2H), 2.47 (br s, 8H), 2.30-2.29 (m, 6H); Major, $^{13}$C (100 MHz, CDCl$_3$) δ: 165.61, 163.29, 160.37, 158.67, 151.87, 151.21, 142.60, 137.38, 136.70, 135.71 (d, J=32.6 Hz), 133.97, 132.11 (q, J=2.0 Hz), 130.99, 129.37, 127.13, 124.94, 122.77 (q, J=273.2 Hz), 119.95 (d, J=4.9 Hz), 116.18, 113.74, 112.58, 62.61, 55.18, 53.18, 46.08, 17.64; Major, $^{19}$F NMR (376 MHz, CDCl$_3$) δ: −59.03; IR $v_{max}$/cm$^{-1}$ (film): 3246, 2937, 2801, 1656, 1572, 1505, 1449, 1402, 1316, 1185, 1136, 1066, 1009, 908, 815, 727, 660, 613; m/z LRMS (ESI+APCI): [M+H]$^+$ calculated for C$_{30}$H$_{31}$F$_3$N$_7$O$^+$=562.3, found 562.3.

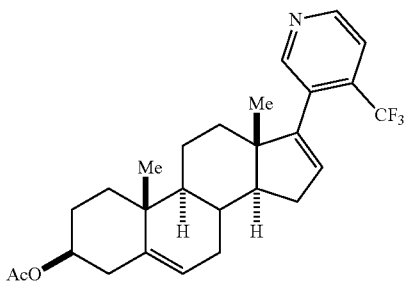

(3S,9S,10R,13S,14S)-10,13-Dimethyl-17-(4-(trifluoromethyl)pyridin-3-yl)-2,3,4,7,8,9,10,11,12,13,14,15-dodecahydro-1H-cyclopenta[a]phenanthren-3-yl acetate (86). Prepared according to general procedure A using (3S,9S,10R,13S,14S)-10,13-dimethyl-17-(pyridin-3-yl)-2,3,4,7,8,9,10,11,12,13,14,15-dodecahydro-1H-cyclopenta[a]phenanthren-3-yl acetate (78 mg, 0.20 mmol), 1,1'-(((trifluoromethyl)phosphanediyl)bis(4,1-phenylene))dipyrrolidine (86 mg, 0.22 mmol), Tf$_2$O (34 μL, 0.20 mmol), DBU (30 μL, 0.20 mmol), CH$_2$Cl$_2$ (2 mL), HOTf (18 μL, 0.20 mmol), TBAF (0.2 mL, 0.20 mmol, 1M in THF) at rt for 24 hours. The crude material was purified by flash chromatography (silica gel: 20% EtOAc in hexanes) to provide the title compound as a white solid (51 mg, 0.11 mmol, 55% yield). mp 145-148° C.; $^1$H NMR (400 MHz, CDCl$_3$) δ: 8.64-8.61 (m, 2H), 7.53 (d, J=5.0 Hz, 1H), 5.81 (s, 1H), 5.41 (d, J=5.1 Hz, 1H), 4.64-4.56 (m, 1H), 2.37-2.69 (m, 3H), 2.14-2.01 (m, 5H), 1.88-1.44 (m, 10H), 1.18-1.04 (m, 8H); $^{13}$C NMR (100 MHz, CDCl$_3$) δ: 170.64, 151.30, 148.59, 147.95, 140.13, 136.59 (q, J=30.5 Hz), 133.13 (q, J=2.5 Hz), 131.89, 123.01 (q, J=273.2 Hz), 122.40, 119.97 (q, J=4.9 Hz), 73.97, 57.06, 50.36, 49.67, 38.24, 37.02, 36.93, 34.56, 32.57, 31.65, 30.83, 27.84, 21.53, 20.77, 19.34, 17.10; $^{19}$F NMR (376 MHz, CDCl$_3$) δ: −58.61; IR $v_{max}$/cm$^{-1}$ (film): 3060, 2941, 2912, 2853, 2836, 1731, 1724, 1597, 1429, 1402, 1368, 1317, 1291, 1236, 1181, 1152, 1135, 1061, 1036, 963, 876, 839, 821, 808, 739, 653; HRMS (DART): [M+H]$^+$ calculated for C$_{27}$H$_{33}$F$_3$NO$_2^+$=460.2458, found 460.2446.

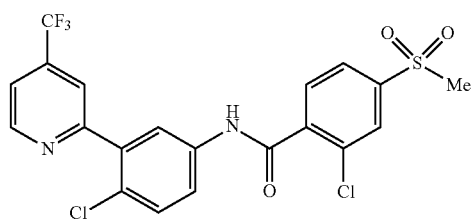 [SMILES: CS(=O)(=O)c1ccc(C(=O)Nc2ccc(Cl)c(-c3cc(C(F)(F)F)ccn3)c2)c(Cl)c1]

2-Chloro-N-(4-chloro-3-(4-(trifluoromethyl)pyridin-2-yl)phenyl)-4-(methylsulfonyl)benzamide (87). Prepared according to general procedure A (except that after Tf$_2$O added, the reaction mixture was stirred for 1 hour at −50° C.) using 2-chloro-N-(4-chloro-3-(pyridin-2-yl)phenyl)-4-(methylsulfonyl)benzamide (84 mg, 0.20 mmol), 1,1'-(((trifluoromethyl)phosphanediyl)bis(4,1-phenylene))dipyrrolidine (86 mg, 0.22 mmol), Tf$_2$O (34 μL, 0.20 mmol), DBU (30 μL, 0.20 mmol), CH$_2$Cl$_2$ (2 mL), HOTf (27 μL, 0.30 mmol), MeOH (1 mL) and H$_2$O (36 μL, 2.00 mmol) at rt for 12 hours. The crude material was purified by flash chromatography (silica gel: 20% EtOAc in CH$_2$Cl$_2$ to 25% EtOAc in CH$_2$Cl$_2$) to provide the title compound as a white solid (75 mg, 0.15 mmol, 76% yield). mp 147-149° C.; $^1$H NMR (400 MHz, CDCl$_3$) δ: 8.90 (s, 1H), 8.82 (d, J=5.2 Hz, 1H), 7.92-7.90 (m, 2H), 7.83 (t, J=1.1 Hz, 1H), 7.76 (dd, J=2.7, 8.7 Hz, 1H), 7.70 (d, J=1.1 Hz, 2H), 7.52 (dd, J=0.9, 5.1 Hz, 1H), 7.48 (d, J=8.7 Hz, 1H), 3.03 (s, 3H); $^{13}$C NMR (100 MHz, CDCl$_3$) δ: 163.68, 157.54, 150.49, 142.63, 140.62, 138.61 (q, J=34.1 Hz), 138.24, 136.83, 132.51, 131.09, 130.50, 128.97, 127.90, 125.86, 123.04, 122.77 (q, J=271.8 Hz), 122.16, 120.84 (q, J=3.8 Hz), 118.46 (q, J=3.4 Hz), 44.48; $^{19}$F NMR (376 MHz, CDCl$_3$) δ: −64.70; IR $v_{max}$/cm$^{-1}$ (film): 3299, 3066, 3025, 2926, 1675, 1605, 1584, 1534, 1485, 1462, 1430, 1371, 1335, 1301, 1280, 1246, 1211, 1167, 1150, 1137, 1098, 1084, 1049, 1032, 965, 883, 851, 817, 795, 757, 725, 667, 642, 591, 559; HRMS (DART): [M+H]$^+$ calculated for C$_{20}$H$_{14}$Cl$_2$F$_3$N$_2$O$_3$S$^+$=489.0049, found 489.0062.

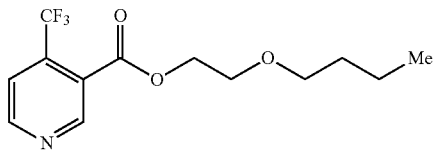 [SMILES: CCCCOCCOC(=O)c1cnccc1C(F)(F)F]

2-Butoxyethyl 4-(trifluoromethyl)nicotinate. Prepared according to general procedure B (except that after Tf$_2$O added, the reaction mixture was stirred for 1 hour at −30° C.) using 2-butoxyethyl nicotinate (45 mg, 0.20 mmol), 1,1'-(((trifluoromethyl)phosphanediyl)bis(4,1-phenylene))dipyrrolidine (86 mg, 0.22 mmol), Tf$_2$O (34 μL, 0.20 mmol), DBU (30 μL, 0.20 mmol), CH$_2$Cl$_2$ (2 mL), NaHCO$_3$ (50 mg, 0.60 mmol), THF (1 mL) and H$_2$O (36 μL, 2.00 mmol) at rt for 50 minutes. The crude material was purified by flash chromatography (silica gel: 20% EtOAc in hexanes) to provide the title compound as a light-yellow oil (45 mg, 0.16 mmol, 77% yield). $^1$H NMR (400 MHz, CDCl$_3$) δ: 9.10 (s, 1H), 8.90 (d, J=5.2 Hz, 1H), 7.63 (d, J=5.2 Hz, 1H), 4.50 (t, J=4.8 Hz, 1H), 3.73 (t, J=4.8 Hz, 1H), 3.48 (t, J=6.6 Hz, 1H), 1.59-1.52 (m, 2H), 1.40-1.30 (m, 2H), 0.89 (t, J=7.4 Hz, 3H); $^{13}$C NMR (100 MHz, CDCl$_3$) δ: 164.60, 153.31, 151.72, 136.79 (q, J=34.2 Hz), 125.39 (q, J=1.9 Hz), 122.17 (q, J=272.9 Hz), 120.22 (q, J=5.0 Hz), 71.31, 68.20, 65.61, 31.74, 19.30, 13.94; $^{19}$F NMR (376 MHz, CDCl$_3$) δ: −61.73; IR $v_{max}$/cm$^{-1}$ (film): 2959, 2934, 2870, 1739, 1593, 1458, 1405, 1383, 1306, 1265, 1232, 1145, 1067, 1050, 844, 790, 660, 612; m/z HRMS (DART): [M+H]$^+$ calculated for C$_{13}$H$_{17}$F$_3$NO$_3^+$=292.1155, found 292.1161.

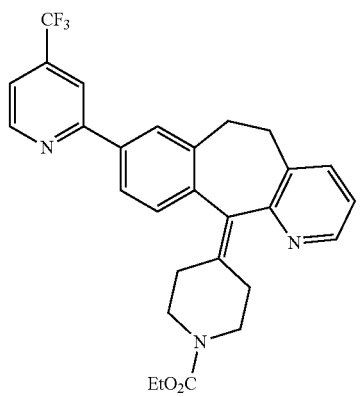 [SMILES: CCOC(=O)N1CCC(=C2c3ccc(-c4cc(C(F)(F)F)ccn4)cc3CCc3cccnc32)CC1]

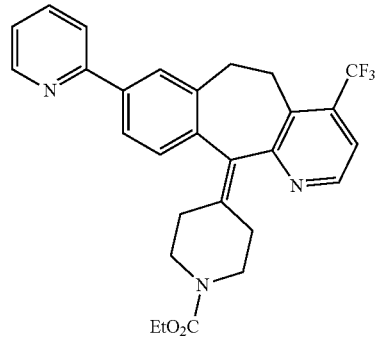 [SMILES: CCOC(=O)N1CCC(=C2c3ccc(-c4ccccn4)cc3CCc3c(C(F)(F)F)ccnc32)CC1]

Ethyl 4-(8-(4-(trifluoromethyl)pyridin-2-yl)-5,6-dihydro-7-benzo[5,6]cyclohepta[1,2-b]pyridin-11-ylidene)piperidine-1-carboxylate. An oven dried 8 mL vial with a stir bar was charged with ethyl 4-(8-(pyridin-2-yl)-5,6-dihydro-11H-benzo[5,6]cyclohepta[1,2-b]pyridin-11-ylidene)piperidine-1-carboxylate (85 mg, 0.20 mmol) and placed under a nitrogen atmosphere. CH$_2$Cl$_2$ (3.8 mL) was added, the reaction vessel cooled to −78° C. and Tf$_2$O (68 μL, 0.40 mmol) was added dropwise over 5 minutes. The reaction was stirred for 30 minutes before 1,1'-(((trifluoromethyl)phosphanediyl)bis(4,1-phenylene))dipyrrolidine (157 mg, 0.40 mmol) was added in one portion. The reaction was subjected to three rapid cycles of vacuum/nitrogen backfill and was stirred for a further 30 minutes at −78° C. The Et$_3$N (56 μL, 0.40 mmol) was added dropwise via syringe, the cooling bath was removed and the reaction was allowed to warm to room temperature while stirring (approximately 15 minutes). Then, the reaction mixture was cooled to 0° C., HOTf (45 μL, 0.5 mmol), MeOH (1 mL) and H$_2$O (36 μL, 2.00 mmol) were added sequentially. The mixture was warmed to room temperature and stirred for 12 hours. The reaction was quenched with a saturated aqueous solution of NaHCO$_3$ and extracted with CH$_2$Cl$_2$ (3×). The combined organic extracts were washed with a saturated aqueous solution of brine, dried (Na$_2$SO$_4$), filtered and concentrated in vacuo. The crude material was purified by flash chromatography (silica gel: 33% EtOAc, 10% Et$_3$N in hexanes) to provide the title compound as a light-yellow oil (72 mg, 0.15 mmol, 73% yield). $^1$H NMR (400 MHz, CDCl$_3$) δ: 8.83 (d, J=5.1 Hz, 1H), 8.41 (dd, J=1.7, 4.8 Hz, 1H), 7.88 (s, 2H), 7.79 (dd, J=2.0, 8.0 Hz, 1H), 7.45 (dd, J=1.7, 7.7 Hz, 1H), 7.42 (dd, J=0.7, 5.0 Hz, 1H), 7.33 (d, J=8.0 Hz, 1H), 7.10 (dd, J=4.8, 7.7 Hz, 1H), 4.13 (q, J=7.1 Hz, 2H), 3.83 (br s, 2H), 3.55-3.47 (m, 1H), 3.44-3.36 (m, 1H), 3.19-3.12 (m, 2H), 2.99-2.87 (m, 2H), 2.55-2.48 (m, 1H), 2.42-2.32 (m, 3H), 1.24 (t, J=7.1 Hz, 3H); $^{13}$C NMR (100 MHz, CDCl$_3$) δ: 158.55, 157.13, 155.61, 150.71, 146.79, 141.19, 139.20 (q, J=33.7 Hz), 138.69, 137.66, 137.59, 137.23, 134.90, 133.70, 130.05, 127.83, 124.80, 123.02 (q, J=271.6 Hz), 122.35, 117.56 (q, J=3.6 Hz), 115.98 (q, J=3.7 Hz), 61.40, 44.95, 44.93, 32.04, 31.83, 30.95, 30.67, 14.78; $^{19}$F NMR (376 MHz, CDCl$_3$) δ: −64.84; IR ν$_{max}$/cm$^{-1}$ (film): 2911, 1690, 1608, 1570, 1471, 1423, 1384, 1333, 1277, 1227, 1168, 1134, 1113, 1088, 1059, 1026, 996, 889, 835, 790, 766, 726, 666; HRMS (DART): [M+H]$^+$ calculated for C$_{28}$H$_{27}$F$_3$N$_3$O$_2$$^+$=494.2050, found 494.2084.

Ethyl 4-(8-(pyridin-2-yl)-4-(trifluoromethyl)-5,6-dihydro-11H-benzo[5,6]cyclohepta[1,2-b]pyridin-11-ylidene)piperidine-1-carboxylate. Prepared according to general procedure A using ethyl 4-(8-(pyridin-2-yl)-5,6-dihydro-11H-benzo[5,6]cyclohepta[1,2-b]pyridin-11-ylidene)piperidine-1-carboxylate (85 mg, 0.20 mmol), 1,1'-(((trifluoromethyl)phosphanediyl)bis(4,1-phenylene))dipyrrolidine (79 mg, 0.20 mmol), Tf$_2$O (34 μL, 0.20 mmol), DBU (30 μL, 0.20 mmol), CH$_2$Cl$_2$ (2 mL), HOTf (45 μL, 0.50 mmol), MeOH (1 mL) and H$_2$O (36 μL, 2.00 mmol) at rt for 12 hours. The crude material was purified by flash chromatography (silica gel: 33% EtOAc, 10% Et$_3$N in hexanes) to provide the title compound as a colorless oil (70 mg, 0.14 mmol, 71% yield). $^1$H NMR (400 MHz, CDCl$_3$) δ: 8.65 (d, J=4.6 Hz, 1H), 8.56 (d, J=5.1 Hz, 1H), 7.78 (s, 1H), 7.74-7.65 (m, 3H), 7.40 (d, J=5.2 Hz, 1H), 7.29 (d, J=8.0 Hz, 1H), 7.21-7.18 (m, 1H), 4.14 (q, J=7.1 Hz, 2H), 3.83-3.80 (m, 2H), 3.56-3.42 (m, 2H), 3.30-3.16 (m, 3H), 3.11-3.02 (m, 1H), 2.55-2.52 (m, 2H), 2.44-2.37 (m, 1H), 2.18-2.12 (m, 1H), 1.25 (t, J=7.1 Hz, 3H); $^{13}$C NMR (100 MHz, CDCl$_3$) δ: 162.61, 156.86, 155.57, 149.76, 147.56, 138.84, 137.48, 137.00, 136.92, 136.83, 136.27 (q, J=31.1 Hz), 134.42, 131.62, 131.04, 128.98, 124.45, 123.37 (q, J=273.2 Hz), 122.28, 120.47, 118.46 (q, J=5.1 Hz), 61.45, 44.95, 44.70, 32.15, 30.88, 30.69, 26.45, 14.76; $^{19}$F NMR (376 MHz, CDCl$_3$) δ: −61.86; IR ν$_{max}$/cm$^{-1}$ (film): 2911, 2868, 1708, 1585, 1484, 1463, 1431, 1407, 1328, 1302, 1279, 1215, 1149, 1122, 1065, 1028, 1000, 985, 893, 857, 781, 759, 736, 687; HRMS (DART): [M+H]$^+$ calculated for C$_{28}$H$_{27}$F$_3$N$_3$O$_2$$^+$=494.2050, found 494.2080.

Example 5. Difluoromethylation of Heterocycles

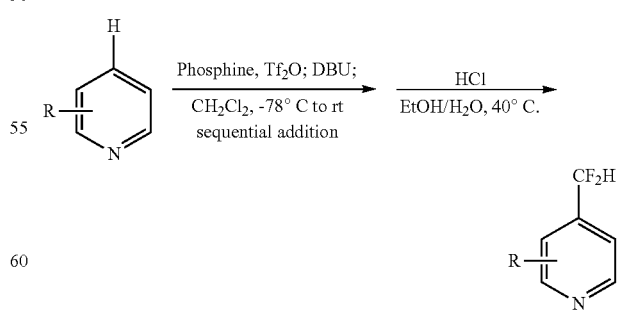

General Procedure A. An oven dried mL via or 25-mL round bottom as was charged with the heterocycle (1.0 equiv) and phosphine (1.1 equiv) and placed under a nitrogen atmosphere. CH$_2$Cl$_2$ (0.1 M) was added, the reaction vessel cooled to −78° C. and Tf$_2$O (1.0 equiv) was added dropwise over 5 minutes. The reaction was stirred for 30 minutes before DBU (1.0 equiv) was added dropwise (note—addition should be performed with vigorous stirring to ensure the DBU is readily homogenized; at −78° C. it tends to freeze and stick to the stir bar, preventing stirring). After the addition was complete, the reaction was warmed to 0° C. in an ice bath over 5 minutes. A 10% H$_2$O in EtOH (v/v) solution was added to the reaction, bringing the final concentration to 0.05 M, and HCl in dioxane was added (1.0 equiv). The reaction was heated to 40° C. and allowed to run for 24 h, then quenched with a saturated aqueous solution of NaHCO$_3$ and the aqueous layer was extracted with CH$_2$Cl$_2$ (3×). The combined organic extracts were washed with a saturated aqueous solution of brine, dried (MgSO$_4$), filtered, and concentrated in vacuo. The residue was purified by flash column chromatography to provide the difluoromethylated heteroarene.

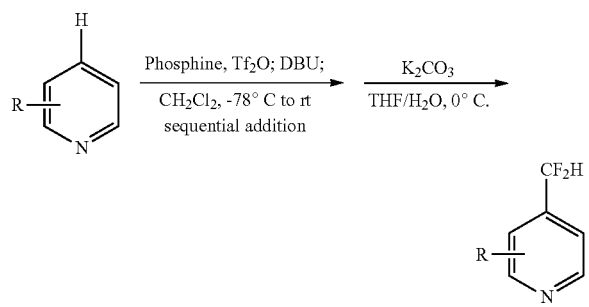

General Procedure B. An oven dried 8 mL vial or 25 mL round bottom flask was charged with the heterocycle (1.0 equiv) and phosphine (1.1 equiv) and placed under a nitrogen atmosphere. CH$_2$Cl$_2$ (0.1 M) was added, the reaction vessel cooled to −78° C. and Tf$_2$O (1.0 equiv) was added dropwise over 5 minutes. The reaction was stirred for 30 minutes before DBU (1.0 equiv) was added dropwise (note—addition should be performed with vigorous stirring to ensure the DBU is readily homogenized; at −78° C. it tends to freeze and stick to the stir bar, preventing stirring). After the addition was complete, the reaction was warmed to 0° C. in an ice bath over 5 minutes. The solvent was removed under vacuum, and THF and H$_2$O (1:1, 0.1 M) were added to the residue. The solution was vigorously stirred and solid K$_2$CO$_3$ (1.5 eq.) was added in one portion. After 1 h, the reaction mixture was extracted with CH$_2$Cl$_2$ (3×). The combined organic extracts were washed with a saturated aqueous solution of brine, dried (MgSO$_4$), filtered, and concentrated in vacuo. The residue was purified by flash column chromatography to provide the difluoromethylated heteroarene.

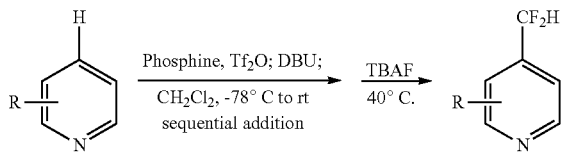

General Procedure C. An oven dried 8 mL vial or 25 mL round bottom flask was charged with the heterocycle (1.0 equiv) and phosphine (1.1 equiv) and placed under a nitrogen atmosphere. CH$_2$Cl$_2$ (0.1 M) was added, the reaction vessel cooled to −78° C. and Tf$_2$O (1.0 equiv) was added dropwise over 5 minutes. The reaction was stirred for 30 minutes before DBU (1.0 equiv) was added dropwise (note—addition should be performed with vigorous stirring to ensure the DBU is readily homogenized; at −78° C. it tends to freeze and stick to the stir bar, preventing stirring). After the addition was complete, the reaction was warmed to 0° C. in an ice bath over 5 minutes. HCl in dioxane was added (1.0 equiv), followed by TBAF (1.0 equiv.), and the reaction was heated to 40° C. for 24 h, then quenched with a saturated aqueous solution of NaHCO$_3$ and the aqueous layer was extracted with CH$_2$Cl$_2$ (3×). The combined organic extracts were washed with a saturated aqueous solution of brine, dried (MgSO$_4$), filtered, and concentrated in vacuo. The residue was purified by flash column chromatography to provide the difluoromethylated heteroarene.

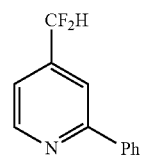

4-(difluoromethyl)-2-phenylpyridine (15). Prepared according to general procedure A using 2-phenylpyridine (71.5 μL, 0.5 mmol), (difluoromethyl)bis(4-methoxyphenyl)phosphane (163 mg, 0.55 mmol), Tf$_2$O (84 μL, 0.5 mmol), DBU (75 μL, 0.5 mmol), CH$_2$Cl$_2$ (5 mL), HCl (4 M in dioxane, 125 μL, 0.5 mmol), EtOH (4.5 mL) and H$_2$O (0.5 mL) at 40° C. for 24 hours. The crude material was purified by flash chromatography (silica gel: 60% CH$_2$Cl$_2$ in hexanes) to provide the title compound as a colorless oil (83 mg, 0.40 mmol, 80% yield). $^1$H NMR (400 MHz, CDCl$_3$) δ: 8.81 (d, J=5.3 Hz, 1H), 8.09-7.91 (m, 2H), 7.84 (s, 1H), 7.60-7.39 (m, 3H), 7.39-7.31 (m, 1H), 6.69 (t, J=55.8 Hz, 1H); $^{13}$C NMR (100 MHz, CDCl$_3$) δ: 158.43, 150.38, 142.97 (t, J=23.3 Hz), 138.48, 129.57, 128.90, 127.00, 118.20 (t, J=5.7 Hz), 116.62 (t, J=6.0 Hz), 113.14 (t, J=240.9 Hz); $^{19}$F NMR (376 MHz, CDCl$_3$) δ: −115.56 (d, J=55.8 Hz). IR ν$_{max}$/cm$^{-1}$ (film): 3054, 2360, 1609, 1583, 1564, 1476, 1409, 1380, 1302, 1198, 1114, 1038, 837, 774, 692, 635, 548. m/z HRMS (DART): [M+H]$^+$ calculated for C$_{12}$H$_{10}$F$_2$N$^+$=206.0776, found 206.0792.

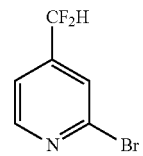

2-bromo-4-(difluoromethyl)pyridine (35). Prepared according to general procedure B using 2-bromopyridine (48.6 μL, 0.5 mmol), (difluoromethyl)bis(4-methoxyphenyl)phosphane (163 mg, 0.55 mmol), Tf$_2$O (84 μL, 0.5 mmol), DBU (75 μL, 0.5 mmol), CH$_2$Cl$_2$ (5 mL), K$_2$CO$_3$ (69 mg, 0.5 mmol), THF (2.5 mL) and H$_2$O (2.5 mL) at rt for 16 hours. The crude material was purified by flash chromatography (silica gel: 75% CH$_2$Cl$_2$ in hexanes) to provide the title compound as a colorless oil (68 mg, 0.33 mmol, 65% iso. yield, 78% $^1$H NMR yield). Note that the product evaporates during solvent evaporation. $^1$H NMR (400 MHz, CDCl$_3$) δ: 8.51 (d, J=5.1 Hz, 1H), 7.62 (s, 1H), 7.38 (d, J=5.1 Hz, 1H), 6.60 (t, J=55.4 Hz, 1H); $^{13}$C NMR (100 MHz, CDCl$_3$) δ: 151.09, 144.83 (t, J=23.7 Hz), 142.91, 124.87 (t, J=6.2 Hz), 119.17 (t, J=5.6 Hz), 112.01 (t, J=242.2 Hz); $^{19}$F NMR (376 MHz, CDCl$_3$) δ: −116.15 (d, J=55.4 Hz). IR $\nu_{max}$/cm$^{-1}$ (film): 3067, 2979, 1598, 1557, 1464, 1397, 1363, 1286, 1218, 1125, 1078, 1043, 830, 739, 708, 671. m/z LRMS (ESI+APCI): [M]$^+$ calculated for C$_6$H$_4$BrF$_2$N=208.0, found 208.0.

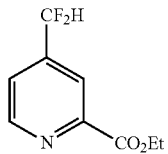

ethyl 4-(difluoromethyl)picolinate (36). Prepared according to general procedure A using ethyl picolinate (67.5 μL, 0.5 mmol), (difluoromethyl)bis(4-methoxyphenyl)phosphane (163 mg, 0.55 mmol), Tf$_2$O (84 μL, 0.5 mmol), DBU (75 μL, 0.5 mmol), CH$_2$Cl$_2$ (5 mL), HCl (4 M in dioxane, 125 μL, 0.5 mmol), EtOH (4.5 mL) and H$_2$O (0.5 mL) at 40° C. for 24 hours. The crude material was purified by flash chromatography (silica gel: 30% EtOAc in hexanes) to provide the title compound as a colorless oil (67 mg, 0.33 mmol, 67% yield). $^1$H NMR (400 MHz, CDCl$_3$) δ: 8.88 (d, J=4.6 Hz, 1H), 8.23 (s, 1H), 7.59 (d, J=4.0 Hz, 1H), 6.69 (t, J=55.4 Hz, 1H), 4.49 (q, J=7.1 Hz, 2H), 1.44 (t, J=7.1 Hz, 3H); $^{13}$C NMR (100 MHz, CDCl$_3$) δ: 164.53, 150.74, 149.37, 143.62 (t, J=23.9 Hz), 123.02 (t, J=5.7 Hz), 121.63 (t, J=6.0 Hz), 112.56 (t, J=241.6 Hz), 62.47, 14.40; $^{19}$F NMR (376 MHz, CDCl$_3$) δ: −115.95 (d, J=55.5 Hz). IR $\nu_{max}$/cm$^{-1}$ (film): 2985, 2940, 2360, 1720, 1609, 1471, 1367, 1300, 1275, 1206, 1131, 1040, 1022, 913, 863, 783, 668. m/z HRMS (DART): [M+H]$^+$ calculated for C$_9$H$_{10}$F$_2$NO$_2$$^+$=202.0674, found 202.0689.

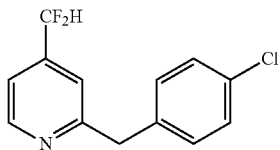 [SMILES: FC(F)c1ccnc(Cc2ccc(Cl)cc2)c1]

2-(4-chlorobenzyl)-4-(difluoromethyl)pyridine (37). Prepared according to general procedure A using 2-(4-chlorobenzyl)pyridine (74 μL, 0.5 mmol), (difluoromethyl)bis(4-methoxyphenyl)phosphane (163 mg, 0.55 mmol), Tf$_2$O (84 μL, 0.5 mmol), DBU (75 μL, 0.5 mmol), CH$_2$Cl$_2$ (5 mL), HCl (4 M in dioxane) (125 μL, 0.5 mmol), EtOH (4.5 mL) and H$_2$O (0.5 mL) at 40° C. for 24 hours. The crude material was purified by flash chromatography (silica gel: 5% EtOAc in CH$_2$Cl$_2$) to provide the title compound as a colorless oil (104 mg, 0.41 mmol, 82% yield). $^1$H NMR (400 MHz, CDCl$_3$) δ: 8.68 (d, J=5.1 Hz, 1H), 7.34-7.24 (m, 3H), 7.24-7.13 (m, 3H), 6.58 (t, J=55.7 Hz, 1H), 4.18 (s, 2H); $^{13}$C NMR (100 MHz, CDCl$_3$) δ: 161.68, 150.37, 142.98 (t, J=23.3 Hz), 137.35, 132.71, 130.57, 128.99, 119.29 (t, J=5.9 Hz), 117.83 (t, J=5.7 Hz), 113.06 (t, J=240.9 Hz), 44.07; $^{19}$F NMR (376 MHz, CDCl$_3$) δ: −115.63 (d, J=55.7 Hz). IR $\nu_{max}$/cm$^{-1}$ (film): 3028, 2928, 2360, 2341, 2222, 1611, 1570, 1491, 1407, 1365, 1174, 1089, 1043, 1016, 907, 848, 797, 729, 686. m/z HRMS (DART): [M+H]$^+$ calculated for C$_{13}$H$_{11}$ClF$_2$N$^+$=254.0543, found 254.0563.

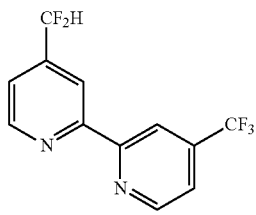 [SMILES: FC(F)c1ccnc(-c2cc(C(F)(F)F)ccn2)c1]

4-(difluoromethyl)-4'-(trifluoromethyl)-2,2'-bipyridine (38). Prepared according to general procedure A using 4-(trifluoromethyl)-2,2'-bipyridine (112 mg, 0.5 mmol), (difluoromethyl)bis(4-methoxyphenyl)phosphane (163 mg, 0.55 mmol), Tf$_2$O (84 μL, 0.5 mmol), DBU (75 μL, 0.5 mmol), CH$_2$Cl$_2$ (5 mL), HCl (4 M in dioxane, 125 μL, 0.5 mmol), EtOH (4.5 mL) and H$_2$O (0.5 mL) at 60° C. for 72 hours. The crude material was purified by flash chromatography (silica gel: 3% EtOAc in CH$_2$Cl$_2$) to provide the title compound as a white solid (83 mg, 0.30 mmol, 60% yield). mp 74-75° C.; $^1$H NMR (400 MHz, CDCl$_3$) δ: 8.85 (dd, J=14.3, 4.2 Hz, 2H), 8.72 (s, 1H), 8.60 (s, 1H), 7.53 (dd, J=24.8, 4.5 Hz, 2H), 6.73 (t, J=55.6 Hz, 1H); $^{13}$C NMR (100 MHz, CDCl$_3$) δ: 156.70, 155.82, 150.29 (d, J=11.7 Hz), 143.62 (t, J=23.6 Hz), 139.69 (q, J=34.2 Hz), 124.39, 121.67, 121.18-120.39 (m), 119.82, 117.97 (t, J=6.3 Hz), 117.25 (d, J=3.7 Hz), 113.15 (t, J=241.1 Hz); $^{19}$F NMR (376 MHz, CDCl$_3$) δ: −64.85, −115.58 (d, J=55.7 Hz). IR $\nu_{max}$/cm$^{-1}$ (film): 3080, 2925, 2360, 2342, 1603, 1568, 1465, 1392, 1367, 1332, 1287, 1263, 1164, 1129, 1080, 1068, 1038, 908, 849, 667. m/z HRMS (DART): [M+H]$^+$ calculated for C$_{12}$H$_8$F$_5$N$_2$$^+$=275.0602, found 275.0608.

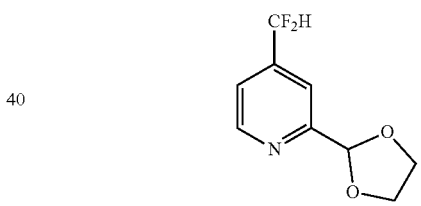

4-(difluoromethyl)-2-(1,3-dioxolan-2-yl)pyridine (39). Prepared according to general procedure C using 2-(1,3-dioxolan-2-yl)pyridine (76 mg, 0.5 mmol), (difluoromethyl)bis(4-methoxyphenyl)phosphane (163 mg, 0.55 mmol), Tf$_2$O (84 μL, 0.5 mmol), DBU (75 μL, 0.5 mmol), CH$_2$Cl$_2$ (5 mL), and TBAF (1 M in THF, 500 μL, 0.5 mmol), at 60° C. for 24 hours. The crude material was purified by flash chromatography (silica gel: 10% EtOAc in CH$_2$Cl$_2$) to provide the title compound as a colorless oil (68 mg, 0.34 mmol, 68% yield). $^1$H NMR (400 MHz, CDCl$_3$) δ: 8.74 (d, J=5.0 Hz, 1H), 7.66 (s, 1H), 7.40 (d, J=4.8 Hz, 1H), 6.64 (t, J=55.7 Hz, 1H), 5.89 (s, 1H), 4.23-4.04 (m, 3H); $^{13}$C NMR (100 MHz, CDCl$_3$) δ: 158.44, 150.22, 143.18 (t, J=23.5 Hz), 120.26 (t, J=5.7 Hz), 117.23 (t, J=6.0 Hz), 112.97 (t, J=241.2 Hz), 103.30, 65.80; $^{19}$F NMR (376 MHz, CDCl$_3$) δ: −115.73 (d, J=55.7 Hz). IR $\nu_{max}$/cm$^{-1}$ (film): 2962, 2893, 2360, 2341, 2252, 1614, 1383, 1173, 1119, 1080, 1041, 982, 907, 855, 728, 647. m/z HRMS (DART): [M+H]$^+$ calculated for C$_9$H$_{10}$F$_2$NO$_2$$^+$=202.0674, found 202.0687.

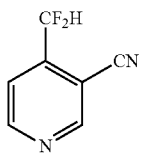

4-(difluoromethyl)nicotinonitrile (41). Prepared according to general procedure A using 3-cyanopyridine (52 mg, 0.5 mmol), (difluoromethyl)bis(4-methoxyphenyl)phosphane (163 mg, 0.55 mmol), Tf$_2$O (84 μL, 0.5 mmol), DBU (75 μL, 0.5 mmol), CH$_2$Cl$_2$ (5 mL), HCl (4 M in dioxane, 125 μL, 0.5 mmol), EtOH (4.5 mL) and H$_2$O (0.5 mL) at 40° C. for 24 hours. The crude material was purified by flash chromatography (silica gel: 2% EtOAc in CH$_2$Cl$_2$) to provide the title compound as a white solid (13 mg, 0.08 mmol, 17% iso. yield, 40% $^1$H NMR yield). Note that the product evaporates during solvent evaporation. $^1$H NMR (400 MHz, CDCl$_3$) δ: 9.02 (s, 1H), 8.98 (d, J=4.8 Hz, 1H), 7.68 (d, J=5.1 Hz, 1H), 6.89 (t, J=54.0 Hz, 1H); $^{13}$C NMR (100 MHz, CDCl$_3$) δ: 158.72, 147.33, 139.88 (t, J=21.5 Hz), 129.96, 117.17 (t, J=7.1 Hz), 112.61 (t, J=239.6 Hz), 33.05, 24.90, 22.52, 22.32; $^{19}$F NMR (376 MHz, CDCl$_3$) δ: −116.21 (d, J=54.0 Hz). IR $v_{max}$/cm$^{-1}$ (film): 3037, 2924, 2236, 1593, 1407, 1381, 1235, 1191, 1164, 1090, 1042, 836, 790, 734, 660. m/z LRMS (ESI-APCI): [M]$^+$ calculated for C$_7$H$_4$F$_2$N$_2$=154.0, found 154.0.

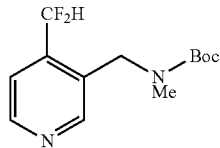 [SMILES: CN(Cc1cnccc1C(F)F)C(=O)OC(C)(C)C]

tert-butyl ((4-(difluoromethyl)pyridin-3-yl)methyl)(methyl)carbamate (42). Prepared according to general procedure A using tert-butyl methyl(pyridin-3-ylmethyl)carbamate (111 mg, 0.5 mmol), (difluoromethyl)bis(4-methoxyphenyl)phosphane (163 mg, 0.55 mmol), Tf$_2$O (84 μL, 0.5 mmol), DBU (75 μL, 0.5 mmol), CH$_2$Cl$_2$ (5 mL), HCl (4 M in dioxane, 125 μL, 0.5 mmol), EtOH (4.5 mL) and H$_2$O (0.5 mL) at 40° C. for 24 hours. The crude material was purified by flash chromatography (silica gel: 55% EtOAc in hexanes) to provide the title compound as a colorless oil (85 mg, 0.31 mmol, 62% yield). $^1$H NMR (400 MHz, CDCl$_3$) δ: 8.68 (d, J=5.0 Hz, 1H), 8.57 (s, 1H), 7.48 (d, J=5.0 Hz, 1H), 6.91 (br t, J=54.1 Hz, 1H), 4.58 (s, 2H), 2.82 (s, 3H), 1.45 (s, 9H); $^{13}$C NMR (100 MHz, CDCl$_3$) δ: 158.06-154.49 (m), 152.70-150.30 (m), 149.93, 141.44-138.84 (m), 130.85, 119.89, 112.22 (t, J=239.2 Hz), 80.67, 51.80-44.51 (m), 34.13, 29.82, 28.43; $^{19}$F NMR (376 MHz, CDCl$_3$) δ: −115.47 (d, J=53.3 Hz). IR $v_{max}$/cm$^{-1}$ (film): 2978, 2933, 2360, 2341, 1686, 1480, 1414, 1391, 1367, 1240, 1147, 1084, 1038, 980, 911, 730, 663. m/z HRMS (DART): [M+H]$^+$ calculated for C$_{13}$H$_{19}$F$_2$N$_2$O$_2$$^+$=273.1409, found 273.1417.

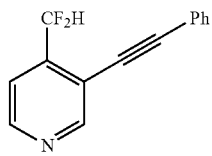 [SMILES: FC(F)c1ccncc1C#Cc1ccccc1]

4-(difluoromethyl)-3-(phenylethynyl)pyridine (43). Prepared according to general procedure A using 3-(phenylethynyl)pyridine (90 mg, 0.5 mmol), (difluoromethyl)bis(4-methoxyphenyl)phosphane (163 mg, 0.55 mmol), Tf$_2$O (84 μL, 0.5 mmol), DBU (75 μL, 0.5 mmol), CH$_2$Cl$_2$ (5 mL), HCl (4 M in dioxane, 125 μL, 0.5 mmol), EtOH (4.5 mL) and H$_2$O (0.5 mL) at 40° C. for 48 hours. The crude material was purified by flash chromatography (silica gel: 20% EtOAc in hexanes) to provide the title compound as a yellow solid (89 mg, 0.39 mmol, 78% yield). mp 44-45° C.; $^1$H NMR (400 MHz, CDCl$_3$) δ: 8.85 (s, 1H), 8.68 (d, J=5.1 Hz, 1H), 7.59-7.52 (m, 3H), 7.40 (qd, J=4.7, 1.6 Hz, 3H), 7.00 (t, J=54.7 Hz, 1H); $^{13}$C NMR (100 MHz, CDCl$_3$) δ: 153.21, 149.37, 142.40 (t, J=23.2 Hz), 131.90, 129.57, 128.70, 121.90, 119.01 (t, J=5.1 Hz), 118.44 (t, J=5.7 Hz), 111.98 (t, J=239.8 Hz), 98.26, 81.91; $^{19}$F NMR (376 MHz, CDCl$_3$) δ: −117.10 (d, J=54.7 Hz). IR $v_{max}$/cm$^{-1}$ (film): 3068, 3021, 3001, 2926, 2854, 2360, 2341, 2221, 1598, 1496, 1442, 1365, 1233, 1211, 1168, 1143, 1076, 1031, 869, 848, 825, 749, 720, 686, 664. m/z HRMS (DART): [M+H]$^+$ calculated for C$_{14}$H$_{10}$F$_2$N$^+$=230.0776, found 230.0787.

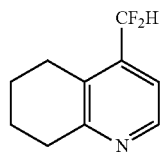 [SMILES: FC(F)c1ccnc2c1CCCC2]

4-(difluoromethyl)-5,6,7,8-tetrahydroquinoline (44). Prepared according to general procedure A using 5,6,7,8-tetrahydroquinoline (64.7 μL, 0.5 mmol), (difluoromethyl)bis(4-methoxyphenyl)phosphane (163 mg, 0.55 mmol), Tf$_2$O (84 μL, 0.5 mmol), DBU (75 μL, 0.5 mmol), CH$_2$Cl$_2$ (5 mL), HCl (4 M in dioxane) (125 μL, 0.5 mmol), EtOH (4.5 mL) and H$_2$O (0.5 mL) at 40° C. for 24 hours. The crude material was purified by flash chromatography (silica gel: 40% EtOAc in hexanes) to provide the title compound as a colorless oil (46 mg, 0.25 mmol, 50% yield). $^1$H NMR (400 MHz, CDCl$_3$) δ: 8.48 (d, J=5.0 Hz, 1H), 7.24 (d, J=5.0 Hz, 1H), 6.71 (t, J=54.7 Hz, 1H), 2.99 (t, J=6.2 Hz, 2H), 2.84 (t, J=6.1 Hz, 2H), 1.98-1.77 (m, 4H); $^{13}$C NMR (100 MHz, CDCl$_3$) δ: 158.56, 147.18, 139.72 (t, J=21.5 Hz), 129.80, 117.01 (t, J=7.1 Hz), 112.46 (t, J=239.6 Hz), 32.89, 24.74, 22.36, 22.17; $^{19}$F NMR (376 MHz, CDCl$_3$) δ: −117.77 (d, J=54.7 Hz). IR $v_{max}$/cm$^{-1}$ (film): 2941, 2864, 2360, 2341, 2213, 1574, 1438, 1412, 1374, 1263, 1249, 1232, 1112, 1036, 908, 872, 843, 728, 644. m/z HRMS (DART): [M+H]$^+$ calculated for C$_{10}$H$_{12}$F$_2$N$^+$=184.0932, found 184.0941.

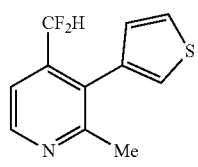 [SMILES: Cc1nccc(C(F)F)c1-c1ccsc1]

4-(difluoromethyl)-2-methyl-3-(thiophen-3-yl)pyridine (45). Prepared according to general procedure A using 2-methyl-3-(thiophen-3-yl)pyridine (87.6 mg, 0.5 mmol), (difluoromethyl)bis(4-methoxyphenyl)phosphane (163 mg, 0.55 mmol), Tf$_2$O (84 μL, 0.5 mmol), DBU (75 μL, 0.5 mmol), CH$_2$Cl$_2$ (5 mL), HCl (4 M in dioxane) (125 μL, 0.5 mmol), EtOH (4.5 mL) and H$_2$O (0.5 mL) at 60° C. for 72 hours. The crude material was purified by flash chromatography (silica gel: 25% EtOAc in hexanes) to provide the title compound as a colorless oil (86 mg, 0.38 mmol, 76% yield). $^1$H NMR (400 MHz, CDCl$_3$) δ: 8.63 (d, J=5.1 Hz, 1H), 7.56-7.37 (m, 2H), 7.22 (dd, J=2.9, 1.1 Hz, 1H), 7.01 (dd, J=4.9, 1.1 Hz, 1H), 6.29 (t, J=54.7 Hz, 1H), 2.39 (s, 3H); $^{13}$C NMR (100 MHz, CDCl$_3$) δ: 158.60, 148.98, 140.76 (t, J=22.8 Hz), 134.91, 130.22 (t, J=6.3 Hz), 128.80, 126.73, 125.17, 116.69 (t, J=5.1 Hz), 111.98 (t, J=238.4 Hz), 23.52; $^{19}$F NMR (376 MHz, CDCl$_3$) δ: −106.33−−117.12 (m). IR ν$_{max}$/cm$^1$ (film): 3107, 2997, 2220, 1576, 1423, 1394, 1355, 1268, 1242, 1105, 1038, 908, 860, 845, 785, 729, 705, 658. m/z HRMS (DART): [M+H]$^+$ calculated for C$_{11}$H$_{10}$F$_2$NS$^+$=226.0497, found 226.0518.

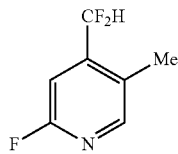

4-(difluoromethyl)-2-fluoro-5-methylpyridine (46). Prepared according to general procedure B using 2-fluoro-5-methylpyridine (52 μL, 0.5 mmol), (difluoromethyl)bis(4-methoxyphenyl)phosphane (163 mg, 0.55 mmol), Tf$_2$O (84 μL, 0.5 mmol), DBU (75 μL, 0.5 mmol), CH$_2$Cl$_2$ (5 mL), K$_2$CO$_3$ (69 mg, 0.5 mmol), THF (2.5 mL) and H$_2$O (2.5 mL) at rt for 2 hours. The crude material was purified by flash chromatography (silica gel: 80% CH$_2$Cl$_2$ in hexanes) to provide the title compound as a colorless oil (44 mg, 0.27 mmol, 27% iso. yield, 70% $^1$H NMR yield) Note that the product evaporates during solvent evaporation. $^1$H NMR (400 MHz, CDCl$_3$) δ: 8.09 (s, 1H), 7.05 (d, J=2.4 Hz, 1H), 6.69 (t, J=54.4 Hz, 1H), 2.36 (s, 3H); $^{13}$C NMR (100 MHz, CDCl$_3$) δ:162.69 (d, J=238.1 Hz), 149.46 (d, J=14.2 Hz), 145.18 (td, J=22.2, 7.2 Hz), 128.49 (q, J=4.6 Hz), 111.85 (td, J=240.9, 2.9 Hz), 106.06 (dt, J=40.1, 7.7 Hz), 14.85; $^{19}$F NMR (376 MHz, CDCl$_3$) δ: −70.09, −118.49 (d, J=54.4 Hz). IR ν$_{max}$/cm$^{-1}$ (film): 2973, 2360, 2342, 1612, 1582, 1490, 1456, 1387, 1348, 1269, 1156, 1049, 967, 881, 820, 735, 691. m/z HRMS (DART): [M+H]$^+$ calculated for C$_7$H$_7$F$_3$N$^+$=162.0525, found 162.0535.

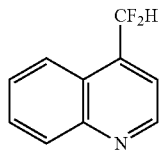 [SMILES: FC(F)c1ccnc2ccccc12]

4-(difluoromethyl)quinoline (47). Prepared according to general procedure A using quinoline (59.2 μL, 0.5 mmol), (difluoromethyl)bis(4-methoxyphenyl)phosphane (163 mg, 0.55 mmol), Tf$_2$O (84 L, 0.5 mmol), DBU (75 μL, 0.5 mmol), CH$_2$Cl$_2$ (5 mL), HCl (4 M in dioxane) (125 μL, 0.5 mmol), EtOH (4.5 mL) and H$_2$O (0.5 mL) at 40° C. for 24 hours. The crude material was purified by flash chromatography (silica gel: 5% EtOAc in CH$_2$Cl$_2$) to provide the title compound as colorless crystals (69 mg, 0.39 mmol, 77% yield). mp 53-55° C.; $^1$H NMR (400 MHz, CDCl$_3$) δ: 9.01 (d, J=4.3 Hz, 1H), 8.20 (d, J=8.5 Hz, 1H), 8.12-8.01 (m, 2H), 7.78 (ddd, J=8.4, 6.9, 1.4 Hz, 1H), 7.64 (ddd, J=8.4, 6.9, 1.4 Hz, 1H), 7.57 (d, J=4.3 Hz, 1H), 7.15 (t, J=54.5 Hz, 1H). $^{13}$C NMR (100 MHz, CDCl$_3$) δ:150.11, 148.75, 137.88 (t, J=21.8 Hz), 130.55, 130.03, 127.92, 124.25 (t, J=2.5 Hz), 123.40, 118.05 (t, J=7.7 Hz), 113.41 (t, J=240.4 Hz); $^{19}$F NMR (376 MHz, CDCl$_3$) δ: −115.10 (d, J=54.5 Hz). IR ν$_{max}$/cm$^1$ (film): 3059, 2983, 2923, 2851, 2360, 2342, 1602, 1515, 1501, 1466, 1407, 1359, 1310, 1245, 1171, 1147, 1115, 1074, 1031, 1022, 999, 986, 865, 851, 767, 816, 777, 752, 665, 625. m/z HRMS (DART): [M+H]$^+$ calculated for C$_{10}$H$_8$F$_2$N$^+$=180.0619, found 180.0632.

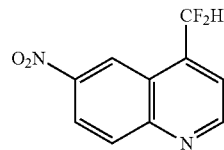 [SMILES: O=[N+]([O-])c1ccc2nccc(C(F)F)c2c1]

4-(difluoromethyl)-6-nitroquinoline (48). Prepare according to general procedure A using 6-nitroquinoline (87 mg, 0.5 mmol), (difluoromethyl)bis(4-methoxyphenyl)phosphane (163 mg, 0.55 mmol), Tf$_2$O (84 μL, 0.5 mmol), DBU (75 μL, 0.5 mmol), CH$_2$Cl$_2$ (5 mL), HCl (4 M in dioxane) (125 L, 0.5 mmol), EtOH (4.5 mL) and H$_2$O (0.5 mL) at 40° C. for 24 hours. The crude material was purified by flash chromatography (silica gel: 4% EtOAc in CH$_2$Cl$_2$) to provide the title compound as a white solid (61 mg, 0.27 mmol, 54% yield). mp 124-126° C.; $^1$H NMR (400 MHz, CDCl$_3$) δ: 9.20 (d, J=4.4 Hz, 1H), 9.05 (s, 1H), 8.55 (dd, J=9.2, 2.4 Hz, 1H), 8.35 (d, J=9.2 Hz, 1H), 7.74 (d, J=4.3 Hz, 1H), 7.20 (t, J=54.1 Hz, 1H); $^{13}$C NMR (100 MHz, CDCl$_3$) δ: 153.58, 150.63, 146.30, 139.97 (t, J=22.5 Hz), 132.49, 123.61, 123.21 (t, J=2.5 Hz), 120.71 (t, J=1.9 Hz), 120.06 (t, J=7.6 Hz), 112.95 (t, J=241.5 Hz); $^{19}$F NMR (376 MHz, CDCl$_3$) δ: −114.34 (d, J=54.1 Hz). IR ν$_{max}$/cm$^{-1}$ (film): 3118, 3084, 3059, 3027, 2923, 2840, 2359, 2342, 1620, 1609, 1574, 1421, 1392, 1344, 1300, 1264, 1235, 1221, 1145, 1120, 1100, 1046, 1009, 910, 894, 867, 805, 742, 736, 657. m/z HRMS (DART): [M+H]$^+$ calculated for C$_{10}$H$_7$F$_2$N$_2$O$_2$$^+$=225.047, found 225.0478.

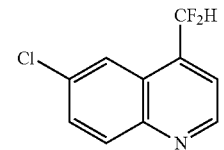 [SMILES: FC(F)c1ccnc2ccc(Cl)cc12]

6-chloro-4-(difluoromethyl)quinoline (49). Prepared according to general procedure A using 6-chloroquinoline (82 mg, 0.5 mmol), (difluoromethyl)bis(4-methoxyphenyl) phosphane (163 mg, 0.55 mmol), Tf$_2$O (84 μL, 0.5 mmol), DBU (75 μL, 0.5 mmol), CH$_2$Cl$_2$ (5 mL), HCl (4 M in dioxane) (125 μL, 0.5 mmol), EtOH (4.5 mL) and H$_2$O (0.5 mL) at 40° C. for 24 hours. The crude material was purified by flash chromatography (silica gel: 5% EtOAc in CH$_2$Cl$_2$) to provide the title compound as pale yellow crystals (75 mg, 0.35 mmol, 70% yield). mp 65-66° C.; $^1$H NMR (400 MHz, CDCl$_3$) δ: 8.99 (d, J=4.3 Hz, 1H), 8.12 (d, J=9.0 Hz, 1H), 8.06 (d, J=1.7 Hz, 1H), 7.72 (dd, J=9.0, 2.2 Hz, 1H), 7.58 (d, J=4.3 Hz, 1H), 7.07 (t, J=54.4 Hz, 1H); $^{13}$C NMR (100 MHz, CDCl$_3$) δ: 150.27, 147.17, 137.20 (t, J=22.1 Hz), 134.09, 132.09, 131.11, 124.81 (t, J=2.8 Hz), 122.66, 119.00 (t, J=7.7 Hz), 113.25 (t, J=240.8 Hz); $^{19}$F NMR (376 MHz, CDCl$_3$) δ: −114.91 (d, J=54.3 Hz). IR ν$_{max}$/cm$^{-1}$ (film): 2925, 2360, 2342, 1602, 1498, 1453, 1386, 1346, 1301, 1240, 1119, 1068, 1036, 851, 790. m/z HRMS (DART): [M+H]+ calculated for $C_{10}H_7ClF_2N^+$=214.023, found 214.0233.

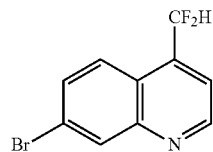 [SMILES: FC(F)c1ccnc2cc(Br)ccc12]

7-bromo-4-(difluoromethyl)quinoline (51). Prepared according to general procedure A using 8-bromoquinoline (104 mg, 0.5 mmol), (difluoromethyl)bis(4-methoxyphenyl) phosphane (163 mg, 0.55 mmol), Tf$_2$O (84 µL, 0.5 mmol), DBU (75 µL, 0.5 mmol), CH$_2$Cl$_2$ (5 mL), HCl (4 M in dioxane) (125 µL, 0.5 mmol), EtOH (4.5 mL) and H$_2$O (0.5 mL) at 40° C. for 24 hours. The crude material was purified by flash chromatography (silica gel: 3% EtOAc in CH$_2$Cl$_2$) to provide the title compound as colorless crystals (104 mg, 0.40 mmol, 81% yield). mp 77-79° C.; $^1$H NMR (400 MHz, CDCl$_3$) δ: 8.99 (d, J=4.3 Hz, 1H), 8.36 (d, J=2.0 Hz, 1H), 7.94 (dt, J=9.0, 1.3 Hz, 1H), 7.72 (dd, J=9.0, 2.0 Hz, 1H), 7.57 (d, J=4.3 Hz, 1H), 7.09 (t, J=54.4 Hz, 1H); $^{13}$C NMR (100 MHz, CDCl$_3$) δ: 151.13, 149.39, 138.11 (t, J=22.0 Hz), 132.83, 131.44, 124.88, 124.33, 122.84 (t, J=2.9 Hz), 118.46 (t, J=7.7 Hz), 113.29 (t, J=240.9 Hz); $^{19}$F NMR (376 MHz, CDCl$_3$) δ: −114.66 (d, J=54.4 Hz). IR ν$_{max}$/cm$^{-1}$ (film): 3068, 3040, 2975, 2923, 2852, 2360, 2333, 1600, 1494, 1442, 1362, 1305, 1238, 1166, 1120, 1080, 1066, 1041, 1001, 899, 858, 821, 778, 769, 672. m/z HRMS (DART): [M+H]+ calculated for $C_{10}H_7BrF_2N^+$=257.9724, found 257.9745.

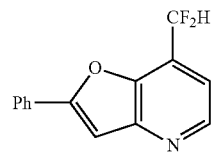 [SMILES: FC(F)c1ccnc2cc(-c3ccccc3)oc12]

7-(difluoromethyl)-2-phenylfuro[3,2-b]pyridine (52). Prepared according to general procedure A using 2-phenyl-furo[3,2-b]pyridine (195 mg, 1.0 mmol), (difluoromethyl) bis(4-methoxyphenyl)phosphane (326 mg, 1.1 mmol), Tf$_2$O (168 µL, 1.0 mmol), DBU (150 µL, 1.0 mmol), CH$_2$Cl$_2$ (10 mL), HCl (4 M in dioxane) (250 µL, 1.0 mmol), EtOH (9 mL) and H$_2$O (1.0 mL) at 40° C. for 24 hours. The crude material was purified by flash chromatography (silica gel: 5% EtOAc in CH$_2$Cl$_2$) to provide the title compound as a pale yellow solid (46 mg, 0.19 mmol, 19% yield). mp 93-94° C.; $^1$H NMR (400 MHz, CDCl$_3$) δ: 8.64 (d, J=4.4 Hz, 1H), 7.96-7.85 (m, 2H), 7.56-7.39 (m, 3H), 7.35 (d, J=4.9 Hz, 1H), 7.27 (s, 1H), 7.15 (t, J=54.7 Hz, 1H); $^{13}$C NMR (100 MHz, CDCl$_3$) δ: 160.92, 150.48, 146.60, 144.71-143.57 (m), 130.21, 129.21, 129.15, 125.66, 124.47 (t, J=24.9 Hz), 115.32-114.04 (m), 110.90 (t, J=240.0 Hz), 102.49; $^{19}$F NMR (376 MHz, CDCl$_3$) δ: −116.04 (d, J=54.7 Hz). IR ν$_{max}$/cm$^{-1}$ (film): 3117, 3068, 3037, 2979, 2924, 2853, 2360, 2341, 1577, 1494, 1448, 1398, 1375, 1362, 1282, 1267, 1257, 1215, 1114, 1080, 1034, 1015, 992, 917, 840, 800, 771, 756, 698, 686, 659. m/z HRMS (DART): [M+H]+ calculated for $C_{14}H_{10}F_2NO^+$=246.0725, found 246.0748.

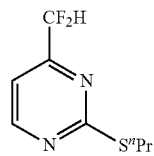

4-(difluoromethyl)-2-(propylthio)pyrimidine (53). Prepared according to general procedure A using 2-(propylthio) pyrimidine (77 mg, 0.5 mmol), (difluoromethyl)bis(4-methoxyphenyl)phosphane (163 mg, 0.55 mmol), Tf$_2$O (84 µL, 0.5 mmol), DBU (75 µL, 0.5 mmol), CH$_2$Cl$_2$ (5 mL), HCl (4 M in dioxane) (125 µL, 0.5 mmol), EtOH (4.5 mL) and H$_2$O (0.5 mL) at 40° C. for 24 hours. The crude material was purified by flash chromatography (silica gel: 10% EtOAc in hexanes) to provide the title compound as a colorless oil (32 mg, 0.16 mmol, 32% yield). $^1$H NMR (400 MHz, CDCl$_3$) δ: 8.67 (d, J=5.0 Hz, 1H), 7.22 (d, J=5.0 Hz, 1H), 6.44 (t, J=54.8 Hz, 1H), 3.23-3.05 (m, 2H), 1.77 (h, J=7.3 Hz, 2H), 1.05 (t, J=7.4 Hz, 3H). $^{13}$C NMR (100 MHz, CDCl$_3$) δ: 173.68, 160.52 (t, J=26.9 Hz), 159.00, 112.59 (t, J=242.3 Hz) 111.64 (t, J=2.9 Hz), 33.09, 22.55, 13.58; $^{19}$F NMR (376 MHz, CDCl$_3$) δ: −119.57 (d, J=54.8 Hz). IR ν$_{max}$/cm$^{-1}$ (film): 2966, 2933, 2874, 2360, 2342, 1560, 1458, 1436, 1363, 1325, 1262, 1202, 1182, 1110, 1052, 835, 751, 735. m/z HRMS (DART): [M+H]+ calculated for $C_8H_{11}F_2N_2S^+$=205.0606, found 205.0624.

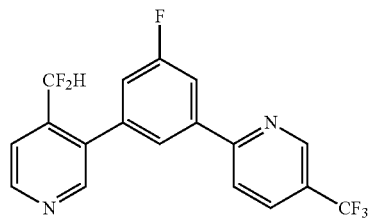 [SMILES: Fc1cc(-c2ccc(C(F)(F)F)cn2)cc(-c2cnccc2C(F)F)c1]

2-(3-(4-(difluoromethyl)pyridin-3-yl)-5-fluorophenyl)-5-(trifluoromethyl)pyridine (61). Prepared according to general procedure A using 2-(3-fluoro-5-(pyridin-3-yl)phenyl)-5-(trifluoromethyl)pyridine (80 mg, 0.25 mmol), (difluoromethyl)bis(4-methoxyphenyl)phosphane (82 mg, 0.275 mmol), Tf$_2$O (42 L, 0.25 mmol), DBU (37 µL, 0.25 mmol), CH$_2$Cl$_2$ (2.5 mL), HCl (4 M in dioxane) (63 µL, 0.25 mmol), EtOH (2.25 mL) and H$_2$O (0.25 mL) at 40° C. for 23 hours. The crude material was purified by flash chromatography (silica gel: 20% EtOAc in toluene) to provide the title compound as a white solid (57 mg, 0.155 mmol, 62% yield). m.p. 120-123° C.; $^1$H NMR (400 MHz, CDCl$_3$) δ: 9.02-8.92 (m, 1H), 8.83 (d, J=5.1 Hz, 1H), 8.72 (s, 1H), 8.04 (dd, J=8.4, 2.3 Hz, 1H), 7.94-7.83 (m, 3H), 7.69 (d, J=5.1 Hz, 1H), 7.22 (dt, J=8.5, 2.0 Hz, 1H), 6.58 (t, J=54.2 Hz, 1H); $^{13}$C NMR (101 MHz, CDCl$_3$) δ: 164.53, 162.05, 159.25-157.72 (m), 151.00, 150.37, 147.02 (d, J=4.0 Hz), 140.89 (d, J=8.1 Hz), 139.35 (t, J=23.1 Hz), 137.73 (d, J=8.1 Hz), 134.67-134.33 (m), 126.05 (q, J=33.2 Hz), 124.98, 124.29, 120.28, 119.53 (t, J=5.3 Hz), 118.20 (d, J=22.6 Hz), 114.77 (d, J=23.0 Hz), 111.65 (t, J=239.0 Hz); $^{19}$F NMR (377 MHz, CDCl$_3$) δ: −62.38, −110.80 (t, J=9.1 Hz), −111.59 (d, J=54.1 Hz). IR max/cm$^{-1}$ (film): 3080, 3036, 2923, 1600, 1571, 1492, 1432, 1046, 1329, 1237, 1164, 1177, 1138, 1076, 1020, 920, 886, 842, 771, 697, 670, 553, 532. m/z HRMS (DART): [M+H]+ calculated for $C_{18}H_{11}F_6N_2$=369.0821, found 369.0846.

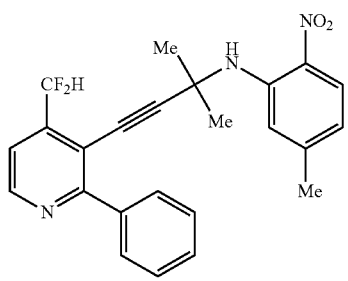 [SMILES: Cc1ccc([N+](=O)[O-])c(NC(C)(C)C#Cc2c(C(F)F)ccnc2-c2ccccc2)c1]

N-(4-(4-(difluoromethyl)-2-phenylpyridin-3-yl)-2-methylbut-3-yn-2-yl)-5-methyl-2-nitroaniline (62). Prepared according to general procedure A using 5-methyl-N-(2-methyl-4-(2-phenylpyridin-3-yl)but-3-yn-2-yl)-2-nitroaniline (70 mg, 0.25 mmol), (difluoromethyl)bis(4-methoxyphenyl)phosphane (82 mg, 0.275 mmol), Tf$_2$O (42 μL, 0.25 mmol), DBU (37 μL, 0.25 mmol), CH$_2$Cl$_2$ (2.5 mL), HCl (4 M in dioxane) (125 μL, 0.5 mmol), EtOH (2.25 mL) and H$_2$O (0.25 mL) at 40° C. for 48 hours. The crude material was purified by flash chromatography (silica gel: 5% EtOAc in hexanes) to provide the title compound as a yellow oil (64 mg, 0.152 mmol, 61% yield). $^1$H NMR (400 MHz, CDCl$_3$) δ: 8.75 (d, J=5.0 Hz, 1H), 8.31 (s, 1H), 8.07 (d, J=8.7 Hz, 1H), 7.83 (dd, J=7.6, 2.0 Hz, 2H), 7.50 (d, J=4.9 Hz, 1H), 7.43-7.31 (m, 3H), 7.08 (d, J=1.6 Hz, 1H), 6.91 (t, J=54.8 Hz, 1H), 6.49 (dd, J=8.7, 1.7 Hz, 1H), 2.19 (s, 3H), 1.73 (s, 6H); $^{13}$C NMR (101 MHz, CDCl$_3$) δ: 161.31, 149.15, 147.37, 144.16 (t, J=22.9 Hz), 143.34, 138.57, 131.18, 129.47, 129.34, 127.04, 118.01, 117.33 (t, J=5.4 Hz), 115.71, 115.19 (d, J=5.8 Hz), 112.20 (t, J=240.0 Hz), 103.06, 48.35, 29.99, 22.14; $^{19}$F NMR (376 MHz, CDCl$_3$) δ: −116.97 (d, J=54.8 Hz). IR ν$_{max}$/cm$^{-1}$ (film): 3352, 2983, 2932, 2360, 2342, 1617, 1578, 1491, 1405, 1335, 1237, 1187, 1128, 1073, 1048, 908, 843, 751, 732, 697. m/z HRMS (DART): [M+H]$^+$ calculated for C$_{24}$H$_{22}$F$_2$N$_3$O$_2$$^+$=422.1675, found 422.1682.

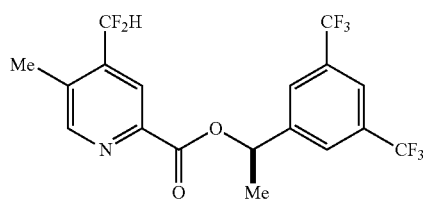 [SMILES: Cc1cnc(C(=O)O[C@H](C)c2cc(C(F)(F)F)cc(C(F)(F)F)c2)cc1C(F)F]

(R)-1-(3,5-bis(trifluoromethyl)phenyl)ethyl 4-(difluoromethyl)-5-methylpicolinate (64). Prepared according to general procedure A using (R)-1-(3,5-bis(trifluoromethyl)phenyl) ethyl 5-methylpicolinate (94 mg, 0.25 mmol), (difluoromethyl)bis(4-methoxyphenyl)phosphane (82 mg, 0.275 mmol), Tf$_2$O (42 L, 0.25 mmol), DBU (37 μL, 0.25 mmol), CH$_2$Cl$_2$ (2.5 mL), HCl (4 M in dioxane) (63 μL, 0.25 mmol), EtOH (2.25 mL) and H$_2$O (0.25 mL) at 60° C. for 48 hours. The crude material was purified by flash chromatography (silica gel: 1% EtOAc in CH$_2$Cl$_2$) to provide the title compound as a colorless oil (57 mg, 0.133 mmol, 53% yield). $^1$H NMR (400 MHz, CDCl$_3$) δ: 8.68 (t, J=0.9 Hz, 1H), 8.20 (s, 1H), 7.92 (d, J=1.7 Hz, 2H), 7.82 (t, J=1.7 Hz, 1H), 6.76 (t, J=54.4 Hz, 1H), 6.27 (q, J=6.7 Hz, 1H), 2.49 (d, J=1.6 Hz, 3H), 1.78 (d, J=6.7 Hz, 3H); $^{13}$C NMR (101 MHz, CDCl$_3$) δ:163.78, 152.49, 146.39, 143.75, 140.99 (t, J=22.4 Hz), 135.33 (t, J=4.3 Hz), 132.05 (q, J=33.4 Hz), 126.58 (q, J=3.6 Hz), 123.15 (q, J=272.8 Hz), 122.38-122.00 (m), 121.30 (t, J=7.1 Hz), 112.20 (t, J=240.9 Hz), 72.59, 21.97, 15.81; $^{19}$F NMR (377 MHz, CDCl$_3$) δ: −62.90, −117.64 (d, J=54.7 Hz). IR ν$_{max}$/cm$^{-1}$ (film): 2989, 2360, 2342, 1726, 1456, 1384, 1278, 1247, 1222, 1174, 1134, 1054, 907, 845, 755, 730, 705, 682, 669. m/z HRMS (DART): [M+H]$^+$ calculated for C$_{18}$H$_{14}$F$_8$NO$_2$$^+$=428.0891, found 428.0907.

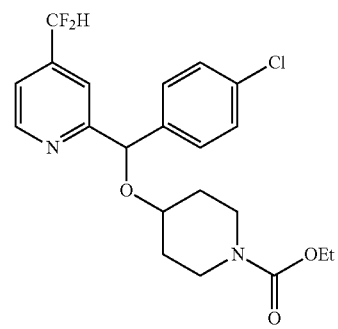 [SMILES: CCOC(=O)N1CCC(OC(c2ccc(Cl)cc2)c2cc(C(F)F)ccn2)CC1]

ethyl 4-((4-chlorophenyl)(4-(difluoromethyl)pyridin-2-yl)methoxy)piperidine-1-carboxylate (66). Prepared according to general procedure A using ethyl 4-((4-chlorophenyl)(pyridin-2-yl)methoxy)piperidine-1-carboxylate (94 mg, 0.25 mmol), (difluoromethyl)bis(4-methoxyphenyl)phosphane (82 mg, 0.275 mmol), Tf$_2$O (42 μL, 0.25 mmol), DBU (37 μL, 0.25 mmol), CH$_2$Cl$_2$ (2.5 mL), HCl (4 M in dioxane) (63 μL, 0.25 mmol), EtOH (2.25 mL) and H$_2$O (0.25 mL) at 40° C. for 45 hours. The crude material was purified by flash chromatography (silica gel: 30% EtOAc in toluene) to provide the title compound as a colorless oil (69 mg, 0.162 mmol, 65% yield). $^1$H NMR (400 MHz, CDCl$_3$) δ: 8.58 (d, J=5.1 Hz, 1H), 7.62 (s, 1H), 7.33 (d, J=8.5 Hz, 2H), 7.28-7.21 (m, 3H), 6.58 (t, J=55.7 Hz, 1H), 5.62 (s, 1H), 4.07 (q, J=7.1 Hz, 2H), 3.82-3.66 (m, 2H), 3.59 (tt, J=7.7, 3.7 Hz, 1H), 3.21-3.08 (m, 2H), 1.89-1.72 (m, 2H), 1.61 (td, J=8.4, 4.1 Hz, 2H), 1.20 (t, J=7.1 Hz, 3H); $^{13}$C NMR (101 MHz, CDCl$_3$) δ: 163.25, 155.60, 149.79, 143.28 (t, J=23.4 Hz), 139.63, 133.79, 128.83, 128.28, 118.80 (t, J=5.7 Hz), 116.77 (t, J=6.1 Hz), 113.05 (t, J=241.1 Hz), 80.75, 72.96, 61.40, 41.15 (d, J=7.4 Hz), 31.16 (d, J=34.4 Hz), 14.79; $^{19}$F NMR (377 MHz, CDCl$_3$) δ: −115.57 (dd, J=55.8, 10.1 Hz). IR ν$_{max}$/cm$^{-1}$ (film): 2982, 2931, 2870, 1687, 1609, 1571, 1489, 1474, 1433, 1383, 1274, 1229, 1164, 1113, 1077, 1032, 1015, 828, 751, 666, 548, 531. m/z HRMS (DART): [M+H]$^+$ calculated for C$_{21}$H$_{24}$ClF$_2$N$_2$O$_3$$^+$=425.1438, found 425.1463.

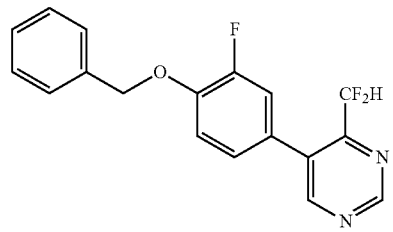 [SMILES: Fc1cc(-c2cncnc2C(F)F)ccc1OCc1ccccc1]

5-(4-(benzyloxy)-3-fluorophenyl)-4-(difluoromethyl)pyrimidine (67). Prepared according to general procedure A using 5-(4-(benzyloxy)-3-fluorophenyl) pyrimidine (70 mg, 0.25 mmol), (difluoromethyl)bis(4-methoxyphenyl)phosphane (82 mg, 0.275 mmol), Tf$_2$O (42 µL, 0.25 mmol), DBU (37 µL, 0.25 mmol), CH$_2$Cl$_2$ (2.5 mL), HCl (4 M in dioxane) (63 µL, 0.25 mmol), EtOH (2.25 mL) and H$_2$O (0.25 mL) at 40° C. for 17 hours. The crude material was purified by flash chromatography (silica gel: 30% EtOAc in hexanes) to provide the title compound as a white solid (32 mg, 0.096 mmol, 39% yield). m.p. 73-75° C.; $^1$H NMR (400 MHz, CDCl$_3$) δ 9.33 (s, 1H), 8.81 (s, 1H), 7.51-7.33 (m, 5H), 7.22-7.04 (m, 3H), 6.58 (t, J=53.6 Hz, 1H), 5.22 (s, 2H); $^{13}$C NMR (101 MHz, CDCl$_3$) δ:159.46, 157.84, 155.64 (t, J=23.5 Hz), 153.97, 151.50, 147.90 (d, J=10.5 Hz), 136.08, 132.83 (d, J=2.2 Hz), 128.90, 128.52, 127.57, 125.96-125.44 (m), 117.53 (dt, J=19.7, 1.8 Hz), 115.78 (d, J=2.5 Hz), 111.90 (t, J=242.5 Hz), 71.48; $^{19}$F NMR (376 MHz, CDCl$_3$) δ: −114.77 (d, J=53.8 Hz), −131.97 (dd, J=11.4, 8.1 Hz). IR $v_{max}$/cm$^{-1}$ (film): 3038, 2923, 2851, 1618, 1573, 1555, 1520, 1511, 1455, 1435, 1384, 1371, 1348, 1300, 1272, 1211, 1134, 1093, 1059, 1009, 993, 926, 906, 883, 817, 756, 746, 698, 668, 637, 630, 558. m/z HRMS (DART): [M+H]$^+$ calculated for C$_{18}$H$_{14}$F$_3$N$_2$O$^+$=331.1053, found 331.1058.

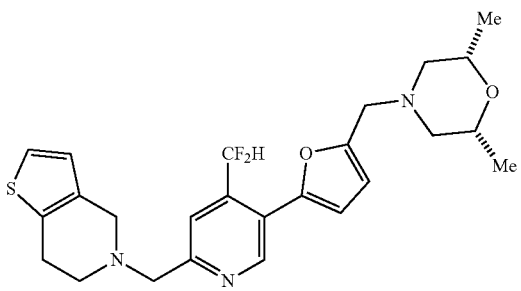 [SMILES: C[C@@H]1CN(Cc2ccc(-c3cnc(CN4CCc5sccc5C4)cc3C(F)F)o2)C[C@H](C)O1]

(2R,6S)-4-((5-(4-(difluoromethyl)-6-((6,7-dihydrothieno[3,2-c]pyridin-5(4H)-yl)methyl)pyridin-3-yl)furan-2-yl)methyl)-2,6-dimethylmorpholine (68). Prepared according to general procedure A except the reaction was allowed to warm to −50° C. after DBU addition and stirred for 5 minutes, then HCl was added and the reaction heated to 60° C. using (2R,6S)-4-((5-(6-((6,7-dihydrothieno[3,2-c]pyridin-5(4H)-yl)methyl)pyridin-3-yl)furan-2-yl)methyl)-2,6-dimethylmorpholine (106 mg, 0.25 mmol), (difluoromethyl)bis(4-methoxyphenyl)phosphane (81.5 mg, 0.28 mmol), Tf$_2$O (42 µL, 0.25 mmol), DBU (38 µL, 0.25 mmol), CH$_2$Cl$_2$ (2.5 mL), HCl (4 M in dioxane) (190 µL, 0.75 mmol), EtOH (2.25 mL) and H$_2$O (0.25 mL) at 60° C. for 72 hours. The crude material was purified by flash chromatography (silica gel: 1% MeOH in CH$_2$Cl$_2$) to provide the title compound as a pale yellow oil (60 mg, 0.13 mmol, 52% yield). $^1$H NMR (400 MHz, CDCl$_3$) δ: 8.91 (s, 1H), 7.82 (s, 1H), 7.08 (d, J=5.1 Hz, 1H), 7.02 (t, J=54.6 Hz, 1H), 6.70 (dd, J=11.2, 4.2 Hz, 2H), 6.38 (d, J=3.3 Hz, 1H), 3.94 (s, 2H), 3.77-3.66 (m, 4H), 3.62 (s, 2H), 2.99-2.85 (m, 4H), 2.77 (d, J=10.5 Hz, 2H), 1.86 (t, J=10.7 Hz, 2H), 1.16 (d, J=6.3 Hz, 6H); $^{13}$C NMR (100 MHz, CDCl$_3$) δ: 158.92, 153.65, 148.50, 148.20, 137.64 (t, J=22.8 Hz), 133.74, 133.48, 125.36, 123.32 (t, J=5.8 Hz), 122.85, 118.84 (t, J=6.8 Hz), 111.82 (t, J=239.0 Hz), 111.53, 111.45-111.16 (m), 71.80, 63.44, 59.06, 54.84, 53.38, 50.98, 25.54, 19.27; $^{19}$F NMR (376 MHz, CDCl$_3$) δ: −115.13 (d, J=54.6 Hz). IR $v_{max}$/cm$^{-1}$ (film): 2971, 2931, 2871, 2813, 2360, 2342, 1474, 1454, 1376, 1355, 1321, 1162, 1142, 1080, 1044, 1023, 906, 837, 795, 730, 702. m/z HRMS (DART): [M+H]$^+$ calculated for C$_{25}$H$_{30}$F$_2$N$_3$O$_2$S$^+$=474.2021, found 474.2025.

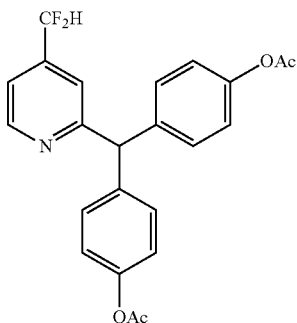 [SMILES: CC(=O)Oc1ccc(C(c2ccc(OC(C)=O)cc2)c2cc(C(F)F)ccn2)cc1]

((4-(difluoromethyl)pyridin-2-yl)methylene)bis(4,1-phenylene) diacetate (71). Prepared according to general procedure C using (pyridin-2-ylmethylene)bis(4,1-phenylene) diacetate (90 mg, 0.25 mmol), (difluoromethyl)bis(4-methoxyphenyl)phosphane (82 mg, 0.275 mmol), Tf$_2$O (42 µL, 0.25 mmol), DBU (37 µL, 0.25 mmol), CH$_2$Cl$_2$ (2.5 mL), HCl (4 M in dioxane) (63 µL, 0.25 mmol), and TBAF (1 M in THF, 250 µL, 0.25 mmol) at 40° C. for 24 hours. The crude material was purified by flash chromatography (silica gel: 20% EtOAc in toluene) to provide the title compound as a yellow oil (86 mg, 0.208 mmol, 83% yield). $^1$H NMR (400 MHz, CDCl$_3$) δ: 8.72 (d, J=5.0 Hz, 1H), 7.29 (dd, J=4.9, 1.4 Hz, 1H), 7.23 (s, 1H), 7.21-7.15 (m, 4H), 7.08-7.00 (m, 4H), 6.58 (t, J=55.7 Hz, 1H), 5.70 (s, 1H), 2.28 (s, 6H); $^{13}$C NMR (101 MHz, CDCl$_3$) δ 169.52, 163.85, 150.53, 149.60, 142.97 (t, J=23.3 Hz), 139.53, 130.36, 121.74, 120.04 (t, J=6.1 Hz), 117.99 (t, J=5.7 Hz), 113.04 (t, J=241.0 Hz), 58.20, 21.26; $^{19}$F NMR (376 MHz, CDCl$_3$) δ: −115.50 (d, J=55.9 Hz). IR $v_{max}$/cm$^{-1}$ (film): 3023, 1754, 1608, 1571, 1504, 1412, 1369, 1165, 1044, 1018, 909, 847, 751, 730, 665, 650, 549, 531. m/z HRMS (DART): [M+H]$^+$ calculated for C$_{23}$H$_{20}$F$_2$NO$_4^+$=412.1355, found 412.1367.

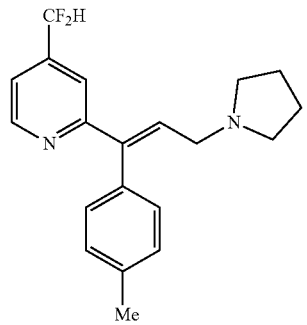 [SMILES: Cc1ccc(/C(=C\CN2CCCC2)c2cc(C(F)F)ccn2)cc1]

(E)-4-(difluoromethyl)-2-(3-(pyrrolidin-1-yl)-1-(p-tolyl)prop-1-en-1-yl)pyridine (73). Prepared according to general procedure A (except (E)-2-(3-(pyrrolidin-1-yl)-1-(p-tolyl)prop-1-en-1-yl)pyridine was protonated using TfOH (22 µL, 0.25 mmol) before the salt reaction) using (E)-2-(3-(pyrrolidin-1-yl)-1-(p-tolyl)prop-1-en-1-yl)pyridine (70 mg, 0.25 mmol), (difluoromethyl)bis(4-methoxyphenyl)phosphane (82 mg, 0.275 mmol), Tf$_2$O (42 µL, 0.25 mmol), DBU (75 µL, 0.5 mmol), CH$_2$Cl$_2$ (2.5 mL), HCl (4 M in dioxane) (63 µL, 0.25 mmol), EtOH (2.25 mL) and H$_2$O (0.25 mL) at 40° C. for 25 hours. The crude material was purified by flash chromatography (silica gel: 5% MeOH in CH$_2$Cl$_2$) to provide the title compound as a brown oil (66 mg, 0.200 mmol, 80% yield). $^1$H NMR (400 MHz, CDCl$_3$) δ: 8.73 (d, J=4.9 Hz, 1H), 7.33 (dd, J=4.9, 1.4 Hz, 1H), 7.28 (d, J=7.8 Hz, 2H), 7.11-7.00 (m, 4H), 6.52 (t, J=55.6 Hz, 1H), 3.79 (d, J=7.3 Hz, 2H), 3.25 (s, 4H), 2.43 (s, 3H), 2.15-2.01 (m, 4H); $^{13}$C NMR (101 MHz, CDCl$_3$) δ: 159.67, 150.02, 142.50 (t, J=23.2 Hz), 141.90, 137.50, 134.80, 131.15, 129.76, 129.46, 118.33 (t, J=6.2 Hz), 117.93 (t, J=5.6 Hz), 113.23 (t, J=240.7 Hz), 54.63, 54.11, 23.63, 21.43; $^{19}$F NMR (377 MHz, CDCl$_3$) δ: −115.28 (d, J=55.9 Hz). IR $v_{max}$/cm$^{-1}$ (film): 2966, 2927, 2878, 2796, 1605, 1568, 1513, 1462, 1413, 1379, 1216, 1157, 1110, 1046, 908, 823, 731, 666, 549, 531. m/z HRMS (DART): [M+H]$^+$ calculated for $C_{20}H_{23}F_2N_2{}^+$=329.1824, found 329.1832.

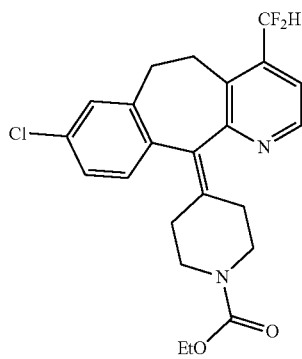 [SMILES: CCOC(=O)N1CCC(=C2c3ccc(Cl)cc3CCc3c(C(F)F)ccnc32)CC1]

ethyl 4-(8-chloro-4-(difluoromethyl)-5,6-dihydro-11H-benzo[5,6]cyclohepta[1,2-b]pyridin-11-ylidene)piperidine-1-carboxylate (75). Prepared according to general procedure A using ethyl 4-(8-chloro-5,6-dihydro-11H-benzo[5,6]cyclohepta[1,2-b]pyridin-11-ylidene)piperidine-1-carboxylate (96 mg, 0.25 mmol), (difluoromethyl)bis(4-methoxyphenyl)phosphane (82 mg, 0.275 mmol), Tf$_2$O (42 μL, 0.25 mmol), DBU (37 μL, 0.25 mmol), CH$_2$Cl$_2$ (2.5 mL), HCl (4 M in dioxane) (63 μL, 0.25 mmol), EtOH (2.25 mL) and H$_2$O (0.25 mL) at 40° C. for 20 hours. The crude material was purified by flash chromatography (silica gel: 50% EtOAc in toluene) to provide the title compound as a yellow oil (93 mg, 0.216 mmol, 86% yield). $^1$H NMR (400 MHz, CDCl$_3$) δ: 8.53 (d, J=5.0 Hz, 1H), 7.32 (d, J=5.1 Hz, 1H), 7.12 (d, J=2.5 Hz, 3H), 6.76 (t, J=54.7 Hz, 1H), 4.14 (q, J=7.1 Hz, 2H), 3.80 (d, J=12.5 Hz, 2H), 3.49-3.30 (m, 2H), 3.26-3.11 (m, 2H), 3.10-2.99 (m, 1H), 2.94-2.83 (m, 1H), 2.53-2.32 (m, 3H), 2.27-2.10 (m, 1H), 1.25 (t, J=7.1 Hz, 3H); $^{13}$C NMR (101 MHz, CDCl$_3$) δ 160.34, 155.48, 147.54, 139.97 (t, J=21.8 Hz), 138.65, 137.80, 135.81, 133.75, 133.25, 131.24, 131.11 (t, J=4.0 Hz), 129.69, 126.24, 118.79 (t, J=7.2 Hz), 112.71 (t, J=240.4 Hz), 61.40, 44.71 (d, J=15.6 Hz), 31.59, 30.66 (d, J=7.2 Hz), 26.31, 14.69; $^{19}$F NMR (377 MHz, CDCl$_3$) δ: −112.76−−118.16 (m). IR $v_{max}$/cm$^{-1}$ (film): 2981, 2911, 2870, 1734, 1591, 1478, 1434, 1386, 1374, 1227, 1119, 1043, 909, 757, 733, 561. m/z HRMS (DART): [M+H]$^+$ calculated for $C_{23}H_{24}ClF_2N_2O_2{}^+$=433.1489, found 433.1515.

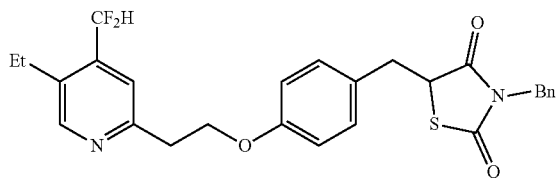 [SMILES: CCc1cnc(CCOc2ccc(CC3SC(=O)N(Cc4ccccc4)C3=O)cc2)cc1C(F)F]

3-benzyl-5-(4-(2-(4-difluoromethyl)-5-ethylpyridin-2-yl)ethoxy)benzyl)thiazolidine-2,4-dione (78). Prepared according to general procedure A using 3-benzyl-5-(4-(2-(5-ethylpyridin-2-yl)ethoxy)benzyl)thiazolidine-2,4-dione (112 mg, 0.25 mmol), (difluoromethyl)bis(4-methoxyphenyl)phosphane (82 mg, 0.275 mmol), Tf$_2$O (42 μL, 0.25 mmol), DBU (37 μL, 0.25 mmol), CH$_2$Cl$_2$ (2.5 mL), HCl (4 M in dioxane) (63 μL, 0.25 mmol), EtOH (2.25 mL) and H$_2$O (0.25 mL) at 40° C. for 48 hours. The crude material was purified by flash chromatography (silica gel: 15% EtOAc in toluene) to provide the title compound as a colorless oil (31 mg, 0.061 mmol, 25% yield). $^1$H NMR (400 MHz, CDCl$_3$) δ: 8.50 (s, 1H), 7.40 (s, 1H), 7.26 (d, J=1.2 Hz, 6H), 7.05 (d, J=8.6 Hz, 2H), 6.91-6.61 (m, 3H), 4.78-4.60 (m, 2H), 4.42 (dd, J=8.8, 3.9 Hz, 1H), 4.32 (t, J=6.5 Hz, 2H), 3.38 (dd, J=14.2, 3.9 Hz, 1H), 3.27 (t, J=6.5 Hz, 2H), 3.08 (dd, J=14.2, 8.7 Hz, 1H), 2.75 (q, J=7.6 Hz, 2H), 1.27 (t, J=7.6 Hz, 4H); $^{13}$C NMR (101 MHz, CDCl$_3$) δ: 173.82, 171.05, 158.26, 157.12, 150.97, 139.71 (t, J=21.8 Hz), 135.12, 134.58, 130.53, 128.76, 128.20, 127.63, 119.55 (t, J=6.8 Hz), 114.87, 112.58 (d, J=238.9 Hz), 67.01, 51.75, 45.27, 37.81, 37.68, 22.65, 15.74; $^{19}$F NMR (377 MHz, CDCl$_3$) δ: −115.09 (d, J=54.8 Hz). IR $v_{max}$/cm$^{-1}$ (film): 3017, 2971, 2935, 2878, 1749, 1679, 1610, 1512, 1382, 1330, 1302, 1244, 1216, 1179, 1147, 1036, 908, 699, 667, 561, 530. m/z HRMS (DART): [M+H]$^+$ calculated for $C_{27}H_{27}F_2N_2O_3S^+$=497.1705, found 497.1720.

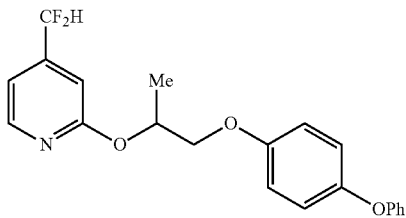 [SMILES: CC(COc1ccc(Oc2ccccc2)cc1)Oc1cc(C(F)F)ccn1]

4-(difluoromethyl)-2-((1-(4-phenoxyphenoxy)propan-2-yl)oxy)pyridine (82). Prepared according to general procedure B using 2-((1-(4-phenoxyphenoxy)propan-2-yl)oxy)pyridine (80 mg, 0.25 mmol), (difluoromethyl)bis(4-methoxyphenyl)phosphane (82 mg, 0.275 mmol), Tf$_2$O (42 μL, 0.25 mmol), DBU (75 μL, 0.5 mmol), CH$_2$Cl$_2$ (2.5 mL), K$_2$CO$_3$ (35 mg, 0.25 mmol), THF (0.625 mL) and H$_2$O (0.625 mL) at rt for 30 minutes. The crude material was purified by flash chromatography (silica gel: 100% toluene) to provide the title compound as a colorless oil (18 mg, 0.048 mmol, 19% yield). $^1$H NMR (400 MHz, CDCl$_3$) δ: 8.25 (d, J=5.2 Hz, 1H), 7.29 (dd, J=8.6, 7.3 Hz, 2H), 7.08-7.01 (m, 1H), 7.01-6.88 (m, 7H), 6.87 (s, 1H), 6.56 (t, J=55.8 Hz, 1H), 5.67-5.56 (m, 1H), 4.13 (ddd, J=42.4, 9.9, 5.1 Hz, 2H), 1.48 (d, J=6.4 Hz, 3H); $^{13}$C NMR (101 MHz, CDCl$_3$) δ:163.74, 158.59, 155.25, 150.54, 147.97, 145.21, 129.76, 122.62, 120.91, 117.79, 115.92, 115.54-110.51 (m), 108.68, 71.09, 70.20, 17.01; $^{19}$F NMR (377 MHz, CDCl$_3$) δ: −115.62 (d, J=55.8 Hz). IR $v_{max}$/cm$^{-1}$ (film): 2985, 1617, 1590, 1569, 1504, 1489, 1422, 1380, 1317, 1221, 1078, 1047, 909, 759, 734, 582, 560. m/z HRMS (DART): [M+H]$^+$ calculated for $C_{21}H_{20}F_2NO_3{}^+$=372.1406, found 372.1420.

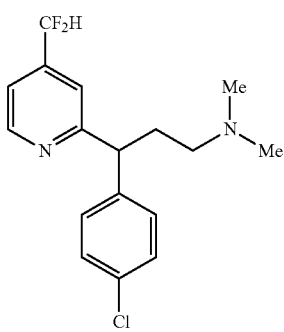 [SMILES: CN(C)CCC(c1ccc(Cl)cc1)c1cc(C(F)F)ccn1]

3-(4-chlorophenyl)-3-(4-(difluoromethyl)pyridin-2-yl)-N,N-dimethylpropan-1-amine (84). Prepared according to general procedure A (except 3-(4-chlorophenyl)-N,N-dimethyl-3-(pyridin-2-yl)propan-1-amine was protonated using TfOH (22 μL, 0.25 mmol) before the salt reaction) using 3-(4-chlorophenyl)-N,N-dimethyl-3-(pyridin-2-yl)propan-1-amine (69 mg, 0.25 mmol), (difluoromethyl)bis(4-methoxyphenyl)phosphane (82 mg, 0.275 mmol), Tf$_2$O (42 μL, 0.25 mmol), DBU (75 μL, 0.5 mmol), CH$_2$Cl$_2$ (2.5 mL), HCl (4 M in dioxane) (63 μL, 0.25 mmol), EtOH (2.25 mL) and H$_2$O (0.25 mL) at 40° C. for 20 hours. The crude material was purified by flash chromatography (neutral silica gel: 2% MeOH in CH$_2$Cl$_2$) to provide the title compound as a brown oil (53 mg, 0.163 mmol, 65% yield). $^1$H NMR (400 MHz, CDCl$_3$) δ: 8.67 (d, J=5.0 Hz, 1H), 7.25 (d, J=8.5 Hz, 7H), 6.54 (t, J=55.7 Hz, 1H), 4.24 (t, J=6.6 Hz, 1H), 2.68 (s, 3H), 2.57 (s, 6H), 2.47-2.37 (m, 1H); $^{13}$C NMR (101 MHz, CDCl$_3$) δ 162.69, 150.25, 143.10 (t, J=23.3 Hz), 140.45, 133.21, 129.42, 129.20, 119.80 (t, J=6.0 Hz), 118.27 (t, J=5.7 Hz), 112.92 (t, J=241.1 Hz), 56.89, 50.04, 43.90, 30.44; $^{19}$F NMR (377 MHz, CDCl$_3$) δ: −115.59 (dd, J=55.6, 3.7 Hz). IR ν$_{max}$/cm$^{-1}$ (film): 2953, 1681, 1611, 1570, 1420, 1410, 1383, 1090, 1039, 1015, 832. m/z HRMS (DART): [M+H]$^+$ calculated for C$_{17}$H$_{20}$ClF$_2$N$_2^+$=325.1278, found 325.1297.

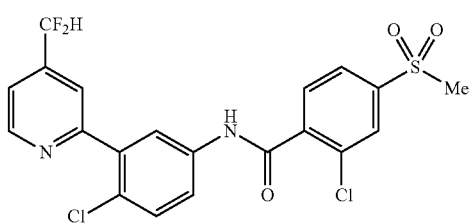 [SMILES: CS(=O)(=O)c1ccc(C(=O)Nc2ccc(Cl)c(-c3cc(C(F)F)ccn3)c2)c(Cl)c1]

2-chloro-N-(4-chloro-3-(4-(difluoromethyl)pyridin-2-yl)phenyl)-4-(methylsulfonyl)benzamide (88). Prepared according to general procedure A using 2-chloro-N-(4-chloro-3-(pyridin-2-yl)phenyl)-4-(methylsulfonyl)benzamide (105 mg, 0.25 mmol), (difluoromethyl)bis(4-methoxyphenyl)phosphane (82 mg, 0.275 mmol), Tf$_2$O (42 μL, 0.25 mmol), DBU (37 μL, 0.25 mmol), CH$_2$Cl$_2$ (2.5 mL), HCl (4 M in dioxane) (63 μL, 0.25 mmol), EtOH (2.25 mL) and H$_2$O (0.25 mL) at 40° C. for 25 hours. The crude material was purified by flash chromatography (silica gel: 60% EtOAc in toluene) to provide the title compound as a yellow solid (71 mg, 0.151 mmol, 60% yield). m.p. 124-127° C.; $^1$H NMR (400 MHz, CDCl$_3$) δ: 9.21 (s, 1H), 8.63 (d, J=5.1 Hz, 1H), 7.90 (dd, J=8.7, 2.6 Hz, 1H), 7.83 (d, J=1.7 Hz, 1H), 7.80 (s, 1H), 7.78 (d, J=2.7 Hz, 1H), 7.68 (dd, J=8.0, 1.7 Hz, 1H), 7.61 (d, J=8.0 Hz, 1H), 7.49 (d, J=8.7 Hz, 1H), 7.40-7.32 (m, 1H), 6.71 (t, J=55.7 Hz, 1H), 3.02 (s, 3H); $^{13}$C NMR (101 MHz, CDCl$_3$) δ 164.02, 157.28, 150.30, 143.54-142.75 (m), 140.92, 138.63, 137.31, 132.71, 131.54, 130.70, 129.33, 128.03, 126.22, 123.25, 122.40, 121.92 (t, J=6.1 Hz), 119.50 (t, J=5.7 Hz), 113.15 (t, J=241.4 Hz), 44.75; $^{19}$F NMR (376 MHz, CDCl$_3$) δ: −116.15 (d, J=55.8 Hz). IR ν$_{max}$/cm$^{-1}$ (film): 3015, 2932, 1678, 1609, 1546, 1488, 1469, 1367, 1310, 1155, 1095, 1033, 959, 892, 875, 749, 676, 607, 550. m/z HRMS (DART): [M+H]$^+$ calculated for C$_{20}$H$_{15}$Cl$_2$F$_2$N$^+$=471.0143, found 471.0138.

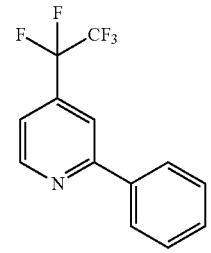 [SMILES: FC(F)(F)C(F)(F)c1ccnc(-c2ccccc2)c1]

4-(perfluoroethyl)-2-phenylpyridine. Prepared according to general procedure A using 2-phenylpyridine (29 μL, 0.2 mmol), 1,1'-(((perfluoroethyl)phosphanediyl)bis(4,1-phenylene))dipyrrolidine (97 mg, 0.22 mmol), Tf$_2$O (34 μL, 0.2 mmol), DBU (30 μL, 0.2 mmol), CH$_2$Cl$_2$ (2 mL), TfOH (18 μL, 0.2 mmol), MeOH (1 mL) and H$_2$O (36 μL, 2 mmol) at rt for 22 hours. The crude material was purified by flash chromatography (silica gel: 3% EtOAc in hexanes) to provide the title compound as a colorless oil (40 mg, 0.148 mmol, 74% yield). $^1$H NMR (400 MHz, CDCl$_3$) δ: 8.88 (d, J=5.1 Hz, 1H), 8.09-7.99 (m, 2H), 7.92 (s, 1H), 7.57-7.45 (m, 3H), 7.44 (dd, J=5.1, 1.5 Hz, 1H); $^{13}$C NMR (101 MHz, CDCl$_3$) δ: 158.88, 150.65, 138.17, 137.94, 137.70, 130.03, 129.13, 127.23, 123.16, 120.31 (t, J=37.9 Hz), 118.87 (t, J=5.8 Hz), 117.37 (t, J=6.1 Hz), 115.44-114.57 (m), 112.58 (q, J=38.7 Hz), 110.24 (q); $^{19}$F NMR (376 MHz, CDCl$_3$) δ−84.47, −117.05. IR ν$_{max}$/cm$^{-1}$ (film): 2957, 2923, 2853, 2360, 1558, 11471, 1457, 1214, 760, 667. m/z HRMS (DART): [M+H]$^+$ calculated for C$_{13}$H$_9$F$_5$N$^+$=274.0650, found 274.0662.

Example 6. General Synthesis of Additional Fluorinated Phosphines

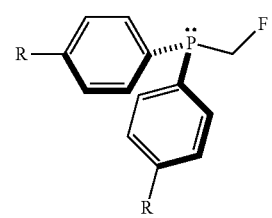

R = H, halo, alkyl, O(alkyl), N(alkyl)$_2$.

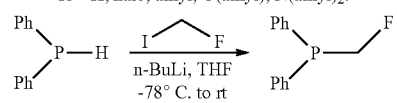

New J Chem 2020, 44 (33), 14306-14315

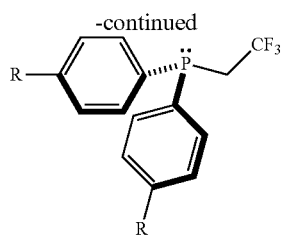

R = H, halo, alkyl, O(alkyl), N(alkyl)₂.

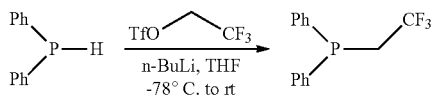

J Fluorine Chem 1999, 97 (1-2), 109-114

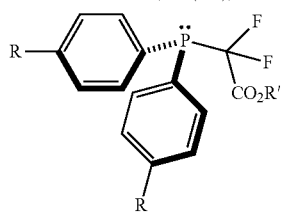

R = H, halo, alkyl, O(alkyl), N(alkyl)₂.
R' = alkyl

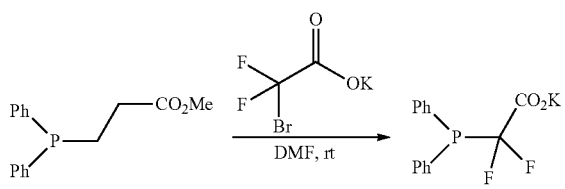

Chem Sci 2021, 12 (21), 7480-7485

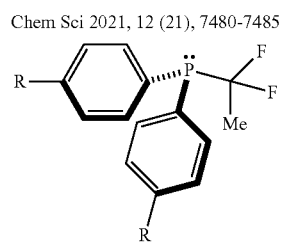

R = H, halo, alkyl, O(alkyl), N(alkyl)₂.

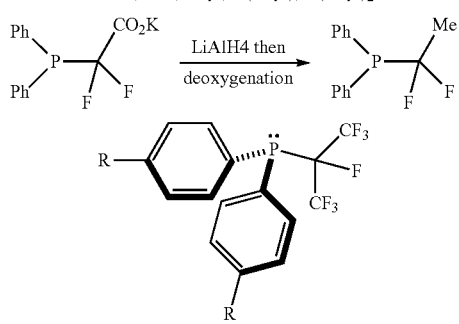

R = H, halo, alkyl, O(alkyl), N(alkyl)₂.

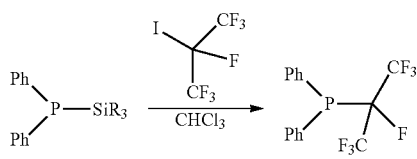

Chem Commun (Camb) 2009, (43), 6658-60

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A phosphine compound of Formula I:

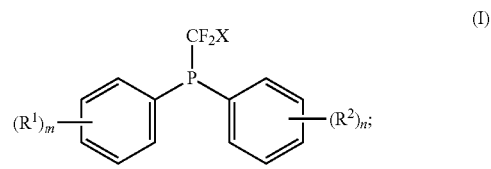

wherein
X is H, F, —($C_1$-$C_6$)perfluoroalkyl, or —($C_1$-$C_6$)alkyl;
$R^1$ and $R^2$ are each independently $NR^aR^b$, $OR^c$, $SR^d$, —($C_3$-$C_6$)cycloalkyl, or —($C_1$-$C_6$)alkyl;
$R^a$ and $R^b$ are each independently H, —($C_1$-$C_6$)alkyl, or —($C_3$-$C_6$)cycloalkyl; or
$R^a$ and $R^b$ taken together form a 5-membered or 6-membered heterocycle with the nitrogen moiety of $NR^aR^b$;
$R^c$ and $R^d$ are each independently H, —($C_1$-$C_6$)alkyl, or —($C_3$-$C_6$)cycloalkyl; and
m and n are each independently 1 or 2;
each —($C_1$-$C_6$)alkyl is independently unbranched or branched, and optionally substituted; and
X is not F when $R^1$ and $R^2$ are $CH_3$; and X is not F when $R^1$ and $R^2$ are $OCH_3$, $R^1$ and $R^2$ are each in the para-position, and m and n are each 1.

2. The compound of claim 1 wherein $R^1$ and $R^2$ are each in the para-position and m and n are each 1.

3. The compound of claim 1 wherein X is H, F, or $CF_3$.

4. The compound of claim 1 wherein $R^1$ and $R^2$ are $NR^aR^b$.

5. The compound of claim 4 wherein $R^a$ and $R^b$ are methyl or ethyl, or wherein $NR^aR^b$ is pyrrolidinyl or piperidinyl.

6. The compound of claim 1 wherein $R^1$ and $R^2$ are $OR^c$.

7. The compound of claim 6 wherein $R^c$ is methyl or ethyl.

8. The compound of claim 1 wherein X is F, and $R^1$ and $R^2$ are $NR^aR^b$.

9. The compound of claim 1 wherein X is F, and $R^1$ and $R^2$ are $N(CH_3)_2$ or 1-pyrrolidinyl.

10. The compound of claim 1 wherein X is H, and $R^1$ and $R^2$ are $OR^c$.

11. The compound of claim 1 wherein X is H, and $R^1$ and $R^2$ are methoxy or ethoxy.

12. The compound of claim 1 wherein the compound is:

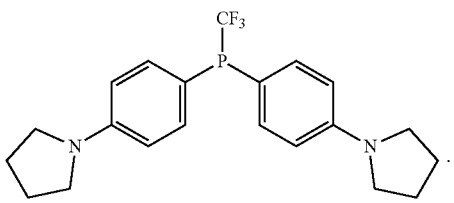 [SMILES: FC(F)(F)P(c1ccc(N2CCCC2)cc1)c1ccc(N2CCCC2)cc1]

13. The compound of claim 1 wherein the compound is:

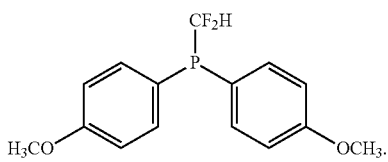 [SMILES: COc1ccc(P(c2ccc(OC)cc2)C(F)F)cc1]

14. A composition comprising the compound of claim 1 and one or more of an acid, a base, and a solvent.

15. A method for fluoroalkylation of an organic compound comprising:

a) contacting a phosphine compound of Formula I:

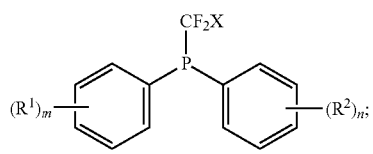

wherein
X is H, F, —($C_1$-$C_6$)perfluoroalkyl, or —($C_1$-$C_6$)alkyl;
$R^1$ and $R^2$ are each independently $NR^aR^b$, $OR^c$, $SR^d$, —($C_3$-$C_6$)cycloalkyl, or —($C_1$-$C_6$)alkyl;
$R^a$ and $R^b$ are each independently H, —($C_1$-$C_6$)alkyl, or —($C_3$-$C_6$)cycloalkyl; or
$R^a$ and $R^b$ taken together form a 5-membered or 6-membered heterocycle with the nitrogen moiety of $NR^aR^b$;
$R^c$ and $R^d$ are each independently H, —($C_1$-$C_6$)alkyl, or —($C_3$-$C_6$)cycloalkyl; and
m and n are each independently 1 or 2;
wherein each —($C_1$-$C_6$)alkyl is independently unbranched or branched, and optionally substituted;
an organic compound, and a solvent, under suitable reaction conditions to form a phosphonium salt of the organic compound; and b) contacting the phosphonium salt and an aqueous solution or a mixture of an organic solvent and a base;
wherein optionally the phosphonium salt is not isolated as a purified intermediate compound before contacting the intermediate with the aqueous solution;
wherein a fluoroalkylated organic compound is thereby formed.

16. The method of claim 15 wherein the organic compound is a nitrogen-containing heteroaryl.

17. The method of claim 16 wherein the nitrogen-containing heteroaryl comprises a pyridine, pyrimidine, pyridazine, pyrazine, quinoline, isoquinoline, naphthyridine, or quinazoline.

18. The method of claim 15 wherein a mixture of the phosphine compound, organic compound and solvent at step a) comprises a Brønsted base and sulfonic anhydride.

19. The method of claim 15 wherein the aqueous solution at step b) comprises a Brønsted acid or Brønsted base.

20. The method of claim 15 wherein the phosphine compound is:

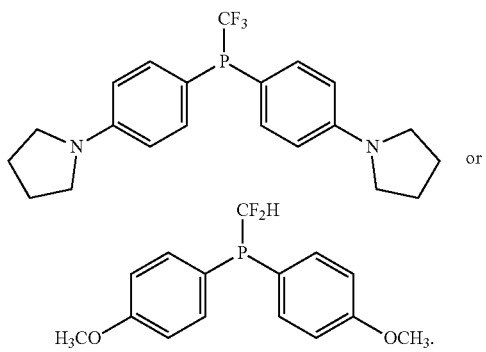

* * * * *